US009187752B2

(12) United States Patent
Bogosian et al.

(10) Patent No.: US 9,187,752 B2
(45) Date of Patent: Nov. 17, 2015

(54) HYBRID PORTABLE ORIGIN OF REPLICATION PLASMIDS

(75) Inventors: Gregg Bogosian, Clarkson Valley, MO (US); Julia P. O'Neil, Glendale, MO (US); Hong Q. Smith, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1615 days.

(21) Appl. No.: 11/990,660

(22) PCT Filed: Sep. 13, 2006

(86) PCT No.: PCT/US2006/035433
§ 371 (c)(1),
(2), (4) Date: Feb. 19, 2008

(87) PCT Pub. No.: WO2007/035323
PCT Pub. Date: Mar. 29, 2007

(65) Prior Publication Data
US 2009/0123966 A1  May 14, 2009

Related U.S. Application Data

(60) Provisional application No. 60/718,083, filed on Sep. 16, 2005.

(51) Int. Cl.
C12N 15/09 (2006.01)
C12N 15/00 (2006.01)
C12N 15/69 (2006.01)

(52) U.S. Cl.
CPC ..................................... *C12N 15/69* (2013.01)

(58) Field of Classification Search
None
See application file for complete search history.

(56) References Cited

U.S. PATENT DOCUMENTS

| | | | |
|---|---|---|---|
| 4,514,502 A | 4/1985 | Miwa et al. | |
| 4,703,012 A | 10/1987 | Boros et al. | |
| 5,023,171 A | 6/1991 | Ho et al. | |
| 5,565,333 A | 10/1996 | Devauchelle et al. | |
| 5,589,364 A | 12/1996 | Williams et al. | |
| 6,010,875 A | 1/2000 | Fischer | |
| 6,221,630 B1 | 4/2001 | Hopper | |
| 6,271,255 B1 * | 8/2001 | Leadlay et al. | 514/450 |
| 6,333,187 B1 | 12/2001 | Beekwilder et al. | |
| 6,544,782 B1 | 4/2003 | Malo et al. | |
| 6,569,678 B1 | 5/2003 | Malo et al. | |
| 6,806,066 B2 | 10/2004 | Bayer et al. | |
| 2006/0073574 A1 * | 4/2006 | Caffrey | 435/76 |

FOREIGN PATENT DOCUMENTS

WO    WO 93/01293    *   1/1993

OTHER PUBLICATIONS

Dennis et al., *Applied and Environmental Microbiology*, vol. 64, No. 7, p. 2710-2715. (Jul. 1998).
Jessen, et al., *Proceedings of the National Academy of Sciences of USA* National Academy of Science, Washington, DC, US, vol. 95, No. 9, p. 5121-5126 (Apr. 28, 1998).
Mayer M P, *Gene, Elsevier*, Amsterdam, NL, vol. 163, No. 1, p. 41-46 (Sep. 22, 1995).
Paterson, et al, *Journal of Bacteriology*, vol. 179, No. 18, p. 5768-5776 (Sep. 1997).
del Solar, et al, *Molecular Microbiology*, vol. 37, No. 3, p. 492-500 (Aug. 2000).
Kovach, et al, *Biotechniques*, vol. 16, No. 5, p. 800, 802, (1994).
Rakonjac et al., *Applied and Environmental Microbiology*, vol. 69, No. 9, p. 5104-5114 (Sep. 2003).
Atlung et al., Role of the Rom Protein in Copy Number Control of Plasmid pBR322 at Different Growth Rates in *Escherichia coli* K-12, *Plasmid* 41, pp. 110-119 (1999).
Blakely et al., Two Related Recombinases Are Required for Site-Specific Recombination at dif and cer in E. coli K12, *Cell*, vol. 75, pp. 351-361, Oct. 22, 1993.
Bolivar et al., Construction and Characterization of New Cloning Vehicles II. A Multipurpose Cloning System, *Gene*, 2 pp. 95-113 (1977).
Cesareni et al., Control of ColE1 DNA replication: The rop gene product negatively affects transcription from the replication primer promoter, *Proc. Natl. Acad. Sci. USA* 79, pp. 6313-6317, Oct. 1982.
Chang et al., Construction and Characterization of Amplifiable Multicopy DNA Cloning Vehicles Derived from the P15A Cryptic Miniplasmid, *Journal of Bacteriology*, pp. 1141-1156, Jun. 1978.
Colloms et al., Recombination at ColE1 cer Requires the *Escherichia coli* xerC Gene Product, a Member of the Lambda Integrase Family of Site-Specific Recombinases, *Journal of Bacteriology*, pp. 6973-6980, Dec. 1990.
Covarrubias et al., Construction and characterization of new cloning vehicles V. Mobilization and coding properties of pBR322 and several deletion derivatives including pBR327 and pBR328, *Gene*, 13 pp. 25-35 (1981).
Cozzarelli et al., A Minute Circular DNA From Escherichia Coli 15*, Department of Biochemistry, Stanford University School of Medicine, *PNAS* 60, pp. 992-999, May 10, 1968.
Guhathakurta et al., Involvement of ArgR and PepA in the pairing of ColE1 dimer resolution sites, *Microbiology* 141, pp. 1163-1171 (1995).
Guhathakurta et al., Accessory proteins impose site selectivity during ColE1 dimer resolution, *Molecular Microbiology* 20(3), pp. 613-620 (1996).
Hodgman et al., Nucleoprotein architecture and ColE1 dimer resolution: a hypothesis, *Molecular Microbiology* 29(2), pp. 545-558 (1998).
Horton et al., Engineering hybrid genes without the use of restriction enzymes: gene splicing by overlap extension, *Gene* 77, pp. 61-68 (1989).

(Continued)

*Primary Examiner* — Nancy T Vogel
(74) *Attorney, Agent, or Firm* — Senniger Powers LLP; James E. Davis

(57) ABSTRACT

The invention relates to modifying plasmid origins of replication to create hybrid origins of replication containing nucleotide sequences from more than one plasmid. The invention also relates to a modified origin of replication cassette that is portable or exchangeable due to the creation of multiple cloning sites flanking the origin of replication. Methods and plasmids for use in exchanging origins of replication are disclosed. Such modified or hybrid plasmids provide useful cloning tools that allow for regulation of the level of expression of a desired protein.

47 Claims, 14 Drawing Sheets

(56) References Cited

OTHER PUBLICATIONS

Ivanov et al., A conditional high-copy-number plasmid derivative of pBR322, *Microbiologica* 11(2), pp. 95-99, Apr. 1988.

Lahijani et al., High-yield production of pBR322-derived plasmids intended for human gene therapy by employing a temperature-controllable, point mutation, *Hum Gene Ther* 7(16), pp. 1971-80, Oct. 20, 1996.

Lutz et al., Independent and tight regulation of transcriptional units in *Escherichia coli* via the LacR/O, the TetR/O and AraC/$I_1$-$I_2$ regulatory elements, *Nucleic Acids Research* 25(6), pp. 1203-1210 (1997).

Mayer, A new set of useful cloning and expression vectors derived from pBlueScript, *Gene* 163(1), pp. 41-46, Sep. 22, 1995.

Michaela et al., ColE1 multimer formation triggers inhibition of *Escherichia coli* cell division, *Molecular Microbiology* 9(5), pp. 1089-1095 (1993).

Peden, Revise sequence of the tetracycline-resistance gene of pBR322, *Gene* 22, pp. 277-280 (1983).

Ray et al., Stabilization of the Cloning Vector pACY184 by Insertion of F Plasmid Leading Region Sequences, *Plasmid* 11, pp. 272-275 (1984).

Rose, The nucleotide sequence of pACYC184, *Nucleic Acids Research* 16(1), p. 355 (1988).

Yoshimasa et al., Replication of Colicin E1 Plasmid DNA in Cell Extracts, *Proc. Nat. Acad. Sci. USA* 71(3), pp. 802-806, Mar. 1974.

Yoshimasa et al., Replication of Colicin E1 Plasmid DNA in Cell Extracts*: II. Selective Synthesis of Early Replicative Intermediates, *Proc. Nat. Acad. Sci. USA* 71(4), pp. 1403-1407, Apr. 1974.

Sarkar et al., Identification of multicopy suppressors of the pcnB plasmid copy number defect in Escherichia coli, *Mol Genet Genomics* 268(1), pp. 62-69, Sep. 2002 (Epub. Aug. 13, 2002).

Soberon et al., Construction and characterization of new cloning vehicles. IV. Deletion derivatives of pBR322 and pBR325, *Gene* 9, pp. 287-305 (1980).

Stirling et al., The arginine repressor is essential for plasmid-stabilizing site-specific recombination at the ColE1 cer locus, *The EMBO Journal* 7(13), pp. 4389-4395 (1988).

Stirling et al., xerB, an *Escherichia coli* gene required for plasmid ColE1 site-specific recombination, is identical to pepA, encoding aminopeptidase A, a protein with substantial similarity to bovine lens leucine aminopeptidase, *The EMBO Journal* 8(5), pp. 1623-1627 (1989).

Dietrich et al, Organization of transcriptional signals in plasmids pBR322 and pACYC184, *Proc. Natl. Acad. Sci. USA* 78(1), pp. 167-171, Jan. 1981.

Summers et al., Multimer resolution systems of ColE1 and ColK: localization of the crossover site, *Mol. Gen. Genet* 201, pp. 334-338 (1985).

Summers et al., Resolution of ColE1 dimers require a DNA sequence implicated in the three-dimensional organization of the *cer* site, *The Embo Journal* 3, pp. 851-858 (1988).

Summers, Derivatives of ColE1 cer show altered topological specificity in site-specific recombination, *The EMBO Journal* 8(1), pp. 309-315 (1989).

Summers, The kinetics of plasmid loss, *Elsevier Science Publishers Ltd.*, pp. 273-278, 1991.

Summers et al, Multicopy plasmid instability: the dimer catastrophe hypothesis, *Molecular Microbiology* 8(6), pp. 1031-1038 (1993).

Sutcliffe, Complete nucleotide sequence of the *Escherichia coli* pBR322, *Col Spring Harb. Symp Quant. Biol.* 43(1), pp. 77-90 (1979).

Jun-Ichi et al., Replication of Colicin E1 Plasmid DNA in Cell Extracts*. Origin and Direction of Replication, *Proc. Nat. Acad. Sci. USA* 71(6), pp. 2260-2264, Jun. 1974.

Watson, A new revision of the sequence of plasmid pBR322, *Gene* 70, pp. 399-403 (1988).

paCYC177: description & restriction map, Nov. 19, 2004 http://www.fermentas.com/techinfo/nucleicacids/mappacyc177.htm.

pBR322 GenBank/EMBL sequence accession numbers J01749, K00005, L08654, M10282, M10283, M10286, M10356, M10784, M10786, M33694, V01119, Jun. 17, 2004, Restriction sites of the pBR322 DNA, Jun. 17, 2004.

PCT/US2006/035433 Internat. Search Report/Written Opin., Jan. 23, 2007.

EP06803399.2-1222 Comm. Pursuant to Article 94(3)EPC.

Iordanescu et al., Replication Termination for Staphylococcal Plasmids: Plasmids pT181 and pC221 Cross-React in the Termination Process, Journal of Bacteriology, vol. 170, No. 8, p. 3427-3434, (Aug. 1988).

U.S. Appl. No. 60/652,390, filed Feb. 11, 2005, 64 pages.

\* cited by examiner

FIG 2
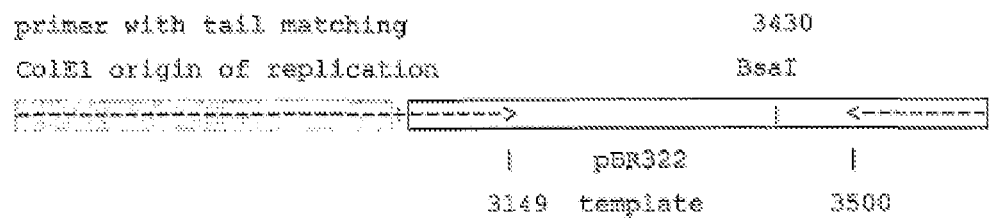
FIG 2A
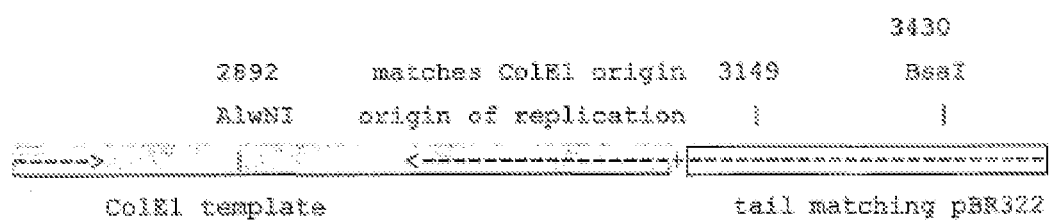
FIG 2B
pXT975
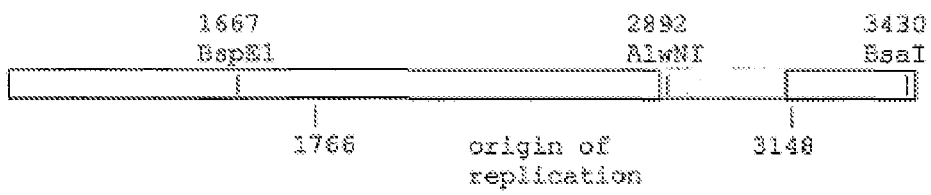
FIG 2C
key: box indicates pBR322 sequences
grey indicates ColE1 sequences FIG 3
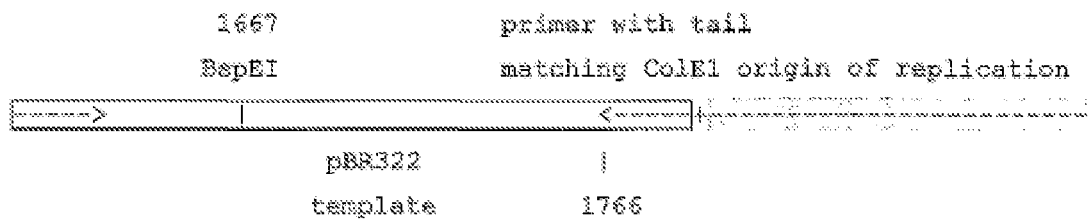
FIG 3A
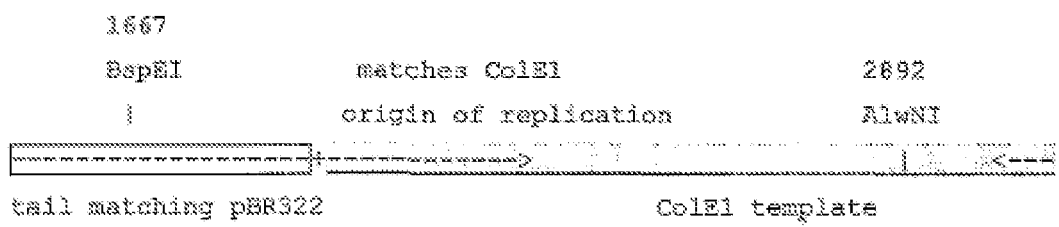
FIG 3B
pXT976
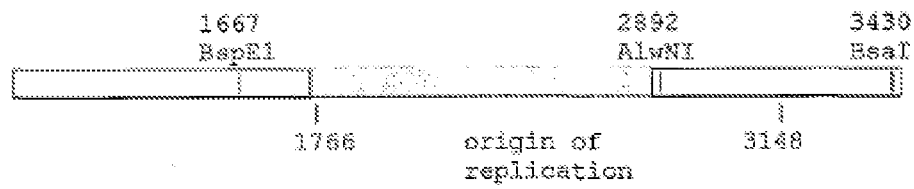
FIG 3C
key: box indicates pBR322 sequences
grey indicates ColE1 sequences pBR322
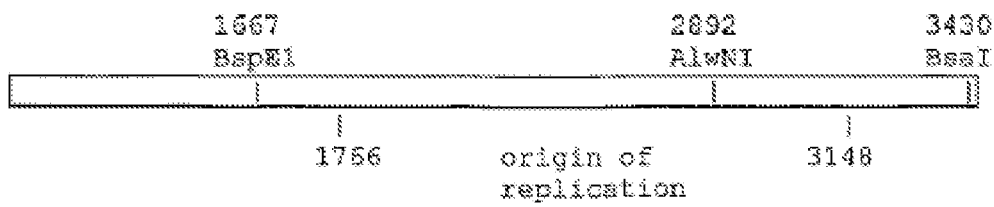
pXT975
pXT976
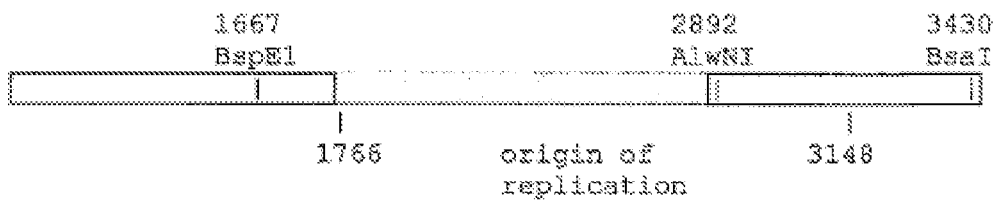
pXT977
key: box indicates sequences derived from the pBR322 origin of replication
grey indicates sequences derived from the ColE1 origin of replication
FIG 4

FIG 5
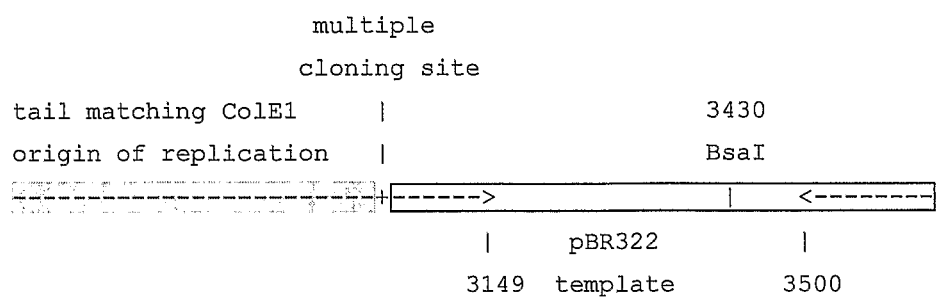
FIG 5A
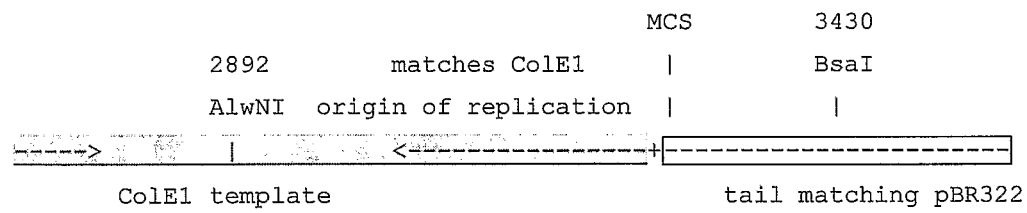
FIG 5B
FIG 5C key: box indicates pBR322 sequences
grey indicates ColE1 sequences pXT995 pXT1001 pXT1000 pXT988 key:   box indicates pBR322 sequences
       grey indicates ColE1 sequences key: box indicates pBR322 origin of replication sequence

```
                                            BstZ17I
2222 CCCAGTCACGT.AGCGATAGCGGAGTGTATACTGGCTTAACTATGCGGCA 2270
     ||    || | |||| |||'||||||||||||||||| |||||| |
 568 CCGCCGGACATCAGCGCTAGCGGAGTGTATACTGGCTT.ACTATGTTGGC 616

2271 TCAGAGCAGATTGTACTGAGAGTGCACCATATGCGGTGTGAAATA...CC 2317
     | ||  ||  |||         |||||  ||| ||    | |||| |  |
 617 ACTGATGAGGGTGTCAGTGAAGTGCTTCATGTGGCAGGAGAAAAAGGCT 666

2318 GCACAGATGCGTAAGGAGAAAATACCGCATCAGGCGCTCTTCCGCTTCCT 2367
     |||| | ||||||  || |||| ||   |   ||||    | |||||||||||
 667 GCACCGGTGCGTCAGCAGAATAT.GTGATACAGGATATATTCCGCTTCCT 715

2368 CGCTCACTGACTCGCTGCGCTCGGTCGTTCGGCTGCGGCGAGCGGTATCA 2417
     |||||||||||||||| |||||||||||||| ||||||||||||||| |
 716 CGCTCACTGACTCGCTACGCTCGGTCGTTCGACTGCGGCGAGCGGAAATG 765

2418 GCTCACTCAAAGGCGGTAATACGGTTATCCACAGAATCAGGGGATAACGC 2467
     ||| ||  |  || | |         |
 766 GCTTACGAACGGGGCGGAGATTTCCT 791 — — — — — — — — — —

2468 AGGAAGAACATGTGA 2483

2484 GCAAAAGGCCAGCAAAAGGC....CAGGAACCGTAAAAAGGCCGCGTTGC 2529
     | || | |||||| || | |    |||| |  || | | | |||||||
 792 GGAAGATGCCAGGAAGATACTTAACAGGGA.AGTGAGAGGGCCGCGGCAA 840

2530 TGGCGTTTTTCCATAGGCTCCGCCCCCCTGACGAGCATCACAAAAATCGA 2579
     |  |||||||||||||||||||||||||||||||| ||||||||| |||  ||
 841 AGCCGTTTTTCCATAGGCTCCGCCCCCCTGACAAGCATCACGAAATCTGA 890

2580 CGCTCAAGTCAGAGGTGGCGAAACCCGACAGGACTATAAAGATACCAGGC 2629
     ||||||| ||||  ||||||||||||||||||||||||||||||||||||
 891 CGCTCAAATCAGTGGTGGCGAAACCCGACAGGACTATAAAGATACCAGGC 940

2630 GTTTCCCCCTGGAAGCTCCCTCGTGCGCTCTCCTGTTCCGACCCTGCCGC 2679
     ||||||||||| |||||||||||||||||||||||||||| ||  |  | |
 941 GTTTCCCCCTGGCGGCTCCCTCGTGCGCTCTCCTGTTCCTGCCTTTCGGT 990

FIG 9A

2680 TTACCGGATACCTGTCCGCCTTTCTCCCTTCGGGAAGCGTGGCGCTTTCTCA 2731
     ||||||| |  |  ||||| ||| | | ||       |
 991 TTACCGG.TGTCATTCCGCTGTTATGGCCGCGTTTGTCTCA 1030 — — —
```

```
2732 TAGCTCACGCTGTAGGTATCTCAGTTCGGTGTAGGTCGTTCGCTCCAAGC 2781
     | ||    |   |  ||||||| | |||||  |||||||||||||
1031 TTCCAC.....GCCTGACACTCAGTTCCGGGTAGGCAGTTCGCTCCAAGC 1075

2782 TGGGCTGTGTGCACGAACCCCCGTTCAGCCCGACCGCTGCGCCTTATCC 2831
     ||| ||||  ||||||||||||||||||||  ||||||||||||||||||
1076 TGGACTGTATGCACGAACCCCCGTTCAGTCCGACCGCTGCGCCTTATCC 1125

2832 GGTAACTATCGTCTTGAGTCCAACCCGGTAAGACACGACTTATCGCCACT 2881
     |||||||||||||||||||||||||||||| ||||||| |   | | |||||
1126 GGTAACTATCGTCTTGAGTCCAACCCGGAAAGACATGCAAAAGCACCACT 1175

AlwNI
2882 GGCAGCAGCCACTGGTAACAGGATTAGCAGAGCGAG 2917
     ||||||||||||||||||||  |  ||||  |||  ||
1176 GGCAGCAGCCACTGGTAATTGATTTAGAGGAGTTAG 1211

2718 GTATGTAGGCGGTGCTACAGAGTTCTTGAAGTGGTGGCCTAACTAC 2963
                             ||||||||  ||  |    ||
     - - - - - - - - - 1212 TCTTGAAGTCATGCGCCGGTTAA 1234

2964 GGCTACACTAGAAGGACAGTATTTGGTATCTGCGCTCTGCTGAAGCCAGT 3013
     ||||| |||  |||||||  ||||||  ||||||||||| |  ||||||||
1235 GGCTAAACTGAAAGGACAAGTTTTGGTGACTGCGCTCCTC.CAAGCCAGT 1283

3014 TACCTTCGGAAAAAGAGTTGGTAGCTCTTGATCCGGCAAACAAACCACCG 3063
     ||||| |   ||||||||||||||||   |    |  || |||| 1330
1284 TACCTCGGTTCAAAGAGTTGGTAGCTC...AGAGAACCTTCGAAAAACCG 1330

3064 CTGGTAGCGGTGGTTTTTTTGTTTGCA.AGCAGCAGATTACGCGCAGAAA 3112
     |         || ||||||||  |||| || ||||  ||||||||||||||
1331 CCCTGCAAGGCGGTTTTTTCGTTTTCAGAGCAAGAGATTACGCGCAGACC 1380

3113 AAAAGGATCTCAAGAAGATCCTTTGAT 3139
     ||||  |||||||||||||||| |  | ||
1381 AAAACGATCTCAAGAAGATCATCTTAT 1407

| NsiI

ATGCATGTTATCCCTAGAACGGGAGCGTCAGCCGGAAATACAGGAACGCA

CGCTGGATGGCCCTTCGCTGGGATGGTGAAACCATGAAAAATGGCAGCTT

```
                                                *
```
CAGTGGATTAAGTGGGGGTAATGTGGCCTGTACCCTCTGGTTGCATAGGT

```
                                        this G not in Genbank
                        +1 of RCD   |
```
ATTCATACGGTTAAAATTTATCAGGCGCGATCGCGGCAGTTTTTCGGGTG
```
                                                    |
                                                A in Genbank
```

GTTTGTTGCCATTTTTACCTGTCTGCTGCCGTGATCGCGCTGAACGCGTT end RCD

TTAGCGGTGCGTACAATTAAGGGATTATGGTAAATCCACTTACTGTCTGC

```
            TaqI

#|
```
CCTCGTAGCCATCGAGATAAACCGCACGAAATCGTGTCAGCCAGCAGCCG

NotI
CGGCCGC
```
        |
```
3068

FIG 10 key:  box indicates pBR322 origin of replication sequences
grey indicates *cer* site sequences

HYBRID PORTABLE ORIGIN OF REPLICATION PLASMIDS

This application is a §371 U.S. national phase application of International Application No. PCT/US2006/035433 filed Sep. 13, 2006, which claims priority benefit to U.S. 60/718,083 filed Sep. 16, 2005, the entire contents of which are incorporated herein.

FIELD OF THE INVENTION

The invention relates to modifying plasmid origins of replication and, more specifically, to a modified portable origin of replication for plasmids pBR322 or pACYC184. In particular, methods and plasmids for use in exchanging origins of replication are disclosed.

DESCRIPTION OF RELATED ART

Many species of bacteria contain small circular extrachromosomal genetic elements, known as plasmids. Plasmids replicate independently of the bacterial cell's chromosome. They are usually small, circular, double-stranded molecules, found in all types of bacteria (perhaps all species, although not all strains, of bacteria). The number of copies (i.e., the copy number) varies from plasmid type to plasmid type, and a cell can have more than one type of plasmid. Plasmids contain genes that are non-essential, but often beneficial, to the bacterium. Common genes found in plasmids include those encoding plasmid replication (i.e., the origin of replication) and cellular maintenance, antibiotic resistance, bacteriocin production, sex determination, and other cellular functions (Kornberg and Baker, *DNA Replication,* 2nd ed. (1991)).

A number of plasmids are known in the art such as pBR322, pMB1, p15A, pACYC184, pACYC177, ColE1, pBR3286, p1, pBR26, pBR313, pBR327, pBR328, pPIGDM1, pPVUI, pF, pSC101 and pC101p-157.

Many microbial plasmid expression vectors are derivatives of the pBR322 plasmid. The plasmid pBR322 is one of the most commonly used *Escherichia coli* cloning vectors, a map of which is shown in FIG. 1. pBR322 is 4361 base pairs in length and contains the following genetic elements: (1) the replicon responsible for the replication of plasmid (the origin of replication is from plasmid pMB1); (2) the rop gene coding for the Rop protein, which promotes conversion of the unstable RNA I-RNA II complex to a stable complex and serves to decrease copy number; (3) the bla gene, coding for beta-lactamase that confers resistance to ampicillin; and (4) the tetR gene, encoding the tetracycline resistance protein. The complete nucleotide sequence of the plasmid pBR322 has been determined, revealing several unique restriction sites useful for the cloning of DNA fragments.

The indicated rep region is sufficient to promote replication. DNA replication initiates at position 2533 and proceeds in the direction indicated in FIG. 1. Plasmids carrying the pMB1 and ColE1 replicons are incompatible, but they are fully compatible with those carrying the p15A replicon (such as the standard cloning vectors pACYC177 and pACYC184).

The plasmid pBR322 has several important advantages that have led to it being widely and successfully employed as the starting plasmid for constructing many expression vectors. The advantages include that pBR322 has been completely sequenced, has several unique restriction sites useful for cloning DNA fragments, is not self-transmissible, and is readily available.

However, there are a number of disadvantages associated with using pBR322. One of the important features of a plasmid is its copy number, which is set by the region on the plasmid called the origin of replication. The origin of replication on the plasmid pBR322 extends from numbered coordinates 1766 to 3148.

The copy number of a plasmid, that is, the average number of plasmid molecules per cell, is a fundamental plasmid characteristic that is determined and regulated by an array of plasmid genetic elements (reviewed in *The Biology of Plasmids,* David K. Summers, Blackwell Science, 1996; and in *Plasmid Biology,* Barbara E. Funnell and Gregory J. Phillips, American Society for Microbiology Press, 2004). Each specific plasmid has a characteristic plasmid copy number. Of the dozens of plasmids studied to date, specific plasmid copy numbers have been found to range from as few as one copy per cell to hundreds of copies per cell. The plasmid copy number has a number of important effects on the host cell. Often, over-expression of a gene of interest on a multicopy number plasmid can have toxic effects on a cell and make cloning the gene of interest difficult if not impossible. Under conditions where high copy number is undesirable, it is possible to utilize a lower copy number plasmid in these circumstances, such as pACYC184, which is considered a low copy number plasmid. In certain cases, it is desirable to utilize a plasmid with a high copy number, such as the pBluescript® series of vectors (available from Stratagene, La Jolla, Calif.) that are modified ColE1 plasmids with a high copy number and other useful features.

One of the disadvantages of pBR322 is its copy number of about 20, placing it in the low copy number range. The origin of replication of pBR322 is derived from the plasmid pMB1 and is homologous to the origin of replication region on plasmid ColE1. Thus, while it is often stated that pBR322 has a ColE1 origin of replication, it actually has a pMB1 origin of replication.

Since the plasmid pBR322 has a low copy number, it is often necessary to utilize a different plasmid with a high copy number to generate large amounts of an over-expressed desired protein. In other instances, it is desirable to utilize a low copy number plasmid, in order to get expression of certain toxic proteins, where the host cell does not tolerate over-expression. Thus, it has previously been the case that if a plasmid with a significantly higher or lower plasmid copy number than that of pBR322 were desired for cloning purposes, a plasmid without the many useful features of pBR322 would have to be utilized. It would be a great benefit to provide a modified pBR322 plasmid that has some characteristics of the pMB1 ORI and some characteristics of another ORI such as the ORI from ColE1. It would also be of great benefit to provide a modified pBR322 plasmid that has easily exchangeable origin of replication, which could be utilized as an expression plasmid, and that otherwise remains unchanged. In this manner, one could still have the benefits of the pBR322 plasmid, and also have the flexibility of being able to change the origin of replication to any desired alternative origin of replication.

When there is a preference for using a particular plasmid, such as desired antibiotic resistance markers or restriction sites, it would be beneficial to be able to modify the origin of replication to obtain a desirable copy number. Previously, there has been no success modifying the origin of replication of pBR322 with a different plasmid origin of replication region because the pBR322 origin of replication region, 1766-3148, is not flanked by unique restriction sites. Beyond coordinate 3148, the first unique restriction site is located within the ampicillin resistance gene. Thus, it is not possible to simply "cut and paste" other origin of replications into the pBR322 plasmid backbone.

Thus, there exists a need for a modified pBR322 plasmids, containing a portable origin of replication, preferably flanked by multiple unique restriction sites known as multiple cloning sites (MCS), creating an easily exchangeable pBR322 origin of replication. Such modified pBR322 plasmids will provide useful cloning tools that allow for regulation of the level of expression of desired or target gene products.

A similar situation exists for several other plasmids, such as pACYC184, p1, plasmid F and pSC101. pACYC184, with its low copy number and its origin of replication region lacking unique restriction sites for facilitating exchange of the origin of replication region could be readily used if were modified with flanking MCS.

Bacteriophage P1 exists inside *E. coli* cells in the quiescent prophage state as an independent plasmid with a copy number of about 2-3 per cell, rather than being integrated into the *E. coli* chromosome like most other prophage. Thus, the origin of replication of the P1 genome can be employed as a plasmid origin of replication. The origin of replication of P1 contains genetic elements that provide for stable inheritance of the plasmid, making this origin of replication attractive for use as the basis of a stable 2-3 copy number plasmid cloning vector.

The plasmid F, with a plasmid copy number of about 1-2 per cell, is a plasmid of *E. coli* involved in genetic exchange. The origin of replication of the plasmid F contains genetic elements that provide for stable inheritance of the plasmid, making the plasmid F origin of replication attractive for use as the basis of a stable 1-2 copy number plasmid cloning vector.

The plasmid pSC101, with a plasmid copy number of about 5 per cell, is a plasmid isolated from *Salmonella* that can replicate in *E. coli* cells. The parent plasmid of pSC101 is plasmid R6-5, that is in turn derived from the plasmid R6. The origin of replication is thus the same on the plasmids pSC10, R6-5, and R6. The origin of replication of P1 contains genetic elements that provide for stable inheritance of the plasmid, making this origin of replication attractive for use as the basis of a stable 5 copy number plasmid cloning vector.

Most commonly used multi-copy cloning vectors are inherited in an unstable fashion, being lost under non-selective conditions at frequencies of between $10^{-2}$ to $10^{-5}$ per cell per generation (Summers and Sherratt, 1984). However, the multi-copy plasmid ColE1 is stably inherited, suggesting that ColE1 includes a stabilizing function. It was found that partitioning of ColE1-like plasmid between cells at division is random; this was a puzzling observation, given the stable inheritance of ColE1 versus the unstable inheritance of smaller ColE1-like cloning vectors. The puzzle was solved with the finding that plasmid multimers form with the smaller ColE1-like cloning vectors, and that this multimerization was the cause of the unstable inheritance because plasmid multimers are maintained at a lower copy number than plasmid monomers (the content of plasmid-monomer equivalents is the same per cell), and thus plasmid multimer-containing cells are more at risk of giving rise to plasmid-free segregants after cell division. A region on ColE1 was found that functioned to resolve plasmid multimers back to monomers, and was designated cer (for ColE1 resolution) (Summers and Sherratt, 1984).

A similar stability function was found on plasmid ColK, and the identification of a region of nucleotide sequence homology on the two plasmids allowed the cer site to be pinpointed to a region of about 150 bp (Summers et al., 1985). The molecular biology of the cer site, and the involvement of host factors in multimer resolution, has been studied extensively (Summers and Sherratt, 1988; Summers, 1989; Summers, 1991; Summers et al., 1993; Hodgman et al., 1998). At least four chromosomally-encoded proteins are involved, including ArgR, the repressor of arginine biosynthesis (Stirling et al., 1988); PepA, aminopeptidase A (Stirling et al., 1989); and the recombinases XerC (Colloms et al., 1990) and XerD (Blakely et al., 1993). This dependence on host factors is likely to put constraints on the functional host range of the cer system. cer-mediated recombination occurs in a unidirectional fashion, ensuring only the conversion of multimers to monomers (Guhathakurta and Summers, 1995; Guhathakurta et al., 1996).

Multimer resolution is necessary but not sufficient for the stable maintenance of ColE1. A promoter within cer, pcer, directs the synthesis of a 70 nucleotide untranslated RNA molecule that is not required for multimer resolution, but is essential for stable plasmid maintenance. This RNA molecule, known as RCD (regulator of cell division), arrests the division of cells containing plasmid multimers (Patient and Summers, 1993). This effect of RCD prevents multimer-containing cells from dividing and producing plasmid-free segregant cells. Transcription from pcer occurs almost exclusively in multimer-containing cells, with very little RCD detected in monomer-containing cells. This suggests that the pcer promoter is topologically constrained, requiring a degree of supercoiling only found on plasmid multimers in order for the promoter to be activated. It is not known how RCD exerts its effects on cell division. The use of the RCD molecule to create "quiescent" cells has been claimed in Summers and Rowe, U.S. Pat. No. 6,190,867.

Thus, the present invention addresses the foregoing problems listed in the art by creating modified hybrid pBR322 or pACYC184 plasmids. Examples of the problems listed in the art are: 1) the need for either high or low copy plasmids; 2) the need for portability of the origin of replication between plasmids; and 3) the need for customizable plasmids, i.e., the ability to add specific genetic elements to a plasmid, such as the cer region that increases plasmid stability in culture. Some hybrid pBR322 or pACYC184 plasmids contain a cer site in order to provide for prolonged plasmid stability in culture. This plasmid stability is particularly desired for modified constructs that produce a desired protein when such constructs need to be cultured for many (>20) generations in the absence of antibiotic selection.

SUMMARY OF THE INVENTION

The present invention is directed to a hybrid origin of replication comprising nucleotide sequences from an origin of replication from at least two different plasmids. The present invention includes plasmids modified to contain a portable origin of replication, preferably flanked by multiple unique restriction sites known as multiple cloning sites (MCS), creating an easily exchangeable origin of replication. Such modified plasmids will provide useful cloning tools that allow for regulation of the level of expression of desired or target gene products.

An embodiment of the present invention includes a chimeric or hybrid origin of replication comprising nucleotide sequences from an origin of replication from at least two different plasmids. Such hybrid origins of replication comprise nucleotide sequences from pBR322 (SEQ ID 1) and nucleotide sequences from ColE1 (SEQ ID 6). Another hybrid origin of replication comprise nucleotide sequences from position 1766 to AlwNi restriction site in a pBR322 plasmid linked to nucleotide sequences from an AlwNi restriction site to position 3148 in a ColE1 plasmid (SEQ ID 7). Yet another hybrid origin of replication comprises nucleotide sequences from position 1766 to AlwNI restriction site in a ColE1 plasmid linked to nucleotide sequences from an AlwNI restriction site to position 3148 in a pBR322 plasmid (SEQ ID 12). Another hybrid origin of replication comprises nucleotide sequences from pBR322 and pACYC184 (SEQ ID 28). For some embodiments of the present invention, at least 200 nucleotides, more preferably 250 nucleotides, from a one origin of replication is linked to nucleotides from a different origin of replication.

Another embodiment of the present invention includes an exchangeable origin of replication cassette comprising a nucleotide sequence of an origin of replication flanked on each side by nucleotide sequences coding for at least one cloning site; said cloning site not within a regulatory or structural coding region. In certain embodiments, the exchangeable origin of replication cassette may comprise multiple cloning sites such as: SEQ ID NO: 30 (the BglII-NsiI-NotI multiple cloning site fragment) and/or SEQ ID NO: 31 (the SacI-SpeI-BglII multiple cloning site fragment). The recognition sites for these restriction endonucleases are AGATCT for BglII, ATGCAT for NsiI, GCGGCCGC for NotI, GAGCTC for SacI, and ACTAGT for SpeI.

Another embodiment of the present invention includes modified plasmids containing an exchangeable origin of replication cassette comprising a nucleotide sequence of an origin of replication flanked on each side by nucleotide sequences coding for at least one cloning site. Additional embodiments include a modified plasmid wherein the exchangeable origin of replication comprises the nucleotide sequences from the pBR322, ColE1, pMB1, P15A or pACYC184 origin of replication.

% Yet further embodiments include a modified plasmid wherein the exchangeable origin of replication comprises a hybrid ColE1 and pMB1 origin of replication.

Embodiments of the present invention include a modified plasmid based on the pBR322 plasmid backbone, or a plasmid exhibiting at least 70% nucleotide sequence identity with the origin of replication regions of pBR322. The remainder of the origin of replication is comprised of sequences from plasmids pACYC184 and/or ColE1. This means there is an overall homology of at least 70% between the ORI of pBR322 and a second ORI being used to create the hybrid ORI. In one such embodiment the plasmid is pXT977.

This plasmid could be further modified so that multiple cloning sites flank the hybrid origin of replication. In one such embodiment, the plasmid is pX988. An additional embodiment includes a modified plasmid based on the pBR322 plasmid backbone, or a plasmid exhibiting at least 70% nucleotide sequence identity with the origin of replication regions of pBR322 or pACYC184, comprising a pMB1 origin of replication flanked by multiple cloning sites. In one such embodiment, the plasmid is pXT995.

In additional embodiments, the modified plasmid vector further comprises bovine somatotropin (bST) expression elements, and is represented pXT757, pXT985, pXT986, pXT987, pXT996, pXT1002, pXT1003, pXT1004, pXT1007, pXT1109, or pXT1110.

Additional embodiments include a method of creating an exchangeable origin of replication cassette within a first plasmid comprising:
  (a) using primers to amplify the existing origin of replication within the first plasmid, wherein the primers comprise an annealing region and a region comprising at least one cloning site that corresponds to a cloning site in a second plasmid;
  (b) isolating the PCR amplicons, said amplicons containing an origin of replication region, an annealing region and at least one cloning site.

In yet additional embodiments, the invention covers a method of exchanging an origin of replication region between a first plasmid and a second plasmid comprising:
  (a) using primers to amplify the existing origin of replication within the first plasmid, wherein the primers comprise an annealing region and a region comprising at least one cloning site that corresponds to a cloning site in a second plasmid;
  (b) isolating the PCR amplicons, said amplicons containing an origin of replication region, an annealing region and at least one cloning site;
  (c) digesting the PCR amplicons with a restriction enzyme that recognizes the at least one cloning site;
  (d) digesting the second plasmid with a restriction enzyme that recognizes the at least one cloning site so as to cut out the existing origin of replication;
  (e) ligating the PCR amplicons of the first plasmid into the second plasmid.

Yet further embodiments include a bacterial host cell transformed with any of the modified plasmids described above. Additional embodiments include a kit comprising any of the modified plasmids described above. The kits may also include compatible competent host cells.

The invention may encompass a method of producing a recombinant protein of interest comprising:
  (a) transforming a suitable bacterial host cell compatible with a ColE1, MB1, p15A or hybrid ColE1, MB1, p15A replication system, with any one of the modified plasmids described above containing a gene encoding a recombinant protein of interest, operatively linked to expression control nucleotide sequences; and
  (b) growing a culture of said suitable bacterial host transformed with said modified plasmids under suitable conditions for expression of said recombinant protein; and
  (c) recovering and purifying the protein of interest.

In yet a further embodiment, the invention may include a method of producing plasmid DNA in *E. coli* comprising:
  (a) transforming a suitable *E. coli* strain with any modified plasmids described above; and
  (b) growing a culture of said *E. coli* transformed with said modified plasmids under conditions which allow replication of said vector.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

FIG. 2 shows the design of a modified pBR322 construct, pXT975. In panel 2A, the design of one of the primers used to create the modified plasmid is shown with a region at coordinate 3149 that is homologous to pBR322 and a long tail region that is homologous to the ColE1 origin of replication. In panel 2B, the design of a second primer is shown with a region at coordinate 2892 that is homologous to the ColE1 origin of replication and a tail region that is homologous to the pBR322 plasmid at coordinate 3149. Panel 2C, shows the modified pBR322 construct, pXT975 in which positions 2892-3148 of the origin of replication have been replaced with the corresponding region from the ColE1 origin to create a hybrid origin of replication.

FIG. 3 shows the design of a modified pBR322 construct, pXT976. In panel 3A, the design of one of the primers used to create the modified plasmid is shown with a region at coordinate 1667 that is homologous to pBR322 and a long tail region that is homologous to the ColE1 origin of replication. In panel 3B, the design of a second primer is shown with a region at coordinate 2892 that is homologous to the ColE1 origin of replication and a tail region that is homologous to the pBR322 plasmid at coordinate 1667. Panel 3C, shows the modified pBR322 construct, pXT976 in which positions 1766-2892 of the origin of replication have been replaced with the corresponding region from the ColE1 origin to create a hybrid origin of replication.

FIG. 4 shows a comparison of the origin of replication regions among pBR322, pXT975, pXT976, and pXT977. The modified pBR322 construct, pXT977, has the entire pBR322 (pMB1) origin of replication replaced with the origin of replication of ColE1 (nucleotides 1766-3148).

FIG. 9 shows a comparison of the nucleotide sequences of the origins of replication from pBR322 (top nucleotide sequence, SEQ ID NO: 1) and pACYC184 (lower nucleotide sequence, SEQ ID NO: 24).

FIG. 10 shows the nucleotide sequence of the NsiI-NotI fragment of the hybrid plasmid pXT1007 (SEQ ID NO: 32), containing a cer site.

DETAILED DESCRIPTION OF THE INVENTION

Figure 1:
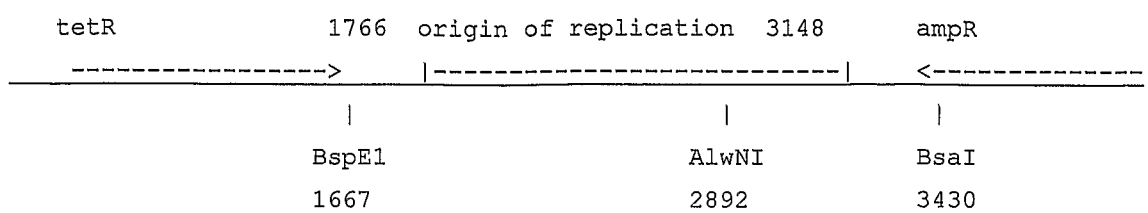
FIG. 1 shows a linear map of the pBR322 origin of replication (nucleotides 1766-3148).

The following definitions are provided in order to aid those skilled in the art in understanding the detailed description of the present invention.

The terms "expression construct" and "recombinant expression construct" and "expression system" will be understood to describe genetically-engineered nucleic acid sequences encoding at a minimum an origin of replication, a selectable marker and a gene or polypeptide-encoding nucleic acid of interest to be expressed in a recipient host cell.

The term "plasmid" or "vector" will be understood to include any extrachromosomal covalently continuous double-stranded nucleic acid molecule.

The term "copy number" is the number of molecules of a particular type of plasmid on or in a cell or part of a cell. This will be understood to describe a characteristic of a recombinant expression construct present in a host cell in greater than a single copy per cell. Most plasmids are classified by the terms "multiple copy number," "low copy number" or "high copy number," which describes the ratio of plasmid/chromosome molecules.

The term "regulatable promoter" is intended to encompass DNA sequences that mediate transcription of a nucleic acid in a cell. Regulatable promoters are distinguished from promoters that are not regulatable in that regulatable promoters are operatively linked to "cis-acting transcription control elements" that will be understood to be nucleic acid sequences that regulate or control transcription of a polypeptide-encoding nucleic acid. As used herein, the term "cis-acting transcription control element" is particularly directed to nucleic acid sequences that make said regulatable promoter "inducible," as that term is defined herein below. Said regulatable promoters of the invention comprising said cis-acting transcription control elements are operatively-linked to polypeptide-encoding nucleic acids and control transcription thereof in a cell, most preferably a bacterial cell, and more preferably an *E. coli* cell, into which a recombinant expression construct of the invention has been introduced. Most preferably, the transcription control of the regulatable promoters of the invention is mediated by interaction between the cis-acting transcription control elements with the trans-acting transcription factors encoded by the recombinant expression constructs of the invention. Regulatable promoters such as the bacteriophage lambda $P_L$ promoter, the promoters of the lac operon, the trp operon, and the ara operon, as well as some of their derivatives, have been widely used to control gene expression. Another family of regulatable promoters is the synthetic cpex promoter series (described in Bogosian et al., U.S. Pat. No. 6,617,130, which is hereby incorporated by reference in its entirety), which is induced by nalidixic acid.

The term "operatively linked" is intended to describe the linkage between nucleic acids wherein the position and proximity of the linkage ensures coupled replication and is sufficient and appropriate to be recognized by trans-acting transcription factors and other cellular factors whereby polypeptide-encoding nucleic acid is efficiently expressed under appropriate conditions.

The term "origin of replication" or "ORI" as used herein is intended to encompass regions of nucleotides that are necessary for replication of a plasmid. Some of examples of origins of replication: nucleotides 1766-3148 of pBR322; nucleotides 1667-2892 of ColE1; and nucleotides 580-1407 of pACYC184.

The terms "hybrid" or "chimeric" will be understood to mean any plasmid containing nucleotide sequences from two or more plasmids.

The terms "hybrid origin of replication" or "chimeric origin of replication" as used herein are intended to encompass nucleotide sequences from a first plasmid's origin of replication combined or linked with nucleotide sequences from a second plasmid's origin of replication in order to create a region of nucleotides that allows for the replication of a plasmid. Some examples of plasmids containing hybrid origin of replications are: pXT975 and pXT976.

The term "restriction enzyme" will be understood to mean any of a group of enzymes, produced by bacteria, which cleave molecules of DNA internally at specific base sequences. Examples of restriction enzymes would include: BspEI; BglII; NsiI; NotI; SacI; SpeI; and AlwNI The term "restriction site" will be understood to mean a sequence of bases in a DNA molecule that is recognized by a restriction enzyme.

The term "multiple cloning sites" will be understood to mean a region of nucleotides containing more than one restriction site. Examples of nucleotides sequences containing multiple cloning sites would include: SEQ ID 14; SEQ ID 15; SEQ ID 19; and SEQ ID 20.

The term "PCR amplicon" will be understood to mean amplification products of a polymerase chain reaction (PCR).

For the purposes of this invention, with regard to polypeptide expression, the terms "elevated" or "elevated expression" or "over expression" are intended to indicate that the amount of the polypeptide produced in a cell, preferably a bacterial cell and more preferably an *E. coli* cell transformed with at least one of the recombinant expression constructs of the invention, is higher, more preferably much higher, than the amount of the polypeptide produced either natively or using other recombinant expression constructs. For endogenously produced polypeptides, the term is intended to mean increased expression compared with endogenous expression levels. For heterologous polypeptides, the term is intended to reflect increased production of said heterologous polypeptides associated with conventional recombinant or genetic engineering-related expression vectors, systems and methods.

The present invention provides nucleic acids, recombinant expression constructs, bacterial cells, reagents and methods for regulating bacterial gene expression, for over expression of desired or target polypeptides in bacteria.

Hybrid origins of replication comprising nucleotide sequences from an origin of replication from at least two different plasmids can be created. Sequences from pBR322, pACYC184, p15A, MB1 or ColE1 can be combined to create a hybrid origin of replication. Plasmids can also be modified to contain a portable hybrid origin of replication. Depending on the needs of the user, different regions of different origin of replications could be used in order to tailor the characteristics of the origin of replication to suit the user's needs. For some embodiments of the present invention, at least 200 nucleotides, more preferably 250 nucleotides, from a one origin of replication is linked to nucleotides from a different origin of replication.

Plasmids can also be modified to contain a portable hybrid origin of replication. A hybrid origin of replication is created that is flanked by multiple unique restriction sites known as multiple cloning sites (MCS). With the MCS on each side of the origin of replication, the hybrid origin of replication is easily exchangeable or portable. Such modified plasmids will provide useful cloning tools that allow for regulation of the level of expression of desired or target gene products because the copy number of a plasmid could be controlled.

The present invention encompasses a number of modified plasmids that were created by modifying the pBR322 plasmid. One of these modified pBR322 plasmids, the pXT995 plasmid, has the standard pMB1 origin of replication region normally present on pBR322, flanked by multiple unique restriction sites (a multiple cloning site, or MCS). Another modified pBR322 plasmid of the present invention, pXT988, has had the pMB1 origin of replication replaced with the ColE1 origin. It also has the desirable feature of having the origin region flanked by MCS. The pXT995 and pXT988 plasmids of the present invention allow for easy replacement of the origin of replication with nearly any desired origin of replication. These plasmids also retain the desirable features of the parent pBR322 plasmid.

The pXT995 and pXT988 plasmids will be useful in situations where it is desirable to modify the plasmid copy number, by exchanging the origin of replication such as when a low copy number is desirable, for over-expressing a gene that is not well-tolerated by the host cell. In other circumstances, however, it may be desirable to have a high copy number plasmid, such as when purifying an over-expressed protein. Additionally, it may be desirable to have a differentially regulatable origin of replication. All of these options or adaptations are available by using the modified plasmids pXT995 or pXT988 of the present invention or creating other customized plasmids based on the disclosure of the present invention.

The following examples are included to demonstrate preferred embodiments of the invention. It should be appreciated by those of skill in the art that the techniques disclosed in the examples which follow represent techniques discovered by the Inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Culture Procedures

Bacteria were routinely cultured in Luria-Bertani (LB) medium or LB agar supplemented as appropriate with ampicillin (100 μg/ml), chloramphenicol (25 μg/ml), tetracycline (10 μg/ml), kanamycin (25 μg/ml), streptomycin (25 μg/ml), or spectinomycin (25 μg/ml).

DNA Procedures.

Plasmid DNA was isolated using an alkaline lysis method and purified if necessary using a Qiaprep Spin Miniprep (Qiagen). Polymerase chain reaction (PCR) was done in a Roche GeneAmp PCR System 2700, using the Roche PCR Master Kit. Custom primers were synthesized by InVitrogen. Restriction digestions were carried out according to the enzyme manufacturers' instructions for each restriction endonuclease. For isolation of DNA fragments, the fragments were separated on 0.9% (wt/vol) agarose gels and isolated using a Qiaquick Gel Extraction Kit (Qiagen). Roche T4 DNA Ligase was used for DNA ligations. Plasmid transformations were carried out in a BioRad Micropulser, using InVitrogen ElectoMax DH5α competent cells. For nucleotide sequencing, automated sequencing was carried out using an ABI Prism 3730XL DNA sequencer (PE Biosystems) and Big Dye terminator mixes:

The present invention involves genetically modifying the origin of replication region of pBR322 (pMB1) from coordinates 1766-3148 and to create an exchangeable origin of replication region flanked by unique restriction sites (e.g. multiple cloning sites, MCS). The technique of "splicing by overlap extension" (SOE) was utilized to create the modified pBR322 constructs of the present invention; however, other suitable methods could also be utilized. These SOE methods are well known and are described by Horton et al. in *Gene*, 77: 61-68 (1989), which is hereby incorporated by reference in its entirety.

The plasmid pBR322 has a copy number of about 20-30, a number determined in part by its pMB1 origin of replication. An aspect of the present invention involves replacing the pMB1 origin of replication region of pBR322 with a number of different origin constructs, including creating several hybrid plasmids such as pXT975, pXT976, pXT1000, and pXT1001, which have a modified origin of replication region. These plasmids contain a hybrid origin of replication comprising of pMB1 origin of replication nucleotide sequences and ColE1 origin of replication nucleotide sequences.

Since ColE1 has been one of the standard plasmids utilized in many of the traditional experiments on plasmid origins of replication, the construction of a modified pBR322-based plasmid that has its origin of replication region replaced with the ColE1 origin of replication region provides a very useful tool for cloning and expression constructs, as well as for future origin of replication experiments. Thus, another aspect of the present invention involves creating a modified pBR322 construct in which the entire origin of replication has been replaced with a corresponding origin from ColE1, and is also flanked by multiple cloning sites (MCS).

When an origin of replication is flanked by MCS, it results in an origin of replication region that is easily exchangeable with other desired origins of replication. An example of this type of modified construct includes plasmid pXT988. The plasmid pXT988 serves as a template from which to create any desired, pBR322-based plasmid construct having any desired origin of replication, since it has an easily replaceable origin cassette flanked by multiple cloning sites. A related plasmid of the present invention, pXT995, has the unmodified pBR322 (pMB1) origin of replication flanked by MCS, also facilitating the replacement of the origin with any origin of replication that has desired features such as a lower copy number, a higher copy number, or other desirable feature.

In the design of these various plasmid modifications, the pMB1 origin of replication region on pBR322 was replaced in stages, with varying amounts of the ColE1 origin of replication region. A map showing the unique restriction sites on pBR322 is shown in FIG. 1. Two MCS's, the BglII-NsiI-NotI fragment with the SEQ ID NO: 30; AGATCTATGCATGCG-GCCGC; and the SacI-SpeI-BglII fragment with SEQ ID NO: 31; GAGCTCACTAGTAGATCT were used for constructing some of the desired modified plasmids.

The initial splicing by overlap extension (SOE) manipulations use two existing unique restriction sites on pBR322 that are located outside of the 1766-3148 origin of replication region. At this stage of the plasmid manipulations it did not matter that these sites were some distance outside the origin of replication region. The restriction sites used were BspEI at coordinate 1667, and BsaI at coordinate 3430. A third site was used to facilitate the SOE work, the unique AlwNI site within the origin of replication region at coordinate 2892. This AlwNI site is also present at the same relative position within the ColE1 origin of replication.

Example 1

Construction of pXT975

Primers were used to amplify by PCR the region on pBR322 from about coordinate 3149 within the origin of replication region to about coordinate 3500, past the BsaI site at coordinate 3430, as shown in FIG. 2. The nucleotide sequence of pBR322 is described in SEQ ID NO: 1. The nucleotide sequence given here is different from that found in Genbank, as more recent nucleotide sequencing of the plasmid pBR322 by the inventors has shown differences with the Genbank nucleotide sequence; the nucleotide sequence given here is believed by the inventors to be the correct nucleotide sequence of pBR322.

The following primers were utilized for these initial amplification steps:

```
SEQ ID NO:2:
5'-GCTCGGCCCTTCCGGCTGGC-3'

SEQ ID NO:3:
5'-TTACGCGCAGAAAAAAAGGATCTCAAGAAGATCCTTTAATCTTTTCT

ACGGGGTCTGACGCTCAGTGGAACGAAAACTCACGTTAAGGGATTTTGGT

C-3'
```

The primer for the region at coordinate 3149 (SEQ ID NO:3) included a long tail matching the corresponding region of the ColE1 origin of replication.

The resulting 399 base pair PCR fragment was used as the source of a 399 base pair primer (SEQ ID NO:4),

```
  1 GCTCGGCCCT TCCGGCTGGC TGGTTTATTG CTGATAAATC TGGAGCCGGT

51 GAGCGTGGGT CTCGCGGTAT CATTGCAGCA CTGGGGCCAG ATGGTAAGCC

101 CTCCCGTATC GTAGTTATCT ACACGACGGG GAGTCAGGCA ACTATGGATG

151 AACGAAATAG ACAGATCGCT GAGATAGGTG CCTCACTGAT TAAGCATTGG

201 TAACTGTCAG ACCAAGTTTA CTCATATATA CTTTAGATTG ATTTAAAACT

251 TCATTTTTAA TTTAAAAGGA TCTAGGTGAA GATCCTTTTT GATAATCTCA
```

```
301 TGACCAAAAT CCCTTAACGT GAGTTTTCGT TCCACTGAGC GTCAGACCCC

351 GTAGAAAAGA TTAAAGGATC TTCTTGAGAT CCTTTTTTTC TGCGCGTAA
``` along with a second, regular primer matching the plasmid ColE1 origin of replication just upstream of the AlwNI site (SEQ ID NO:5 5'-CCTTCTAGTGTAGCCG-TAGTCGGGCC-3'), to generate a PCR fragment from ColE1 plasmid DNA.

The nucleotide sequence of plasmid ColE1 is described in SEQ ID NO:6. The nucleotide sequence given here is different from that found in Genbank, as more recent nucleotide sequencing of the plasmid ColE1 by the inventors has shown differences with the Genbank nucleotide sequence; the nucleotide sequence given here is believed by the inventors to be the correct nucleotide sequence of ColE1. The resulting PCR fragment was digested with the restriction endonucleases AlwNI and BsaI to yield a fragment that was inserted into pBR322, yielding plasmid pXT975, which has the region from the AlwNI site at coordinate 2892 to the end of the pBR322 origin of replication region at coordinate 3148, replaced by the corresponding region of the ColE1 origin of replication. The nucleotide sequence of pXT975 is described in SEQ ID NO:7.

Example 2

Construction of pXT976

Primers were used to amplify by PCR the region on pBR322 from just before the BspEI site at coordinate 1667 to coordinate 1766 as shown in FIG. 3. The following primers were utilized for these initial amplification steps:

```
(SEQ ID NO:8
5'-GCGACCTGAGCAACAACATGAATGG-3')

(SEQ ID NO:9
5'-TTACTTGAACGCTGTGAGGGTAAACAACTGGCGGTATGGATGCGGCG

GGACCAGAGAAAAATCACTCAGGGTCAATGCCAGCGCTTCGTTAATACAG

ATG-3')
```

The primer for the region at coordinate 1765 (SEQ ID NO:9) included a long tail matching the corresponding region of the ColE1 origin of replication.

The resulting 236 base pair PCR fragment was used as the source of a 236 base pair primer (SEQ ID NO:10),

```
1
GCGACCTGAGCAACAACATGAATGGTCTTCGGTTTCCGTGTTTCGTAAAG

51
TCTGGAAACGCGGAAGTCAGCGCCCTGCACCATTATGTTCCGGATCTGCA

101
TCGCAGGATGCTGCTGGCTACCCTGTGGAACACCTACATCTGTATTAACG

151
AAGCGCTGGCATTGACCCTGAGTGATTTTTCTCTGGTCCCGCCGCATCCA

201
TACCGCCAGTTGTTTACCCTCACAGCGTTCAAGTAA
``` along with a second, regular primer matching the ColE1 origin of replication just past the AlwNI site (SEQ ID NO:11

5'-GCCCGACCGCTGCGCCTTATCCGG-3'), to generate a PCR fragment from ColE1 plasmid DNA.

The resulting PCR fragment was digested with BspEI and AlwNI and inserted into pBR322 as shown in FIG. 3C. This yielded plasmid pXT976, which has the region from the end of the pBR322 origin of replication at coordinate 1766 to the AlwNI site at coordinate 2892 replaced by the corresponding region from the ColE1 origin of replication. The nucleotide sequence corresponding to pXT976 is described in SEQ ID NO: 12.

Example 3

Construction of pXT977

The final two PCR fragments as described above for the construction of pXT975 and pXT976, were cut with AlwNI, ligated together, and then amplified with PCR primers matching the tail regions (SEQ ID NO:2, and SEQ ID NO:8, shown above) outside the BspEI and BsaI sites.

The resulting PCR fragment was digested with BspEI and BsaI and inserted into pBR322. This yielded plasmid pXT977, which has the pBR322 origin of replication region from coordinates 1766 to 3148 replaced with the corresponding region from the ColE1 origin of replication. The nucleotide sequence of pXT977 is described as SEQ ID NO: 13.

Example 4

Comparative Maps of the Origin of Replication Regions of pBR322, pXT975, pXT976, and pXT977

The construction of the three plasmids described in Examples 1-3 yielded modified pBR322-based plasmids containing the following homogenous (one source) or hybrid/chimeric origin of replication regions as shown in FIG. 4:

pBR322: origin of replication region from 1766-3148 from pMB1 (homogeneous origin of replication);
pXT975: origin of replication region from 1766 to AlwNI from pMB1, and from AlwNI to 3148 from ColE1 (hybrid origin of replication);
pXT976: origin of replication region from 1766 to AlwNI from ColE1, and from AlwNI to 3148 from pMB1 (hybrid origin of replication);
pXT977: origin of replication region from 1766-3148 from ColE1 (homogeneous origin of replication).

Example 5

Experimentally Determined Plasmid Copy Numbers for pBR322, and Modified pBR322-Based Plasmids pXT975, pXT976, and pXT977

The copy numbers for plasmids pBR322, pXT975, pXT976, and pXT977 were determined in strain LBB427, which is the standard wild-type E. coli K-12 strain W3110 with a mutation inactivating the fhuA gene. The copy number measurements were made on two sets of shake flask cultures grown in L-broth plus ampicillin (100 micrograms per milliliter). At each copy number measurement time point, a sample of the culture was diluted and plated on L-broth agar plates containing ampicillin (100 micrograms per milliliter) in order to get a count of plasmid-containing cells per milliliter of culture. From this same sample of the culture, plasmid DNA was isolated and quantified. Plasmid DNA quantification was performed by linearization of the plasmid with a restriction enzyme that cut the plasmid molecule at only one site, running the linearized plasmid DNA on a polyacrylamide gel along, staining the gel with ethidium bromide, and performing scanning densitometry on the stained plasmid DNA band. The resultant densitometric scan reading was compared to the densitometric scan readings obtained from known amounts of a plasmid DNA standard to determine the amount of plasmid DNA per milliliter of culture. This amount was converted to molecules of plasmid DNA per milliliter of culture, and then divided by the number of cells per milliliter of culture to yield the plasmid copy number in terms of molecules of plasmid DNA per cell. Table 1 shows the results of this experiment; at each time point, two plasmid copy numbers are given, showing the results from the duplicate cultures that were assayed.

TABLE 1

Plasmid copy number during growth in shake flasks containing L-broth medium plus ampicillin and tetracycline

| Plasmid | (hours after inoculation) 7.5 hrs |
|---|---|
| pBR322 | 32, 34 |
| pXT975 | 8, 8 |
| pXT976 | 17, 23 |
| pXT977 | 6, 9 |

The above results indicate that plasmid copy number, when compared to that of pBR322 with its pMB1 origin (and also to pXT976 that has a complete pMB1 origin), is reduced when the origin of replication region from coordinate 2892 (the AlwNI site) to position 3148 is replaced with the corresponding region from ColE1 (as on plasmids pXT975 and pXT977). These results illustrate the utility of the present invention in providing new plasmid vectors with two ranges of plasmid copy numbers, namely plasmids pXT975 and pXT977 with plasmid copy numbers of about 10, and plasmid pXT976 with a plasmid copy number of about 20.

Example 6

Construction of pXT988, a Modified pBR322 Plasmid Containing the ColE1 Origin of Replication Region Flanked by Multiple Cloning Sites Creating a Replaceable Origin of Replication Region To construct a plasmid with the origin of replication region flanked by multiple cloning sites, the SOE constructions using the initial primers containing the long ColE1 tails described in Examples 1-4 were repeated, but these primers were changed slightly to include multiple cloning sites at the junction between pBR322 and ColE1 nucleotide sequences as shown in FIG. 5. The primer (SEQ ID NO:14):

5'-GCTGTGAGGGTAAACAACTGGCGGTATGGATGCGGCGGGGCGGCCGC

ATGCATAGATCTACCAGAGAAAAATCACTCAGGGTCAATGCCAGCGCTTC

GTT-3' was substituted for the primer SEQ ID NO:9, and the primer (SEQ ID NO:15):

5'-AGAAAAAAAGGATCTCAAGAAGATCCTTTAATCTTTTCTACGAGCTC

ACTAGTAGATCTGGGGTCTGACGCTCAGTGGAACGAAAACTCACGTTAAG

GGA-3' was substituted for the primer SEQ ID NO:3.

The nucleotide sequence of the multiple cloning site (MCS) included on the primer SEQ ID NO:14 included recognition sites for the restriction endonucleases BglII (AGATCT), NsiI (ATGCAT), and NotI (GCGGCCGC).

The nucleotide sequence of the multiple cloning site (MCS) included on the primer SEQ ID NO: 15 included recognition sites for the restriction endonucleases SacI (GAGCTC), SpeI (ACTAGT), and BglII (AGATCT).

Preparation of the BsaI-AlwNI fragment with a multiple cloning site is shown in FIGS. 5A and 5B. The primers SEQ ID NO:2 and SEQ ID NO:15 were used to generate a 409 base pair PCR fragment. This PCR fragment was used as the source of a 409 base pair primer (SEQ ID NO:16),

```
  1
GCTCGGCCCTTCCGGCTGGCTGGTTTATTGCTGATAAATCTGGAGCCGGT
 51
GAGCGTGGGTCTCGCGGTATCATTGCAGCACTGGGGCCAGATGGTAAGCC
101
CTCCCGTATCGTAGTTATCTACACGACGGGGAGTCAGGCAACTATGGATG
151
AACGAAATAGACAGATCGCTGAGATAGGTGCCTCACTGATTAAGCATTGG
201
TAACTGTCAGACCAAGTTTACTCATATATACTTTAGATTGATTTAAAACT
251
TCATTTTTAATTTAAAAGGATCTAGGTGAAGATCCTTTTTGATAATCTCA
301
TGACCAAAATCCCTTAACGTGAGTTTTCGTTCCACTGAGCGTCAGACCCC
351
AGATCTACTAGTGAGCTCGTAGAAAAGATTAAAGGATCTTCTTGAGATCC
401
TTTTTTTCT
``` that was used along with a second, regular primer matching the ColE1 origin of replication just upstream of the AlwNI site (SEQ ID NO:5), to generate a PCR fragment from ColE1 plasmid DNA.

Figure 5D:
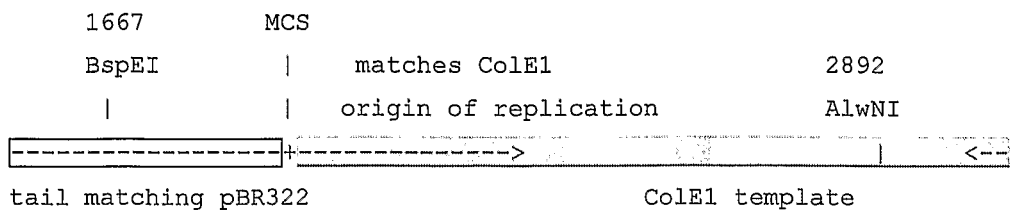
FIG. 5 shows the construction of pXT988, a modified pBR322 construct with the ColE1 origin of replication region flanked by multiple cloning sites (MCS). In panel 5A, the design of one of the primers used to create the modified plasmid is shown with a region at coordinate 3430 that is homologous to pBR322 and a long tail region containing sequences of multiple restriction enzyme recognition sites and a region of sequences that is homologous to the ColE1 origin of replication. In panel 5B, the design of a second primer is shown with a region at coordinate 2892 that is homologous to the ColE1 origin of replication and a tail region containing sequences of multiple restriction enzyme recognition sites and a region of sequences that is homologous to the pBR322 plasmid at coordinate 3430. In panel 5C, the design of a second primer is shown with a region at coordinate 1667 that is homologous to the pBR322 origin of replication and a tail region containing sequences of multiple restriction enzyme recognition sites and a region of sequences that is homologous to the ColE1 plasmid. In panel 5D, the design of a second primer is shown with a region at coordinate 2892 that is homologous to the ColE1 origin of replication and a tail region containing sequences of multiple restriction enzyme recognition sites and a region of sequences that is homologous to the pBR322 plasmid at coordinate 1667. Panel 5E shows the modified pBR322 construct, pXT988, which contains the entire ColE1 origin of replication, flanked by MCS.

Preparation of the AlwNI-BspEI fragment with a multiple cloning site is shown in FIGS. 5C and 5D. The primers SEQ ID NO:8 and SEQ ID NO:14 were used to generate a 246 base pair PCR fragment. This PCR fragment was used as the source of a 246 base pair primer (SEQ ID NO:17),

```
  1
GCGACCTGAGCAACAACATGAATGGTGTTCGGTTTCCGTGTTTCGTAAAG
 51
TCTGGAAACGCGGAAGTCAGCGCCCTGCACCATTATGTTCCGGATCTGCA
101
TCGCAGGATGCTGCTGGCTACCCTGTGGAACACCTACATCTGTATTAACG
151
AAGCGCTGGCATTGACCCTGAGTGATTTTCTCTGGTAGATCTATGCATG
201
CGGCCGCCCCGCCGCATCCATACCGCCAGTTGTTTACCCTCACAGC
``` that was used along with a second, regular primer matching the ColE1 origin of replication just past the AlwNI site (SEQ ID NO:11), to generate a PCR fragment from ColE1 plasmid DNA.

The final two PCR fragments made as described above were cut with AlwNI, ligated together, and then amplified with PCR primers matching the tail regions outside the BspEI and BsaI sites (SEQ ID NO:2 and SEQ ID NO:8). The resulting PCR fragment was digested with BspEI and BsaI and inserted into pBR322.

Figure 5E:
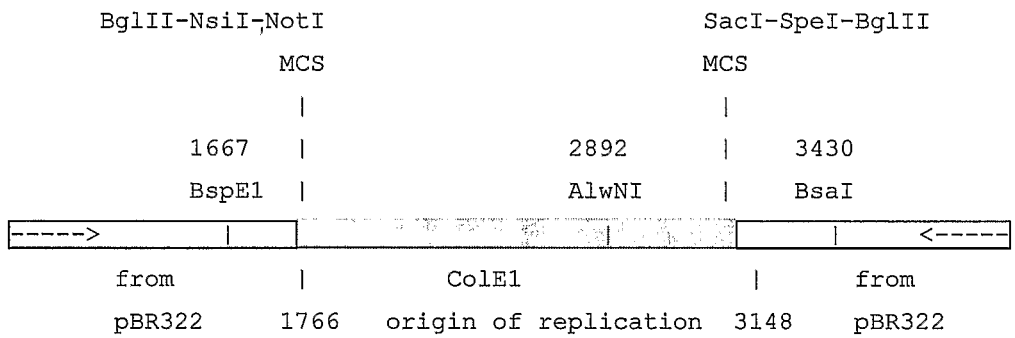

The resulting plasmid is pXT988, as shown in FIG. 5E, has the pBR322 (pMB1) origin of replication region from coordinates 1766 to 3148 replaced by the corresponding region from the ColE1 origin of replication, and also has the ColE1 origin of replication region flanked by multiple cloning sites, creating a replaceable ColE1 origin of replication region. The restriction sites in the two multiple cloning sites are also shown in the FIG. 5E. The nucleotide sequence of pXT988 is described as SEQ ID NO:18.

Example 7

Construction of pXT995, a Modified pBR322 Plasmid with the pMB1 Origin of Replication Region Flanked by Multiple Cloning Sites The construction of plasmid pXT988, which is a modified pBR322-based plasmid with the pMB1 origin of replication region replaced by the ColE1 origin of replication region, and flanked by multiple cloning sites, provides for the quick and easy replacement of this origin of replication with any desired alternative origin of replication. Since pXT988 has the ColE1 origin of replication region, the obvious first choice in demonstrating the utility of this new tool was to replace the ColE1 origin of replication region with the pBR322 (pMB1) origin of replication region.

The first step to exchange the pMB1 origin of replication for the ColE1 origin of replication was to use primers located just inside where the multiple cloning sites were located, to amplify the pMB1 origin of replication region of pBR322. The primers included tails with the same multiple cloning sites, and are given as

```
                                           SEQ ID NO:19
5'-AGGAAGATCTATGCATGCGGCCGCCCCGCCGCATCCATACCGCCAGT

TG-3'
and
                                           SEQ ID NO:20
5'-AGGAAGATCTACTAGTGAGCTCGTAGAAAAGATCAAAGGATCTTCTT

G-3'
```

The nucleotide sequence of the multiple cloning site (MCS) included on the primer SEQ ID NO:19 included recognition sites for the restriction endonucleases BglII (AGATCT), NsiI (ATGCAT), and NotI (GCGGCCGC). The nucleotide sequence of the multiple cloning site (MCS) included on the primer SEQ ID NO:20 included with recognition sites for the restriction endonucleases SacI (GAGCTC), SpeI (ACTAGT), and BglII (AGATCT).

Figure 6A:
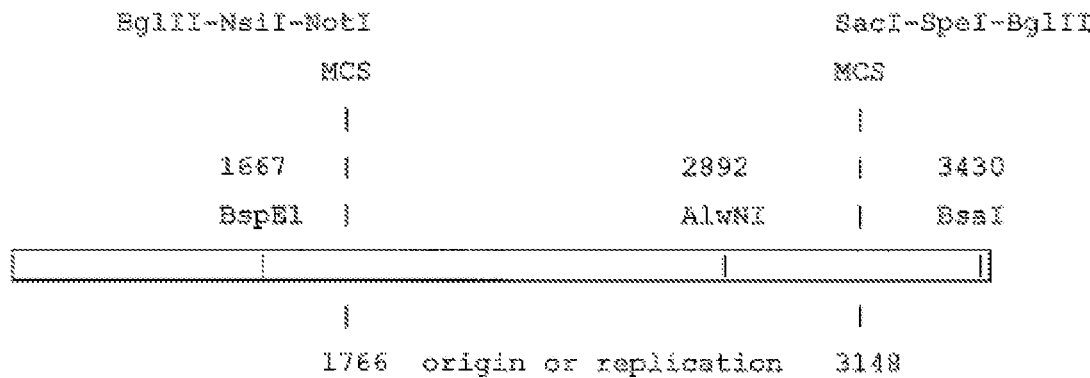
FIG. 6 shows features of plasmids with the origin of replication regions flanked by multiple cloning sites (MCS). Shown in panel 6A is the plasmids pXT995, where the origin of replication is entirely from pBR322 and is flanked by MCS. Panel 6B shows hybrid plasmid pXT1001, where the origin of replication contains segments from both the ColE1 and the pBR322 (pMB1) origins of replications and is flanked by MCS. Panel 6C shows hybrid plasmid pXT1000, where the origin of replication contains segments from both the ColE1 and the pBR322 (pMB1) origins of replications and is flanked by MCS. Panel 6D shows hybrid plasmid pXT988, where the origin of replication is entirely from ColE1, and is flanked by MCS.

The resulting PCR fragment was digested with NotI and SpeI, and used to replace the ColE1 origin of replication region on pXT988 to yield the plasmid pXT995, as shown in FIG. 6A. Plasmid pXT995 has the pBR322 (pMB1) origin of replication region and also has the flanking multiple cloning sites, creating a pMB1 origin cassette. The nucleotide sequence for plasmid pXT995 is described in SEQ ID NO:21.

Example 8

Figure 6B:
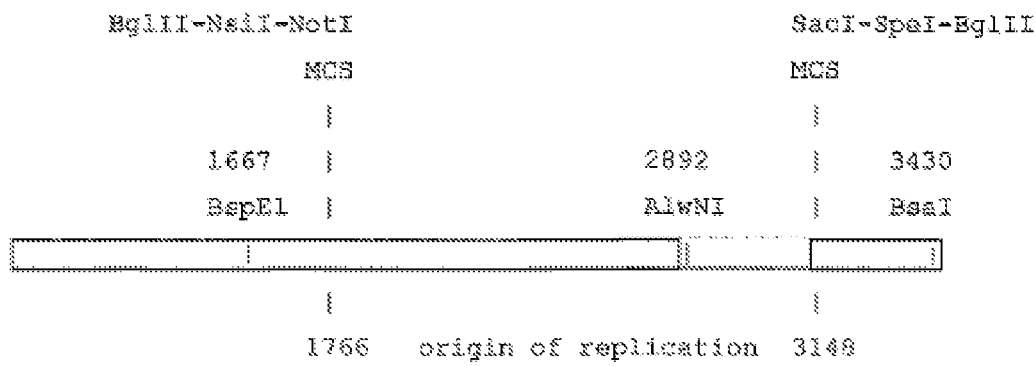
Figure 6C:
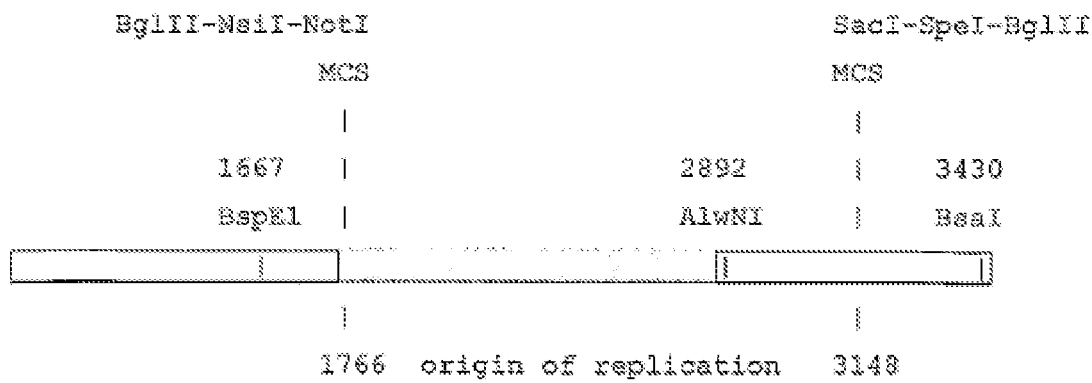

Construction of pXT1000, a Modified pBR322 Plasmid with a Hybrid Origin of Replication Flanked by MCS The plasmid pXT1000 was constructed by inserting the AlwNI-SpeI fragment from pXT996 (this fragment carries the origin of replication region of pBR322 from the AlwNI site to the MCS) into pXT988. This yielded a plasmid with a composite or hybrid origin of replication, with the region of the origin of replication from the MCS to the AlwNI site being from the ColE1 ORI, and the region of the origin of replication from the AlwNI site to the MCS being from the pMB1 ORI. The resulting plasmid is shown in FIG. 6C. The nucleotide sequence for plasmid pXT1000 is described in SEQ ID NO:22.

Example 9

Figure 6D:
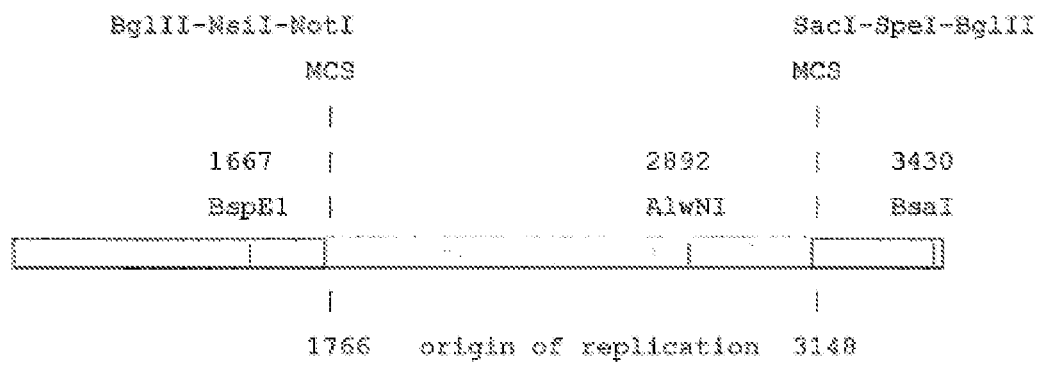

Construction of pXT1001, with a Composite Origin of Replication Flanked by MCS; ColE1 from AlwNI to the MCS The plasmid pXT1001 was constructed by inserting the NsiI-AlwNI fragment from pXT996 (this fragment is the pMB1 origin of replication region from the MCS to the AlwNI site) into pXT988. This yielded a plasmid with a composite or hybrid origin of replication, with the region of the origin of replication from the MCS to the AlwNI site being from the pMB1 ori, and the region of the origin of replication from the AlwNI site to the MCS being from the ColE1 ORI. The hybrid plasmid pXT1001 is shown in FIG. 6B and pXT988 is shown in FIG. 6D. The nucleotide sequence of plasmid pXT1001 is given as SEQ ID NO:23.

The construction of the pXT995, pXT1001, pXT1000, and pXT988 plasmids described above yielded plasmids containing the following homogeneous or hybrid/composite origin of replications, all flanked by MCS:

pXT995: origin of replication region from 1766-3148 from pBR322, flanked by MCS (homogeneous origin of replication);

pXT1001: origin of replication region from 1766 to AlwNI from pBR322, and from AlwNI to 3148 from ColE1, flanked by MCS (hybrid/chimeric origin of replication);

pXT1000: origin of replication region from 1766 to AlwNI from ColE1, and from AlwNI to 3148 from pBR322, flanked by MCS (hybrid/chimeric origin of replication);

pXT988: origin of replication region from 1766-3148 from ColE1, flanked by MCS (homogeneous origin of replication).

Table 3 details the plasmid constructs with novel origin of replications.

TABLE 3

Plasmid constructs with novel origins of replication

| Cloning Vector | Origin Of Replication (ORI) | Plasmid SEQ ID No. |
|---|---|---|
| pBR322 | origin of replication region (positions 1766-3148) taken from pBR322 (pMB1) | 1 |
| pXT995 | origin of replication region (positions 1766-3148) taken from pBR322 (pMB1), flanked by MCS | 21 |
| pXT975 | hybrid origin of replication region with one part of the region (position 1766 to AlwNI restriction site) taken from pBR322, and the other part of the region (from AlwNI restriction site to position 3148) taken from ColE1 | 7 |
| pXT1001 | hybrid origin of replication region with one part of the region (position 1766 to AlwNI restriction site) taken from pBR322, and the other part of the region (from AlwNI restriction site to position 3148) taken from ColE1, flanked by MCS | 23 |
| pXT976 | hybrid origin of replication region with one part of the region (position 1766 to AlwNI restriction site) taken from ColE1, and the other part of the region (from AlwNI restriction site to position 3148) taken from pBR322 | 12 |
| pXT1000 | hybrid origin of replication region with one part of the region (position 1766 to AlwNI) from ColE1, and the other part of the region (from AlwNI to 3148) from pBR322, flanked by MCS | 22 |
| pXT977 | origin of replication region (positions 1766-3148) from ColE1 | 13 |
| pXT988 | origin of replication region (positions 1766-3148) from ColE1, flanked by MCS | 18 |
| pXT1092 | inverted origin of replication region (positions 1766-3148) taken from pBR322 (pMB1), flanked by MCS (positions 1766-3148 are inverted compared to SEQ ID NO. 1 | 33 |
| pXT1091 | pACYC184 origin of replication region (BstZ17I-SacI restriction fragment from pXT1094) inserted into pXT995 | 28 |
| pXT1094 | pACYC184 origin of replication region (position 517-1464) inserted into MCS of pXT995 | 27 |
| pXT1109 | pACYC184 origin of replication region plus pBR322 rop gene sequence | 34 |

Example 10

Plasmid Copy Numbers of Plasmids with Homogeneous pMB1 or Hybrid pMB1/ColE1 Origin of Replication Regions, with or without Flanking MCS The copy numbers were determined in strain LBB427, which is the standard wild-type *E. coli* K-12 strain W3110 with a mutation inactivating the fhuA gene. The copy number measurements were made on two sets of shake flask cultures grown in L-broth plus ampicillin (100 micrograms per milliliter). The copy number measurements were made as described above. Table 4 shows the results of this experiment; at each time point, two plasmid copy numbers are given, showing the results from the duplicate cultures that were assayed.

TABLE 4

Plasmid copy number during mid-log phase of growth in shake flasks containing L-broth medium plus ampicillin

| Plasmid | 7.5 hours (hours after inoculation) |
|---|---|
| pBR322 | 32, 34 |
| pXT995 | 30, 34 |
| pXT975 | 8, 8 |
| pXT1001 | 8, 12 |
| pXT976 | 17, 23 |
| pXT1000 | 24, 24 |
| pXT977 | 6, 9 |
| pXT988 | 11, 13 |

The results from these experiments show that creating exchangeable origin of replication cassettes in modified pBR322 plasmids (i.e., the origin of replication region was flanked with MCS) did not alter the copy numbers of the plasmids, when compared with plasmids lacking the MCS. Also, a previously observed trend was observed again: when the origin of replication region from the AlwNI to 3148 is from ColE1 (as on plasmids pXT975, pXT1001, pXT977, and pXT988), the copy number is reduced versus when that same origin of replication region is from pBR322 (as on the plasmids pBR322, pXT995, pXT976, and pXT1000). These results illustrate the utility of the present invention in providing new plasmid vectors with two ranges of plasmid copy numbers, namely plasmids pXT975, pXT977, pXT988, and pXT1001 with plasmid copy numbers of about 10, and plasmids pXT976, pXT995, and pXT1000 with plasmid copy numbers of about 20.

Example 11

Construction of Bovine Somatotropin (bST) Expression Plasmids with Either Homogeneous pMB1, ColE1, or Hybrid pMB1/ColE1 Origins of Replication Bovine somatotropin (bST) is a natural protein produced in the pituitary glands of all cattle and it helps adult cows produce milk. Known in the art are several plasmids that contain the genetic elements necessary for bST protein expression. The bST expression region from one such plasmid, pXT757 (identical to pXT709, described in Bogosian et al., U.S. Pat. No. 6,828,124, which is hereby incorporated by reference in its entirety), was moved into each one of the modified pBR322-based plasmids: pXT975, pXT976, pXT977, pXT988, pXT995, pXT1000, and pXT1001. The plasmid pXT757 contains the synthetic cpex-20 promoter (described in Bogosian et al., U.S. Pat. No. 6,617,130, which is hereby incorporated by reference in its entirety) driving the expression of a synthetic bovine somatotropin (bST) gene. The cpex-20 promoter was designed to be regulated by the LexA repressor protein of the *E. coli* SOS regulon, and as such is inducible by the addition of nalidixic acid. The EcoRI-BamHI fragment of pXT757 (containing the complete bST expression region from pXT757) was inserted into each of plasmids pXT975, pXT976, and pXT977. A similar EcoRI-SalI fragment of pXT757 was inserted into each of plasmids pXT988, pXT995, pXT1000, and pXT1001. These constructions yielded the bST expression plasmids shown in Table 5 below.

sured during culture in a fermenter containing a chemically defined inorganic salts and glucose minimal medium (without any antibiotics), with bST synthesis induced by the addition of 50 ppm nalidixic acid at an optical density at 660 nm of 23. The level of bST expression was measured using an HPLC assay with a limit of detection of 1 milligram of bST per liter. The fermentation growth conditions and the HPLC assay are described in Bogosian et al. 1989; as described in that paper, the fermenter contained a minimal medium without any antibiotics.

An unexpected finding from these experiments was that when the plasmid origin of replication included ColE1-derived origin of replication nucleotide sequences from the

TABLE 5 bST expression plasmids

| Bst Expression Vector | Cloning Vector | Origin Of Replication (ORI) |
|---|---|---|
| pXT757 | pBR322 | origin of replication region (positions 1766-3148) taken from pBR322 (pMB1) |
| pXT996 | pXT995 | origin of replication region (positions 1766-3148) taken from pBR322 (pMB1), flanked by MCS |
| pXT985 | pXT975 | hybrid origin of replication region with one part of the region (position 1766 to AlwNI restriction site) taken from pBR322, and the other part of the region (from AlwNI restriction site to position 3148) taken from ColE1 |
| pXT1003 | pXT1001 | hybrid origin of replication region with one part of the region (position 1766 to AlwNI restriction site) taken from pBR322, and the other part of the region (from AlwNI restriction site to position 3148) taken from ColE1, flanked by MCS |
| pXT986 | pXT976 | hybrid origin of replication region with one part of the region (position 1766 to AlwNI restriction site) taken from ColE1, and the other part of the region (from AlwNI restriction site to position 3148) taken from pBR322 |
| pXT1002 | pXT1000 | hybrid origin of replication region with one part of the region (position 1766 to AlwNI) from ColE1, and the other part of the region (from AlwNI to 3148) from pBR322, flanked by MCS |
| pXT987 | pXT977 | origin of replication region (positions 1766-3148) from ColE1 |
| pXT1004 | pXT988 | origin of replication region (positions 1766-3148) from ColE1, flanked by MCS |

Example 12

Expression of Bovine Somatotropin (bST) from Modified pBR322-Based Plasmids Containing Either Homogeneous pMB1, ColE1, or Hybrid pMB1/ColE1 Origins of Replication The host strain LBB427 was used in experiments to determine the effect of hybrid ORI on the expression level of the protein bST. The level of bST protein expression was mea- AlwNI site to the end of the origin of replication region at coordinate 3148, bST expression was completely abolished. It would not have been predicted that subtle changes in the origin of replication would have such significant effects on the expression of genes elsewhere on the plasmid vector. This finding further illustrates the utility of the present invention, allowing the facile manipulation of plasmid origins of replication for the purpose of testing the effect of such manipulations on heterologous gene expression.

TABLE 6

Quantifying bST protein expression from plasmids containing the bST gene

| plasmid | ORI | bST expression mg per liter |
|---|---|---|
| pXT757 | origin of replication region (positions 1766-3148) taken from pBR322 | 6400 |
| pXT996 | origin of replication region (positions 1766-3148) taken from pBR322, flanked by MCS | 5700 |
| pXT985 | hybrid origin of replication region with one part of the region (position 1766 to AlwNI restriction site) taken from pBR322, and the other part of the region (from AlwNI restriction site to position 3148) taken from ColE1 | no detectable expression |
| pXT1003 | hybrid origin of replication region with one part of the region (position 1766 to AlwNI restriction site) taken from pBR322, and the other part of the region (from AlwNI restriction site to position 3148) taken from ColE1, flanked by MCS | no detectable expression |

TABLE 6-continued

Quantifying bST protein expression from plasmids containing the bST gene

| plasmid | ORI | bST expression mg per liter |
|---|---|---|
| pXT986 | hybrid origin of replication region with one part of the region (position 1766 to AlwNI restriction site) taken from ColE1, and the other part of the region (from AlwNI restriction site to position 3148) taken from pBR322 | 6200 |
| pXT1002 | hybrid origin of replication region with one part of the region (position 1766 to AlwNI) from ColE1, and the other part of the region (from AlwNI to 3148) from pBR322, flanked by MCS | 6200 |
| pXT987 | origin of replication region (positions 1766-3148) from ColE1 | no detectable expression |
| pXT1004 | origin of replication region (positions 1766-3148) from ColE1, flanked by MCS | no detectable expression |

Example 13

Figure 7:
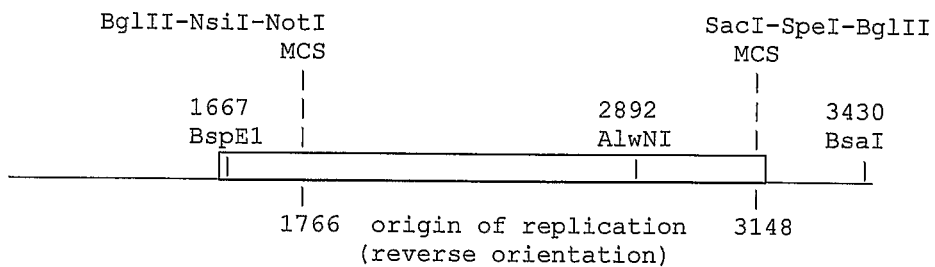
FIG. 7 shows the features of pXT1092, in which the pBR322 (pMB1) origin of replication flanked by multiple cloning sites (MCS) has been flipped into the opposite orientation of that found on pXT995.

Construction of pXT1092, Using pXT995 as Template for Inverting the pBR322 Origin of Replication Region with Flanking MCS Region The plasmid pXT995 is a modified pBR322 with a MCS cassette flanking the position of the origin of replication, as described: BglII-NsiI-NotI, origin of replication, SacI-SpeI-BglII. Inverting or flipping the origin of replication region of pXT995 was accomplished by digestion with BglII, followed by re-ligation. As a result of the re-ligation experiments, eight transformants were obtained and three contained an inverted origin of replication region. One of these transformants was designated pXT1092 (SEQ ID NO: 33) and is shown in FIG. 7.

The plasmid pXT996 is a modified pXT757 with the pBR322 origin of replication flanked by MCS as described: BglII-NsiI-NotI, origin of replication, SacI-SpeI-BglII. Interestingly, numerous attempts to evaluate bST expression of pXT996 with a flipped or inverted origin of replication region by digesting with BglII followed by re-ligation all failed.

These results suggested that flipping or inverting of the origin of replication region could not be done in a plasmid like pXT996 containing the bST expression elements. Thus, it appears that with plasmids containing the bST expression elements, the origin of replication region can only be tolerated in one orientation, i.e., that orientation found on the unmodified pBR322 plasmid. Again, this was an unexpected finding, further illustrating the utility of the present invention with regard to manipulation of the structure and orientation of plasmid origins of replication for the purposes of improving the expression of plasmid-borne heterologous genes.

Example 14

Construction of Plasmids with Origin of Replication Region from pACYC184

The plasmid pACYC184 was derived from the plasmid P15A (Chang and Cohen, 1978). The nucleotide sequence of plasmid pACYC184 is given as SEQ ID NO:24. The copy number of P15A was reported to be about 15 (Cozzarelli et al., 1968), and the copy number of pACYC184 has been variously reported to range from about 18 (Chang and Cohen, 1978), or about 30 (Ray and Skurray, 1984), or about 9 (Atlung et al., 1999). The 4245 base pair plasmid, pACYC184, is compatible with pMB1- or ColE1-related plasmids and can therefore be used together with a pMB1- or ColE1-derivative within the same cell. pACYC184 contains:

(1) the replicon (rep) responsible for the replication of plasmid (this origin of replication is from the plasmid p15A); (2) the tetR gene, encoding tetracycline resistance protein; and (3) the cat gene, encoding for chloramphenicol acetyl transferase and thus conferring resistance to chloramphenicol.

The rop gene encodes a protein that acts to lower the plasmid copy number when compared to plasmids without the rop gene. Therefore, if the rop gene could be added to the ORI of a high copy plasmid, one could alter the copy number of the plasmid inside a cell. The plasmid pACYC184 lacks the rop gene.

Figure 8:
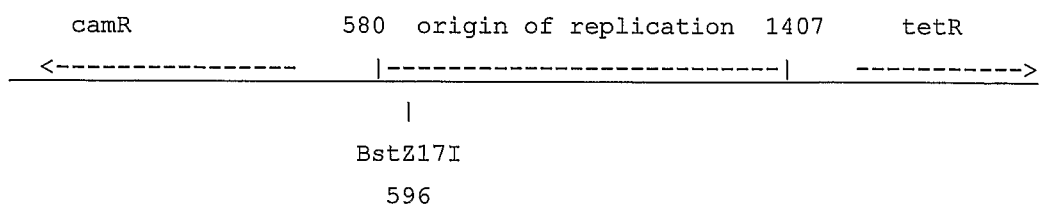
FIG. 8 shows a linear map of the origin of replication region on the plasmid pACYC184 (nucleotides 580-1407) and the single restriction enzyme site at coordinate 596 for the restriction enzyme BstZ17I.

FIG. 8 shows a linear map of the pACYC184 origin of replication containing a single BstZ17I restriction site. As shown in FIG. 9, the nucleotide sequence of pACYC184 (nucleotides 568-1407) reveals an origin of replication region with extensive homology to the origin of replication region on pBR322 (nucleotides 2222-3139). On pBR322, the rop gene lies just counterclockwise of the BstZ17I site, which is at coordinate 2249 on pBR322 and coordinate 596 on pACYC184. The region of homology between these two origins of replication regions begins just prior to this BstZ17I site.

A. Construction of pXT1094, with the pACYC184 Origin of Replication Flanked by MCS.

The pACYC184 origin of replication, from coordinates 517 to 1464 (SEQ ID 24), was amplified as a 948 bp NotI-SacI PCR fragment and inserted into the MCS of pXT995. This yielded pXT1094 (SEQ ID 27), a plasmid with the pBR322 backbone of the bla and tetR genes, but with the pBR322 origin of replication replaced by the pACYC184 origin of replication (the plasmid p15A origin of replication), and flanked by MCS.

The upstream primer (SEQ ID NO:25)

5'-GGCTCAGCAGCGGCCGCGCTGTCCCTCCTGTTCAGCTATTGACGGG G-3' contains a single nucleotide change in the region near the MCS, outside of the region of homology between the pBR322 and pACYC184 origin of replication regions, eliminating the AlwNI site there by changing the site from CAG-CTA-CTG to CAG-CTA-TTG.

The downstream primer (SEQ ID NO:26)

5'-GGCTCTGACGAGCTCGGTGCTACATTTGAAGAGATAAATTGCACTGA AATCTAGG-3' contains a single nucleotide change in the corresponding region near that MCS, eliminating the XbaI site there by changing the site from TCTAGA to CCTAGA. The nucleotide sequence of plasmid pXT1094 is given as SEQ ID NO:27.

B. Construction of pXT1091, a Composite Plasmid with the pACYC184 Origin of Replication and the pBR322 rop Gene, Flanked by MCS.

The pACYC184 origin of replication was excised as a BstZ17I-SacI restriction fragment from pXT1094 and inserted into pXT995, creating pXT1091. The nucleotide sequence of pXT1091 is given as SEQ ID NO:28. It should be noted that on pBR322, the BstZ17I site lies between the rop gene and the origin of replication region. On pACYC184, the BstZ17I site lies in the same relative position with respect to the origin of replication region, in this case just inside the beginning of the region of homology between the two origin of replication regions (as shown in the alignment of FIG. 9 and the pACYC184 origin of replication region shown in FIG. 8). The unmodified pACYC184 does not contain a rop gene. Thus, the new plasmid pXT1091 has the following genetic elements, in clockwise order, the pBR322 tetR gene, the first MCS, the pBR322 rop gene, the BstZ17I site, the pACYC184 origin of replication region, the second MCS, and then the pBR322 bla gene. The nucleotide sequence of plasmid pXT1091 is given as SEQ ID NO:28.

This construct was evaluated to determine whether the pBR322 rop gene product had any effect on the copy number of a plasmid with the pACYC184 origin of replication region (a p15A origin of replication). The copy number results are shown in Table 7 and are described below.

Example 15

Plasmid Copy Numbers of pACYC184, pXT1091, and pXT1094

As an example of the usefulness of the present invention, it can be shown that plasmids modified with hybrid ORI containing the rop gene can have their copy numbers in bacteria altered. The copy numbers for pACYC184, pXT1091, and pXT1094 were determined in strain DH5α, grown in one set of shake flask cultures grown in L-broth plus the appropriate antibiotic, specifically 10 micrograms per milliliter tetracycline for pACYC184, and 100 micrograms per milliliter ampicillin for pXT1091 and pXT1094. The copy number measurements were made as described above. Table 7 shows the results of this experiment.

TABLE 7

Plasmid copy number during growth in shake flasks with L-broth medium (plus tetracycline or ampicillin)

| Plasmid | (hours after inoculation) 7 hours |
|---|---|
| pACYC184 | 85 |
| pXT1091 | 620 |
| pXT1094 | 210 |

These results suggest that the presence of the rop gene, on plasmid pXT1091, actually increased the plasmid copy number rather than lower it (as would have been expected). These findings further illustrate the utility of the present invention with regard to manipulation of the structure plasmid origins of replication for the purposes of improving the expression of plasmid-borne heterologous genes. These results illustrate the utility of the present invention in providing new plasmid vectors with two ranges of plasmid copy numbers, namely plasmid pXT1091 with a plasmid copy number of about 500, and plasmid pXT1094 with a plasmid copy number of about 200.

Example 16

Construction of pXT1110, with the pACYC184 Origin of Replication Flanked by MCS and the pXT757-Derived bST Protein Expression Elements, and pXT1109, with the pACYC184 and Rop Gene Flanked by MCS and the pXT757-Derived bST Protein Expression Elements The NotI-SpeI fragment from pXT1094, carrying the pACYC184 origin of replication flanked by MCS, was inserted into pXT996, thus replacing the pBR322 origin of replication region, and yielding plasmid pXT1110. The NotI-SpeI fragment from pXT1091, carrying the pACYC184 origin of replication and rop gene flanked by MCS, was inserted into pXT996, thus replacing the pBR322 origin of replication region, and yielding plasmid pXT1109 (SEQ ID NO: 34).

Example 17

Expression of bST Protein from Modified pBR322-Based Plasmids Containing Either the pMB1, the pACYC184 Origins of Replication or the pACYC184 Plus rop Origin of Replication As an example of the usefulness of the present invention, it can be shown that plasmids modified with hybrid ORI can alter the level of expression of a target protein. The host strain LBB427 was used in experiments to determine the effect of hybrid ORI on the expression level of the protein bST (bovine somatotrophin). The level of bST protein expression was measured during culture in a fermenter containing a chemically defined inorganic salts and glucose minimal medium (without any antibiotics), with bST protein synthesis induced by the addition of 50 ppm nalidixic acid at an optical density at 660 nm of 23. The level of bST protein expression was measured using an HPLC assay with a limit of detection of 1 milligram of bST per liter. The fermentation growth conditions and the HPLC assay are described in Bogosian et al. 1989; as described in that paper, the fermenter contained a minimal medium without any antibiotics.

TABLE 8

Expression of bST protein from plasmids with the pACYC184 origins of replication or pACYC184 plus rop origin of replication

| plasmid | ori | bST expression mg per liter |
|---|---|---|
| pXT757 | pBR322 (pMB1) | 6400 |
| pXT1109 | pACYC184 plus rop | 2700 |
| pXT1110 | pACYC184 | 4700 |

These results suggest that high plasmid copy numbers have a detrimental effect on this particular bST protein expression system. These findings further illustrate the utility of the present invention with regard to manipulation of the structure plasmid origins of replication for the purposes of improving the expression of plasmid-borne heterologous genes.

Example 18

Construction of Plasmid pXT1007, with a cer Site

The cer protein typically increases the stability of inheritance of a plasmid. Therefore, it may be useful to include the cer gene on a plasmid in order to increase the rate of retention of the plasmid within a cell. The present invention allows for the inclusion of the cer gene in a hybrid ORI, thereby demonstrating the advantage of being able to tailor the ORI of a plasmid to suit one's needs.

The region of ColE1 carrying the cer site, and some flanking nucleotide sequence, was isolated as a 357 bp NsiI-NotI PCR fragment prepared from ColE1 plasmid DNA, and inserted into the MCS on pXT996 to yield the plasmid pXT1007. The nucleotide sequence of the NsiI-NotI fragment was determined, and is shown in FIG. 10 (SEQ ID 32). The nucleotide sequence given in FIG. 10 is different from that found in the Genbank nucleotide sequence of ColE1, as more recent nucleotide sequencing of the plasmid ColE1 by the inventors has shown differences with the Genbank nucleotide sequence; the nucleotide sequence given here is believed by the inventors to be the correct nucleotide sequence of the cer site on the plasmid ColE1. The transcribed region giving rise to the RNA molecule RCD is underlined (Patient and Summers, 1993).

Example 19

Stability of Plasmids pXT757 (No cer Site) and pXT1007 (with a cer Site)

The stability of inheritance of strains LBB427 [pXT757] and LBB427 [pXT1007] were studied by culturing in LB without any antibiotics. The procedure was to start with a fresh overnight culture grown in LB plus ampicillin and tetracycline (where 100% of the cells would contain the plasmid) and sub-culture in LB without any antibiotics. For each sub-culture, 10 microliters of the previous full-density culture were transferred to 10 ml of LB. This is a 1000-fold dilution, requiring the culture to grow for 10 generations to reach full density again. That is, since $2^{10}$=1024, 10 doublings of a 1000-fold diluted culture would be required for the culture to increase about 1000-fold back to full density. Since these *E. coli* strains grow in LB at 37° C. with a doubling time of about 20 minutes, only a little over 3 hours of exponential growth would be required for the 10 doublings. To allow for any lag time, the sub-cultures were grown for at least 8 hours. The practice was to start a subculture in the morning, grow it for 8 hours, then sub-culture again for overnight growth. Thus, the passage of 20 generations was achieved in a 24 hour period. At the end of each ten generation growth cycle, the full density cultures were diluted and plated on LB and LB Amp to determine the percentage of cells that retained the plasmid.

TABLE 9

Percent of cells retaining the plasmid after successive generations

| Generations | pXT757(−cer) | pXT1007 (+cer) |
|---|---|---|
| 0 | 100 | 100 |
| 10 | 89 | 95 |
| 20 | 92 | 100 |
| 30 | 67 | 97 |
| 40 | 33 | 94 |
| 50 | 24 | 100 |
| 60 | 21 | 99 |
| 70 | 3.5 | 95 |
| 80 | 2.2 | 96 |
| 90 | 1.0 | 100 |
| 100 | 0.34 | 91 |

It is apparent that the addition of the cer gene to the pXT757 plasmid has improved the retention rate of the plasmid within the LBB427 cells.

Example 20

Expression of bST from Plasmids with the cer Site

The host strain, LBB427, was used in experiments to determine the effect of hybrid ORI on the expression level of the protein bST. The level of bST protein expression was measured during culture in a fermenter containing a chemically defined inorganic salts and glucose minimal medium (without any antibiotics), with bST protein synthesis induced by the addition of 50 ppm nalidixic acid at an optical density at 660 nm of 23. The level of bST protein expression was measured using an HPLC assay with a limit of detection of 1 milligram of bST per liter. The fermentation growth conditions and the HPLC assay are described in Bogosian et al. 1989; as described in that paper, the fermenter contained a minimal medium without any antibiotics.

TABLE 10

Influence of cer site on bST expression

| Strain and plasmid | fermentation | bST expression mg per liter | |
|---|---|---|---|
| LBB427 [pXT1007] | Run 1 | 6300 | |
| | Run 2 | 6300 | avg. = 6300 |

As shown in Table 6, bST protein expression from pXT757 (lacking the cer site) was about 6400 mg per liter. The results here indicate that addition of the cer site to the origin of replication in pXT757 (thereby creating the plasmid pXT1007) did not lead to increased expression of bST protein. The lack of any beneficial effect of the increased plasmid retention associated with the addition of the cer site may reflect the fact that the fermentation culture was grown for a low number of generations in the absence of antibiotic selection for plasmid retention. Under the fermentation culture conditions used here, the inoculum was grown in L-broth plus antibiotics, and thus 100% of the cells in the inoculum would contain plasmid. However, after inoculation of the fermenter vessel, there were only about 7-8 generations of growth in the fermentation medium in the absence of antibiotics. It would be expected that there would be no detectable loss of plasmid-bearing cells, even without the cer site, in only 7-8 generations. Indeed, as shown in Table 9, pXT757 was retained in over 90% of the cells for at least 20 generations.

Example 21

Figure 11:
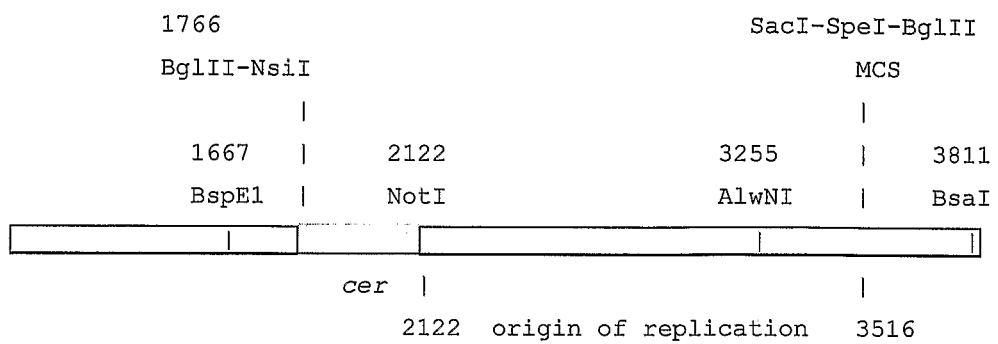
FIG. 11 shows a linear map of the origin of replication region of plasmid pXT1221, containing a cer site.

Construction of pXT1221, a Composite pBR322 Containing a cer Site and Origin of Replication Flanked by MCS The NsiI-SpeI fragment of pXT1007 was inserted into pXT995 (which is pBR322 with the origin of replication flanked by MCS) to yield pXT1221 as shown in FIG. 11. The cer site and pBR322 origin of replication arrangement on pXT1221 with respect to the MCS is:

BglII-NsiI-cer-NotI-pBR322 origin of replication-SacI-SpeI-BglII

The stability of DH5α [pXT1221] was tested as described above for plasmids with and without the cer site, the results shown in Table 11. Remarkably, the plasmid stability was virtually unchanged for greater than 300 generations for constructs containing the cer site.

TABLE 11

Percent of cells retaining the plasmid (+/−cer site) after successive generations

| Generations | pXT757 (−cer) | pXT1007 (+cer) | pXT1221 (+cer) |
|---|---|---|---|
| 0 | 100 | 100 | 100 |
| 10 | 89 | 95 | 100 |
| 20 | 92 | 100 | 100 |
| 30 | 67 | 97 | 100 |
| 40 | 33 | 94 | 100 |
| 50 | 24 | 100 | 100 |
| 60 | 21 | 99 | 85 |
| 70 | 3.5 | 95 | 100 |
| 80 | 2.2 | 96 | 100 |
| 90 | 1.0 | 100 | 100 |
| 100 | 0.34 | 91 | 98 |
| 110 | | | 95 |
| 120 | | | 97 |
| 130 | | | 100 |
| 140 | | | 100 |
| 150 | | | 98 |
| 160 | | | 100 |
| 170 | | | 100 |
| 180 | | | 83 |
| 190 | | | 100 |
| 200 | | | 100 |
| 250 | | | 98 |
| 300 | | | 100 |
| 350 | | | 95 |

This finding indicates that the inclusion of a cer site on a plasmid, an addition made straightforward by the present invention, would be worthy of consideration for culture conditions requiring high plasmid retention for an extended number (greater than 20) of generations of growth in the absence of antibiotic selection.

As the preceding examples have illustrated, the present invention enables the construction of a variety of new types of plasmid vectors with modified origins of replication. The utility of the present invention is partially illustrated by the construction of new plasmid vectors with a wide range of plasmid copy numbers, ranging from 10 to 500 plasmid copies per cell. The utility of the present invention is also illustrated by the ease with which plasmids could be constructed containing the cer site and exhibiting increased plasmid retention during prolonged growth (>20 generations) in the absence of antibiotic selections. Such modified plasmids will also provide useful cloning tools that allow for regulation of the level of expression of desired or target gene products.

Based on the examples in the specification, one should be able to create useful hybrid ORI that can alter the copy number of plasmid. One should also be able to create exchangeable ORI or ORI that can have genetic elements added in order to alter the characteristics of the plasmid. With the aid of the present invention, one should be able to customize a plasmid to suit one's needs.

All of the compositions and/or methods and/or processes and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

REFERENCES

Atlung, T., B. B. Christensen, and F. G. Hansen. 1999. Role of the Rom protein in copy number control of plasmid pBR322 at different growth rates in Escherichia coli K12. Plasmid 41: 110-119.

Blakely, G., G. May, R. McCulloch, L. K. Arciszewska, M. Burke, S. T. Lovett, and D. J. Sherratt. 1993. Two related recombinases are required for site-specific recombination at dif and cer in Escherichia coli K-12. Cell 75: 351-361.

Bogosian, G., B. N. Violand, E. J. Dorward-King, W. E. Workman, P. E. Jung, and J. F. Kane. 1989. Biosynthesis and incorporation into protein of norleucine by Escherichia coli. J. Biol. Chem. 264: 531-539.

Bogosian, G., J. P. O'Neil, and K. C. Terlesky. DNA construct for regulating the expression of a polypeptide coding sequence in a transformed bacterial host cell. U.S. Pat. No. 6,617,130

Bogosian, G., J. P. O'Neil, and N. D. Aardema. Recombinant DNA vectors for expression of somatotropins. U.S. Pat. No. 6,828,124

Bolivar, F., Rodriguez, R. L., Greene, P. J., Betlach, M. C., Heyneker. H, L. and Boyer, H. W. 1977. Construction and characterization of new cloning vehicles. II. A multipurpose cloning system, Gene 2: 95-113.

Chang, A. C., and S, N. Cohen. 1978. Construction and characterization of amplifiable multicopy DNA cloning vehicles derived from the P15A cryptic miniplasmid. J. Bacteriol. 134: 1141-1156.

Colloms, S. D., P. Sykora, G. Szatmari, and D. J. Sherratt. 1990. Recombination at ColE1 cer requires the Escherichia coli xerC gene product, a member of the lambda integrase family of site-specific recombinases. J. Bacteriol. 172: 6973-6980.

Covarrubias, L., Cervantes, L., Covarrubias, A., Soberon, X., Vichido, I., Blanco, A., Kuperstoch-Portnoy, Y. M. and Bolivar, F. 1981. Construction and characterization of new cloning vehicles. V. Mobilization and coding properties of pBR322 and several deletion derivatives including pBR327 and pBR328, Gene 13: 25-35.

Cozzarelli, N. R., R. B. Kelly, and A. Kornberg. 1968. A minute circular DNA from Escherichia coli. Proc. Natl. Acad. Sci. USA 60: 992-999.

Funnell, B. E., and G. J. Phillips 2004. Plasmid biology. American Society for Microbiology Press, Washington, D. C.

Guhathakurta, A., and D. Summers. 1995. Involvement of ArgR and PepA in the pairing of ColE1 dimer resolution sites. Microbiology 141: 1163-1171.

Guhathakurta, A., I. Viney, and D. Summers. 1996. Accessory proteins impose site selectivity during ColE1 dimer resolution. Mol. Microbiol. 20: 613-620.

Hodgman, T. C., H. Griffiths, and D. K. Summers. 1998. Nucleoprotein architecture and ColE1 dimer resolution: a hypothesis. Mol. Microbiol. 29: 545-558.

Horton, R. M., H. D. Hunt, S. N. Ho, J. K. Pullen, and L. R. Pease. 1989. Engineering hybrid genes without the use of restriction enzymes: gene splicing by overlap extension. Gene 77: 61-68.

Patient, M. E., and D. K. Summers. 1993. ColE1 multimer formation triggers inhibition of *Escherichia coli* division. Mol. Microbiol. 9: 1089-1095.

Peden, K. W., Revised sequence of the tetracycline-resistance gene of pBR322. 1983. Gene 22: 277-280.

Ray, A., and R. Skurray. 1984. Stabilization of the cloning vector pACYC184 by insertion of F plasmid leading region sequences. Plasmid 11: 272-275.

Sambrook et al., 1989. *Molecular Cloning. A Laboratory Manual*, 2nd ed. Cold Spring Harbor Laboratory Press, Cold Spring Harbor, N.Y.

Stirling, C. J., S. D. Colloms, J. F. Collins, G. Szatmari, and D. J. Sherratt. 1989. xerB, an *Escherichia coli* gene required for plasmid ColE1 site specific recombination is identical to pepA, encoding aminopeptidase A, a protein with substantial similarity to bovine lens leucine aminopeptidase. EMBO J. 8: 1623-1627.

Stirling, C. J. G. Szatmari, G. Stewart, M C. M. Smith, and D. J. Sherratt. 1988. The arginine repressor is essential for plasmid stabilising site-specific recombination at the ColE1 cer locus. EMBO J. 7: 4389-4395.

Summers, D. K. 1989. Derivatives of ColE1 cer show altered topological specificity in site-specific recombination. EMBO J. 8: 309-316.

Summers, D. K. 1991. The kinetics of plasmid loss. TIBTECH 9: 273-278.

Summers, D. K. 1996. The biology of plasmids. Blackwell Science Ltd., London

Summers, D. K., and D. C. D. Rowe. 2001. Methods and means relating to quiescent cells and uses thereof. U.S. Pat. No. 6,190,867.

Summers, D. K., and D. J. Sherratt. 1988. Resolution of ColE1 dimers requires a DNA sequence implicated in the three-dimensional organization of the cer site. EMBO J. 7: 851-858.

Summers, D. K., C. W. H. Beton, and H. L. Withers. 1993. Multicopy plasmid instability—the dimer catastrophe hypothesis. Mol. Microbiol. 8: 1031-1038.

Summers, D., S. Yaish, J. Archer, and D. Sherratt. 1985. Multimer resolution systems of ColE1 and ColK: localisation of the crossover site. Mol. Gen. Genet. 201: 334-338.

Sutcliffe, J. G. 1978. Nucleotide sequence of the ampicillin resistance gene of *Escherichia coli* plasmid pBR322. Proc. Natl. Acad. Sci. U.S.A., 75: 3737-3741.

Sutcliffe, J. G. 1979. Complete nucleotide sequence of the *Escherichia coli* plasmid pBR322. Cold Spring Harb. Symp. Quant. Biol., 43: 77-90.

Watson, N. 1988. A new revision of the sequence of plasmid pBR322. Gene 70: 399-403.

---

SEQUENCE LISTING

```
<160> NUMBER OF SEQ ID NOS: 34

<210> SEQ ID NO 1
<211> LENGTH: 4361
<212> TYPE: DNA
<213> ORGANISM: Unknown
<220> FEATURE:
<223> OTHER INFORMATION: Recombinant plasmid pBR322

<400> SEQUENCE: 1
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtggcaggcc ccgtggccgg     540
gggactgttg ggcgccatct ccttgcatgc accattcctt gcggcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
gctctgggtc attttcggcg aggaccgctt tcgctggagc gcgacgatga tcggcctgtc     840
gcttgcggta ttcggaatct tgcacgccct cgctcaagcc ttcgtcactg gtcccgccac     900
caaacgtttc ggcgagaagc aggccattat cgccggcatg gcggccgacg cgctgggcta     960
```

```
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcattgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
agaattggag ccaatcaatt cttgcggaga actgtgaatg cgcaaaccaa cccttggcag   1380
aacatatcca tcgcgtccgc catctccagc agccgcacgc ggcgcatctc gggcagcgtt   1440
gggtcctggc cacgggtgcg catgatcgtg ctcctgtcgt tgaggacccg gctaggctgg   1500
cggggttgcc ttactggtta gcagaatgaa tcaccgatac gcgagcgaac gtgaagcgac   1560
tgctgctgca aaacgtctgc gacctgagca acaacatgaa tggtcttcgg tttccgtgtt   1620
tcgtaaagtc tggaaacgcg gaagtcagcg ccctgcacca ttatgttccg gatctgcatc   1680
gcaggatgct gctggctacc ctgtggaaca cctacatctg tattaacgaa gcgctggcat   1740
tgaccctgag tgattttttct ctggtcccgc cgcatccata ccgccagttg tttaccctca   1800
caacgttcca gtaaccgggc atgttcatca tcagtaaccc gtatcgtgag catcctctct   1860
cgtttcatcg gtatcattac ccccatgaac agaaatcccc cttacacgga ggcatcagtg   1920
accaaacagg aaaaaaccgc ccttaacatg gcccgcttta tcagaagcca gacattaacg   1980
cttctggaga aactcaacga gctggacgcg gatgaacagg cagacatctg tgaatcgctt   2040
cacgaccacg ctgatgagct ttaccgcagc tgcctcgcgc gtttcggtga tgacggtgaa   2100
aacctctgac acatgcagct cccggagacg gtcacagctt gtctgtaagc ggatgccggg   2160
agcagacaag cccgtcaggg cgcgtcagcg ggtgttggcg ggtgtcgggg cgcagccatg   2220
acccagtcac gtagcgatag cggagtgtat actggcttaa ctatgcggca tcagagcaga   2280
ttgtactgag agtgcaccat atgcggtgtg aaataccgca cagatgcgta aggagaaaat   2340
accgcatcag gcgctcttcc gcttcctcgc tcactgactc gctgcgctcg gtcgttcggc   2400
tgcggcgagc ggtatcagct cactcaaagg cggtaatacg ttatccaca gaatcagggg   2460 ataacgcagg aaagaacatg tgagcaaaag gccagcaaaa ggccaggaac cgtaaaaagg   2520
ccgcgttgct ggcgtttttc cataggctcc gcccccctga cgagcatcac aaaaatcgac   2580
gctcaagtca gaggtggcga aacccgacag gactataaag ataccaggcg tttccccctg   2640
gaagctccct cgtgcgctct cctgttccga ccctgccgct taccggatac ctgtccgcct   2700
ttctcccttc gggaagcgtg gcgctttctc atagctcacg ctgtaggtat ctcagttcgg   2760
tgtaggtcgt tcgctccaag ctgggctgtg tgcacgaacc cccgttcag cccgaccgct   2820 gcgccttatc cggtaactat cgtcttgagt ccaacccggt aagacacgac ttatcgccac   2880
tggcagcagc cactggtaac aggattagca gagcgaggta tgtaggcggt gctacagagt   2940
tcttgaagtg gtggcctaac tacggctaca ctagaaggac agtatttggt atctgcgctc   3000
tgctgaagcc agttaccttc ggaaaaagag ttggtagctc ttgatccggc aaacaaacca   3060
ccgctggtag cggtggtttt tttgtttgca agcagcagat tacgcgcaga aaaaaggat   3120 ctcaagaaga tcctttgatc ttttctacgg ggtctgacgc tcagtggaac gaaaactcac   3180
gttaagggat tttggtcatg agattatcaa aaaggatctt cacctagatc cttttaaatt   3240
aaaaatgaag ttttaaatca atctaaagta tatatgagta aacttggtct gacagttacc   3300
```

```
aatgcttaat cagtgaggca cctatctcag cgatctgtct atttcgttca tccatagttg    3360
cctgactccc cgtcgtgtag ataactacga tacgggaggg cttaccatct ggccccagtg    3420
ctgcaatgat accgcgagac ccacgctcac cggctccaga tttatcagca ataaaccagc    3480
cagccggaag ggccgagcgc agaagtggtc ctgcaacttt atccgcctcc atccagtcta    3540
ttaattgttg ccgggaagct agagtaagta gttcgccagt taatagtttg cgcaacgttg    3600
ttgccattgc tgcaggcatc gtggtgtcac gctcgtcgtt tggtatggct tcattcagct    3660
ccggttccca acgatcaagg cgagttacat gatcccccat gttgtgcaaa aaagcggtta    3720
gctccttcgg tcctccgatc gttgtcagaa gtaagttggc cgcagtgtta ctcactcatgg   3780 ttatggcagc actgcataat tctcttactg tcatgccatc cgtaagatgc ttttctgtga    3840
ctggtgagta ctcaaccaag tcattctgag aatagtgtat gcggcgaccg agttgctctt    3900
gcccggcgtc aacacgggat aataccgcgc cacatagcag aactttaaaa gtgctcatca    3960
ttggaaaacg ttcttcgggg cgaaaactct caaggatctt accgctgttg agatccagtt    4020
cgatgtaacc cactcgtgca cccaactgat cttcagcatc ttttactttc accagcgttt    4080
ctgggtgagc aaaaacagga aggcaaaatg ccgcaaaaaa gggaataagg gcgacacgga    4140
aatgttgaat actcatactc ttcctttttc aatattattg aagcatttat cagggttatt    4200
gtctcatgag cggatacata tttgaatgta tttagaaaaa taaacaaata ggggttccgc    4260
gcacatttcc ccgaaaagtg ccacctgacg tctaagaaac cattattatc atgacattaa    4320
cctataaaaa taggcgtatc acgaggccct ttcgtcttca a                        4361

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
gctcggccct tccggctggc                                                20

<210> SEQ ID NO 3
<211> LENGTH: 50
<212> TYPE: DNA
<213> ORGANISM: Artificial sequence
<220> FEATURE:
<223> OTHER INFORMATION: Primer

<400> SEQUENCE: 3
ttacgcgcag aaaaaaagga tctcaagaag atcctttaat cttttctacg                50

<210> SEQ ID NO 4
<211> LENGTH: 399
<212> TYPE: DNA
<213> ORGANISM: Artificial sequence
<220> FEATURE:
<223> OTHER INFORMATION: Primer

<400> SEQUENCE: 4
gctcggccct tccggctggc tggtttattg ctgataaatc tggagccggt gagcgtgggt    60
ctcgcggtat cattgcagca ctggggccag atggtaagcc ctcccgtatc gtagttatct    120
acacgacggg gagtcaggca actatggatg aacgaaatag acagatcgct gagataggtg    180
cctcactgat taagcattgg taactgtcag accaagttta ctcatatata ctttagattg    240
atttaaaact tcattttaa tttaaaagga tctaggtgaa gatcctttt gataatctca     300
```

| | |
|---|---|
| tgaccaaaat cccttaacgt gagttttcgt tccactgagc gtcagacccc gtagaaaaga | 360 |
| ttaaaggatc ttcttgagat ccttttttc tgcgcgtaa | 399 |

<210> SEQ ID NO 5
<211> LENGTH: 26
<212> TYPE: DNA
<213> ORGANISM: Artificial sequence
<220> FEATURE:
<223> OTHER INFORMATION: Primer

<400> SEQUENCE: 5

| | |
|---|---|
| ccttctagtg tagccgtagt cgggcc | 26 |

<210> SEQ ID NO 6
<211> LENGTH: 6647
<212> TYPE: DNA
<213> ORGANISM: Unknown
<220> FEATURE:
<223> OTHER INFORMATION: Recombinant plasmid ColE1

<400> SEQUENCE: 6

| | |
|---|---|
| ttctatgctc ctatattgat aagaataaac ttaatactat aaatgaggtg ttagggattt | 60 |
| aattattctt tattgatata aaaagtccta gcaatccaaa tgggattgct aggaccaaac | 120 |
| aaagtagatt atatagcata aataggttta attttgctac gggggcgtta tttaggtttt | 180 |
| ttcttcttc gaaaaaatct ttctttatga agttaaaagc tatgtattca atagcatatt | 240 |
| ttgaatatgg acatagaata gtgcttatca ctattgcata tagcatctta tctgacacaa | 300 |
| ggaaataata cccttcgctg ttttttgtta taaggtatat atatataagt gtgcagtaca | 360 |
| ggccaaataa atatttttt atgtagtatc ttaagctcat aaattaaacc tcgccatata | 420 |
| ttcttttcat tttataagga tcgagttatg aggaaaagat ttttgtggg aatattcgcg | 480 |
| ataaacctcc ttgttggatg tcaggctaac tatatacgtg atgttcaggg agggaccatc | 540 |
| gcaccatcct cctcttctaa actgacgggg atcgcggttc agtagaaaag attaaaggat | 600 |
| cttcttgaga tccttttttt ctgcgcgtaa tctgctgctt gcaaacaaaa aaaccaccgc | 660 |
| taccaacggt ggtttgtttg ccggatcaag agctaccaac tctttttccg aaggtaactg | 720 |
| gcttcagcag agcgcagata ccaaatactg tccttctagt gtagccgtag tcgggccact | 780 |
| acttcaagaa ctctgtagca ccgtttgtgc catcatcgct ctgctaatcc ggttaccagt | 840 |
| ggctgctgcc agtggcgtta aggcgtgcct taccggggttg gactcaagac gatagttacc | 900 |
| ggataaggcg cagcggtcgg gctgaacggg gggttcgtgc acacagccca gcttggagcg | 960 |
| aacgacctac accgaactga gataccaaca gcgtgagcta tgagaaagcg ccacgcttcc | 1020 |
| cgaagggaga aaggcggaca ggtatccggt aagcggcagg gtcggaacag gagagcgcac | 1080 |
| gagggagctt ccagggggaa acgcctggta tctttatagt cctgtcgggt ttcgccacct | 1140 |
| ctgacttgag cgtctatttt tgtgatgctc gtcaggggg cggagcctat ggaaaaacgc | 1200 |
| ctgctacgtg gccttcttcc tgttcctggt cttttgctca catgttcttt ccggccttat | 1260 |
| cccctgattc tgtggataac tgtgttaccg ttttttgtgtg agtcagtacc gctcgccgca | 1320 |
| gtcgaacgac cgagcgtagc gagtcagtga gcgaggaagc ggaaaagcgc ctggacgtgc | 1380 |
| attttctcct tacgcatctg tgcggcattt cacacccggc atggcgtact tttcatacaa | 1440 |
| tccgcactga tgccgcatgg ttaagccagt atacactccg ctatcgctac gtgactgggt | 1500 |
| cagggctgcg ccccgacacc cgctaaaacc tgctgacgcg ccctgacggg cttgtcagct | 1560 |

```
cccggcatcc gctcacagac aagctgtgac cgtctccggg agctgcatgt gtcagaggtt    1620
ttcaccgtca tccccgaaac gtgcgaggca gctgcggtaa agctcatcgg cgtggtcgtg    1680
aagcgattca caaatatcgg cctgttcatc tgcgtccagt tcgttgagct tctccagcag    1740
cgttaatgtc tggcttctga taaagcgggc catgttaagg gcggttttt cctgtttagt     1800
cactgatgcc tccgtgtaag ggggatttct gttcatgggg taatgatacc gatgaaacgc    1860
gagaggatgc tcacaatacg ggttactgat gatgaacatg cccggttact tgaacgctgt    1920
gagggtaaac aactggcggt atggatgcgg cgggtctgcc tgggggagcc ggttgcccgt    1980
tccgaaaaac tgccgacact ggcaccgccg ttactgcgtc agctggccgc catcggaaat    2040
aacctgaatc agacagcccg taaggtgaac agcgggcagt ggtcttccgg tgaccgggtt    2100
caggtggtgg ccgcactgat ggccatcggg atgagctgc gccggctgcg tctggctgtc     2160
agggaacagg gggcgcggga tgatagttaa atttcatgcc aggggaaaag gtggtggcag    2220
tggtccggtt gattacctgc tggggaggga gcgtaaccgc gaaggcgcaa cggtgcttca    2280
gggtaatccg gaagaagtcc gggaactcat cgatgccacg ccatttgcga agaaatacac    2340
gtccggtgtt ctgtcgttcg cggagaagga gctgccgccg ggaggacgtg aaaaagtgat    2400
ggcgagcttt gagcgtgtac tgatgcccgg tctcgaaaaa aatcagtaca gcatcctgtg    2460
ggtggagcac caggacaagg gacggcttga gctgaatttt gtcattccga acatggagct    2520
acagaccgga aaacgcctcc agccgtacta cgaccgcgca gacaggccta gaattgatgc    2580
ctggcagacg ctggtaaatc accattacgg gctgcatgac ccgaacgccc cggagaaccg    2640
caggacgctg acactccctg ataacctgcc tgaaacgaaa caggcgcttg ctgagggcgt    2700
cacgcgaggt atagatgcac tttaccatgc cggagagata aaaggccgtc aggatgtgat    2760
tcaggcgctc actgaggcgg ggctggaagt ggtcagggtg acgcgaagca gtatcagcat    2820
tgcagatccg aacggcggga agaatatcag gctgaaagga gcattttatg agcaatcttt    2880
tgcagacggg cgcggagttc gagaaaaagc tgaaagagag agccgaatct acagagaaaa    2940
tgctgaacaa cgagttcagg aggctcggcg aatctgtaag cgaggctgtg acatcaaacg    3000
agacgaaaat cagagacgct atagccctgt tcacagcctc gacagaggaa tcgctggaaa    3060
aacaccggga aggggtgaaa gaggcgatga tgcagcacag gagggacgtg ttaaagctgg    3120
cagggaatac gggcatgatg ttactgggga tagtcttttct cctgtttacc gcagtggcg    3180
ggacgctctg gtatcttgga gggaggatac aggcgaacct ggaagaaatc aggaagcagg    3240
aagagacatt gcagaaactg aacgcgaaga catgggcgt ggagtttgtg caggacggga     3300
acaggaaatt ccttgtcctt ccgtacggga atcagcgga ggtgattccc tttcagggga     3360
aagagtgggt acatctgaag gagtgacaca gagtgacaga gctggaaaca catttgctga    3420
acgccttaga gcagctgcaa caggactata tgcagcggct gagcgaatgg gagagcgcct    3480
tcgtggaatt gcagaagatg ttttcgctta cgcaacggga caacgcgatg ctgaacgagc    3540
gggtcatgca gttgagtcag caggtgcagc acttgagcga gcagacagaa cgcttgagcc    3600
agttatacag cgagaactgg agataagaga ggaacggctg atacaggagc gcgaacatgt    3660
gttatccctg gaacgggagc gtcagccgga aatacaggaa cgcacgctgg atggcccttc    3720
gctgggatgg tgaaaccatg aaaaatggca gcttcagtgg attaagtggg ggtaatgtgg    3780
cctgtaccct ctggttgcat aggtattcat acggttaaaa tttatcaggc gcgatcgcgg    3840
cagttttttcg ggtggtttgt tgccattttt acctgtctgc tgccgtgatc gcgctgaacg    3900
cgttttagcg gtgcgtacaa ttaagggatt atggtaaatc cacttactgt ctgccctcgt    3960
```

```
agccatcgag ataaaccgca gaaatcgtgt cagccagcag cctggatttt ttcggggtaa    4020
ggtctttgct gcggtaatca gtacccgcaa attgagttgt gccccggagt gagtttaaaa    4080
attcctggct gtgaaactgc tgaatgcgtt gttgcacatc actccgtgat tttcctgtcg    4140
ctttatcttt agctcccata tcccagaact gccgaaaaaa aggcaccatc attcgtgttg    4200
tgtcggcttt ttgggtggaa aagttgggat caaaaccgtc atcagaagca tatacgtaat    4260
gccgggtatg ttgttccacg ctgccctttg gggtacaggc tgtgagagct actgttgctg    4320
ttatcatggc gataagacaa agtttgtttc cggtacgtct catgagtgtc tccctacctt    4380
aaagtattta ttctcggtga gttattatcc gaagactatt ttatcatcag tctctgacag    4440
cgttcagcga ccgaacaacc tggaccagaa tccccgtttc ttttccagtt ccagtgcctg    4500
cctgagctgg gctatctcat tttgtagctg ttcccgttct gcttcctggc gtctgcgatc    4560
catatcctgt gcctgtttat cctcaagcat cagcgtcagg cattgtttca gctcattcag    4620
ttcccggaga atgcgttctg tctgctgatc atgtggattt tctgcatgtc cctcactgtg    4680
cctttctggt gtctcattct gctttaattc gccgtatgcc cggatcagtt cactggtttc    4740
aaactcccgt cgtccgtccc tgccggtacg gtaactgaca aggcctgcgc gcatatcacg    4800
gtaaaactgt gaacgcgatc tgcctgtcat ttttagtgcg tcccggagtg tgtgccatgc    4860
cataaagtga cagtgtccca tagatgtctc atctcatagt ttcagtaaaa cataatgagg    4920
tctgagaacg gtaatgtttg tgctggtttt tgtggcatcg ggcgagaata gcgcgtggtg    4980
tgaaagactt ttttttttgat cgttttcaca aaaatggaag tccacagtct tgacagggaa    5040
aatgcagcgg cgtagctttt atgctgtata taaaaccagt ggttatatgt acagtattta    5100
tttttaactt attgttttaa aagtcaaaga ggatttttata atggaaaccg cggtagcgta    5160
ctataaagat ggtgttcctt atgatgataa gggacaggta attattactc ttttgaatgg    5220
tactcctgac gggagtggct ctggcggcgg aggtggaaaa ggaggcagta aaagtgaaag    5280
ttctgcagct attcatgcaa ctgctaaatg gtctactgct caattaaaga aaacacaggc    5340
agagcaggct gcccgggcaa agctgcagc ggaagcacag gcgaaagcaa aggcaaacag    5400
ggatgcgctg actcagcgcc tgaaggatat cgtgaatgag gctcttcgtc acaatgcctc    5460
acgtacgcct tcagcaacag agcttgctca tgctaataat gcagctatgc aggcggaagc    5520
agagcgtttg cgccttgcga aagcagaaga aaaagcccgt aaagaagcgg aagcagcaga    5580
aaaggctttt caggaagcag aacaacgacg taaagagatt gaacgggaga aggctgaaac    5640
agaacgccag ttgaaactgg ctgaagctga agagaaacga ctggctgcat tgagtgaaga    5700
agctaaagct gttgagatcg cccaaaaaaa actttctgct gcacaatctg aagtggtgaa    5760
aatggatgga gagattaaga ctctcaattc tcgtttaagc tccagtatcc atgcccgtga    5820
tgcagaaatg aaaacgctcg ctggaaaacg aaatgaactg gctcaggcat ccgctaaata    5880
taaagaactg gatgagctgg tcaaaaaact atcaccaaga gccaatgatc cgcttcagaa    5940
ccgtcctttt tttgaagcaa ccagacgacg ggttggggcc ggtaagatta gagaagaaaa    6000
acaaaaacag gtaacagcat cagaaacacg tattaaccgg ataaatgctg atataactca    6060
gatccagaag gctatttctc aggtcagtaa taatcgtaat gccggtatcg ctcgtgttca    6120
tgaagctgaa gaaaatttga aaaagcaca gaataatctc cttaattcac agattaagga    6180
tgctgttgat gcaacagtta gcttttatca acgctgact gaaaaatatg gtgaaaaata    6240
ttcgaaaatg gcacaggaac ttgctgataa gtctaaaggt aagaaaatcg gcaatgtgaa    6300
```

-continued

| | |
|---|---|
| tgaagctctc gctgcttttg aaaaatacaa ggatgtttta aataagaaat tcagcaaagc | 6360 |
| cgatcgtgat gctatttta atgcgttggc atcggtgaag tatgatgact gggctaaaca | 6420 |
| tttagatcag tttgccaagt acttgaagat tacggggcat gtttctttg gatatgatgt | 6480 |
| ggtatctgat atcctaaaaa ttaaggatac aggtgactgg aagccactat ttcttacatt | 6540 |
| agagaagaaa gctgcagatg caggggtgag ttatgttgtt gctttacttt ttagcttgct | 6600 |
| tgctggaact acattaggta tttggggtat tgctattgtt acaggaa | 6647 |

<210> SEQ ID NO 7
<211> LENGTH: 4363
<212> TYPE: DNA
<213> ORGANISM: Unknown
<220> FEATURE:
<223> OTHER INFORMATION: Recombinant plasmid pXT975

<400> SEQUENCE: 7

| | |
|---|---|
| gaattctcat gtttgacagc ttatcatcga taagctttaa tgcggtagtt tatcacagtt | 60 |
| aaattgctaa cgcagtcagg caccgtgtat gaaatctaac aatgcgctca tcgtcatcct | 120 |
| cggcaccgtc accctggatg ctgtaggcat aggcttggtt atgccggtac tgccgggcct | 180 |
| cttgcgggat atcgtccatt ccgacagcat cgccagtcac tatggcgtgc tgctagcgct | 240 |
| atatgcgttg atgcaatttc tatgcgcacc cgttctcgga gcactgtccg accgctttgg | 300 |
| ccgccgccca gtcctgctcg cttcgctact tggagccact atcgactacg cgatcatggc | 360 |
| gaccacaccc gtcctgtgga tcctctacgc cggacgcatc gtggccggca tcaccggcgc | 420 |
| cacaggtgcg gttgctggcg cctatatcgc cgacatcacc gatggggaag atcgggctcg | 480 |
| ccacttcggg ctcatgagcg cttgtttcgg cgtgggtatg gtggcaggcc ccgtggccgg | 540 |
| gggactgttg ggcgccatct ccttgcatgc accattcctt gcggcggcgg tgctcaacgg | 600 |
| cctcaaccta ctactgggct gcttcctaat gcaggagtcg cataagggag agcgtcgacc | 660 |
| gatgcccttg agagccttca acccagtcag ctccttccgg tgggcgcggg gcatgactat | 720 |
| cgtcgccgca cttatgactg tcttctttat catgcaactc gtaggacagg tgccggcagc | 780 |
| gctctgggtc attttcggcg aggaccgctt tcgctggagc gcgacgatga tcggcctgtc | 840 |
| gcttgcggta ttcggaatct tgcacgccct cgctcaagcc ttcgtcactg gtcccgccac | 900 |
| caaacgtttc ggcgagaagc aggccattat cgccggcatg gcggccgacg cgctgggcta | 960 |
| cgtcttgctg gcgttcgcga cgcgaggctg gatggccttc cccattatga ttcttctcgc | 1020 |
| ttccggcggc atcgggatgc ccgcgttgca ggccatgctg tccaggcagg tagatgacga | 1080 |
| ccatcaggga cagcttcaag atcgctcgc ggctcttacc agcctaactt cgatcactgg | 1140 |
| accgctgatc gtcacggcga tttatgccgc ctcggcgagc acatggaacg ggttggcatg | 1200 |
| gattgtaggc gccgccctat accttgtctg cctccccgcg ttgcgtcgcg gtgcatggag | 1260 |
| ccgggccacc tcgacctgaa tggaagccgg cggcacctcg ctaacggatt caccactcca | 1320 |
| agaattggag ccaatcaatt cttgcggaga actgtgaatg cgcaaaccaa cccttggcag | 1380 |
| aacatatcca tcgcgtccgc catctccagc agccgcacgc ggcgcatctc gggcagcgtt | 1440 |
| gggtcctggc cacgggtgcg catgatcgtg ctcctgtcgt tgaggacccg gctaggctgg | 1500 |
| cggggttgcc ttactggtta gcagaatgaa tcaccgatac gcgagcgaac gtgaagcgac | 1560 |
| tgctgctgca aaacgtctgc gacctgagca acaacatgaa tggtcttcgg tttccgtgtt | 1620 |
| tcgtaaagtc tggaaacgcg gaagtcagcg ccctgcacca ttatgttccg gatctgcatc | 1680 |
| gcaggatgct gctggctacc ctgtggaaca cctacatctg tattaacgaa gcgctggcat | 1740 |

```
tgaccctgag tgattttcct ctggtcccgc cgcatccata ccgccagttg tttaccctca    1800
caacgttcca gtaaccgggc atgttcatca tcagtaaccc gtatcgtgag catcctctct    1860
cgtttcatcg gtatcattac ccccatgaac agaaatcccc cttacacgga ggcatcagtg    1920
accaaacagg aaaaaaccgc ccttaacatg cccgcttta tcagaagcca gacattaacg     1980
cttctggaga aactcaacga gctggacgcg gatgaacagg cagacatctg tgaatcgctt    2040
cacgaccacg ctgatgagct ttaccgcagc tgcctcgcgc gtttcggtga tgacggtgaa    2100
aacctctgac acatgcagct cccggagacg gtcacagctt gtctgtaagc ggatgccggg    2160
agcagacaag cccgtcaggg cgcgtcagcg ggtgttggcg ggtgtcgggg cgcagccatg    2220
acccagtcac gtagcgatag cggagtgtat actggcttaa ctatgcggca tcagagcaga    2280
ttgtactgag agtgcaccat atgcggtgtg aaataccgca cagatgcgta aggagaaaat    2340
accgcatcag gcgctcttcc gcttcctcgc tcactgactc gctgcgctcg gtcgttcggc    2400
tgcggcgagc ggtatcagct cactcaaagg cggtaatacg gttatccaca gaatcagggg    2460
ataacgcagg aaagaacatg tgagcaaaag gccagcaaaa ggccaggaac cgtaaaaagg    2520
ccgcgttgct ggcgtttttc cataggctcc gcccccctga cgagcatcac aaaaatcgac    2580
gctcaagtca gaggtggcga aacccgacag gactataaag ataccaggcg tttccccctg    2640
gaagctccct cgtgcgctct cctgttccga ccctgccgct taccggatac ctgtccgcct    2700
ttctcccttc gggaagcgtg gcgctttctc atagctcacg ctgtaggtat ctcagttcgg    2760
tgtaggtcgt tcgctccaag ctgggctgtg tgcacgaacc ccccgttcag cccgaccgct    2820
gcgccttatc cggtaactat cgtcttgagt ccaacccggt aagacacgac ttatcgccac    2880
tggcagcagc cactggtaac cggattagca gagcgatgat ggcacaaacg gtgctacaga    2940
gttcttgaag tagtggcccg actacggcta cactagaagg acagtatttg gtatctgcgc    3000
tctgctgaag ccagttacct tcggaaaaag agttggtagc tcttgatccg gcaaacaaac    3060
caccgttggt agcggtggtt ttttgtttg caagcagcag attacgcgca gaaaaaaagg     3120
atctcaagaa gatcctttaa tcttttctac ggggtctgac gctcagtgga acgaaaactc    3180
acgttaaggg attttggtca tgagattatc aaaaaggatc ttcacctaga tccttttaaa    3240
ttaaaaatga agttttaaat caatctaaag tatatatgag taaacttggt ctgacagtta    3300
ccaatgctta atcagtgagg cacctatctc agcgatctgt ctatttcgtt catccatagt    3360
tgcctgactc cccgtcgtgt agataactac gatacgggag ggcttaccat ctggccccag    3420
tgctgcaatg ataccgcgag acccacgctc accggctcca gatttatcag caataaacca    3480
gccagccgga agggccgagc gcagaagtgg tcctgcaact ttatccgcct ccatccagtc    3540
tattaattgt tgccgggaag ctagagtaag tagttcgcca gttaatagtt tgcgcaacgt    3600
tgttgccatt gctgcaggca tcgtggtgtc acgctcgtcg tttggtatgg cttcattcag    3660
ctccggttcc caacgatcaa ggcgagttac atgatccccc atgttgtgca aaaaagcggt    3720
tagctccttc ggtcctccga tcgttgtcag aagtaagttg gccgcagtgt tatcactcat    3780
ggttatggca gcactgcata attctcttac tgtcatgcca tccgtaagat gcttttctgt    3840
gactggtgag tactcaacca agtcattctg agaatagtgt atgcggcgac cgagttgctc    3900
ttgcccggcg tcaacacggg ataataccgc gccacatagc agaactttaa aagtgctcat    3960
cattggaaaa cgttcttcgg ggcgaaaact ctcaaggatc ttaccgctgt tgagatccag    4020
ttcgatgtaa cccactcgtg cacccaactg atcttcagca tcttttactt tcaccagcgt    4080
```

```
ttctgggtga gcaaaaacag gaaggcaaaa tgccgcaaaa agggaataa gggcgacacg        4140 gaaatgttga atactcatac tcttccttttt tcaatattat tgaagcattt atcagggtta     4200
ttgtctcatg agcggataca tatttgaatg tatttagaaa aataaacaaa tagggggttcc    4260 gcgcacattt ccccgaaaag tgccacctga cgtctaagaa accattatta tcatgacatt     4320
aacctataaa aataggcgta tcacgaggcc ctttcgtctt caa                        4363

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
gcgacctgag caacaacatg aatgg                                             25

<210> SEQ ID NO 9
<211> LENGTH: 50
<212> TYPE: DNA
<213> ORGANISM: Artificial sequence
<220> FEATURE:
<223> OTHER INFORMATION: Primer

<400> SEQUENCE: 9
ttacttgaac gctgtgaggg taaacaactg gcggtatgga tgcggcggga                  50

<210> SEQ ID NO 10
<211> LENGTH: 236
<212> TYPE: DNA
<213> ORGANISM: Artificial sequence
<220> FEATURE:
<223> OTHER INFORMATION: Primer

<400> SEQUENCE: 10
gcgacctgag caacaacatg aatggtcttc ggtttccgtg tttcgtaaag tctggaaacg       60
cggaagtcag cgccctgcac cattatgttc cggatctgca tcgcaggatg ctgctggcta      120
ccctgtggaa cacctacatc tgtattaacg aagcgctggc attgaccctg agtgattttt      180
ctctggtccc gccgcatcca taccgccagt tgtttaccct cacagcgttc aagtaa          236

<210> SEQ ID NO 11
<211> LENGTH: 24
<212> TYPE: DNA
<213> ORGANISM: Artificial sequence
<220> FEATURE:
<223> OTHER INFORMATION: Primer

<400> SEQUENCE: 11
gcccgaccgc tgcgccttat ccgg                                              24

<210> SEQ ID NO 12
<211> LENGTH: 4349
<212> TYPE: DNA
<213> ORGANISM: Unknown
<220> FEATURE:
<223> OTHER INFORMATION: Recombinant plasmid pXT976

<400> SEQUENCE: 12
gaattctcat gtttgacagc ttatcatcga taagctttaa tgcggtagtt tatcacagtt       60
aaattgctaa cgcagtcagg caccgtgtat gaaatctaac aatgcgctca tcgtcatcct      120
cggcaccgtc accctggatg ctgtaggcat aggcttggtt atgccggtac tgccgggcct     180
```

```
cttgcgggat atcgtccatt ccgacagcat cgccagtcac tatggcgtgc tgctagcgct    240
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcctctacgc cggacgcatc gtggccggca tcaccggcgc    420
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt gcggcggcgg tgctcaacgg    600
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt cgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgcccata accttgtctg cctccccgcg ttgcgtcgcg gtgcatggag   1260
ccgggccacc tcgacctgaa tggaagccgg cggcacctcg ctaacggatt caccactcca   1320
agaattggag ccaatcaatt cttgcggaga actgtgaatg cgcaaaccaa cccttggcag   1380
aacatatcca tcgcgtccgc catctccagc agccgcacgc ggcgcatctc gggcagcgtt   1440
gggtcctggc cacgggtgcg catgatcgtg ctcctgtcgt tgaggacccg gctaggctgg   1500
cggggttgcc ttactggtta gcagaatgaa tcaccgatac gcgagcgaac gtgaagcgac   1560
tgctgctgca aaacgtctgc gacctgagca acaacatgaa tggtcttcgg tttccgtgtt   1620
tcgtaaagtc tggaaacgcg gaagtcagcg ccctgcacca ttatgttccg gatctgcatc   1680
gcaggatgct gctggctacc ctgtggaaca cctacatctg tattaacgaa gcgctggcat   1740
tgaccctgag tgattttct ctggtcccgc cgcatccata ccgccagttg tttaccctca   1800
cagcgttcaa gtaaccgggc atgttcatca tcagtaaccc gtattgtgag catcctctcg   1860
cgtttcatcg gtatcattac cccatgaaca gaaatccccc ttacacgag gcatcagtga    1920 ctaaacagga aaaaccgcc cttaacatgg cccgctttat cagaagccag acattaacgc   1980
tgctggagaa gctcaacgaa ctggacgcag atgaacaggc cgatatttgt gaatcgcttc   2040
acgaccacgc cgatgagctt taccgcagct gcctcgcacg tttcggggat gacggtgaaa   2100
acctctgaca catgcagctc ccggagacgt cacagcttg tctgtgagcg gatgccggga   2160
gctgacaagc ccgtcagggc gcgtcagcag gtttttagcgg gtgtcggggc gcagccctga   2220
cccagtcacg tagcgatagc ggagtgtata ctggcttaac catgcggcat cagtgcggat   2280
tgtatgaaaa gtacgccatg ccgggtgtga atgccgcac agatgcgtaa ggagaaaatg   2340
cacgtccagg cgctttttccg cttcctcgct cactgactcg ctacgctcgg tcgttcgact   2400
gcggcgagcg gtactgactc acacaaaaac ggtaacacag ttatccacag aatcagggga   2460
taaggccgga aagaacatgt gagcaaaaga ccaggaacag gaagaaggcc acgtagcagg   2520
```

| | |
|---|---|
| cgtttttcca taggctccgc cccccctgacg agcatcacaa aaatagacgc tcaagtcaga | 2580 |
| ggtggcgaaa cccgacagga ctataaagat accaggcgtt tccccctgga agctccctcg | 2640 |
| tgcgctctcc tgttccgacc ctgccgctta ccggatacct gtccgccttt ctcccttcgg | 2700 |
| gaagcgtggc gctttctcat agctcacgct gttggtatct cagttcggtg taggtcgttc | 2760 |
| gctccaagct gggctgtgtg cacgaacccc ccgttcagcc cgaccgctgc gccttatccg | 2820 |
| gtaactatcg tcttgagtcc aacccggtaa ggcacgcctt aacgccactg gcagcagcca | 2880 |
| ctggtaacag gattagcaga gcgaggtatg taggcggtgc tacagagttc ttgaagtggt | 2940 |
| ggcctaacta cggctacact agaaggacag tatttggtat ctgcgctctg ctgaagccag | 3000 |
| ttaccttcgg aaaaagagtt ggtagctctt gatccggcaa acaaaccacc gctggtagcg | 3060 |
| gtggtttttt tgtttgcaag cagcagatta cgcgcagaaa aaaaggatct caagaagatc | 3120 |
| ctttgatctt ttctacgggg tctgacgctc agtggaacga aaactcacgt taagggattt | 3180 |
| tggtcatgag attatcaaaa aggatcttca cctagatcct tttaaattaa aaatgaagtt | 3240 |
| ttaaatcaat ctaaagtata tatgagtaaa cttggtctga cagttaccaa tgcttaatca | 3300 |
| gtgaggcacc tatctcagcg atctgtctat ttcgttcatc catagttgcc tgactccccg | 3360 |
| tcgtgtagat aactacgata cgggagggct taccatctgg ccccagtgct gcaatgatac | 3420 |
| cgcgagaccc acgctcaccg gctccagatt tatcagcaat aaaccagcca gccggaaggg | 3480 |
| ccgagcgcag aagtggtcct gcaactttat ccgcctccat ccagtctatt aattgttgcc | 3540 |
| gggaagctag agtaagtagt tcgccagtta atagtttgcg caacgttgtt gccattgctg | 3600 |
| caggcatcgt ggtgtcacgc tcgtcgtttg gtatggcttc attcagctcc ggttcccaac | 3660 |
| gatcaaggcg agttacatga tcccccatgt tgtgcaaaaa agcggttagc tccttcggtc | 3720 |
| ctccgatcgt tgtcagaagt aagttggccg cagtgttatc actcatggtt atggcagcac | 3780 |
| tgcataattc tcttactgtc atgccatccg taagatgctt ttctgtgact ggtgagtact | 3840 |
| caaccaagtc attctgagaa tagtgtatgc ggcgaccgag ttgctcttgc ccggcgtcaa | 3900 |
| cacgggataa taccgcgcca catagcagaa ctttaaaagt gctcatcatt ggaaaacgtt | 3960 |
| cttcggggcg aaaactctca aggatcttac cgctgttgag atccagttcg atgtaaccca | 4020 |
| ctcgtgcacc caactgatct tcagcatctt ttactttcac cagcgtttct gggtgagcaa | 4080 |
| aaacaggaag gcaaaatgcc gcaaaaaagg gaataagggc gacacggaaa tgttgaatac | 4140 |
| tcatactctt cctttttcaa tattattgaa gcatttatca gggttattgt ctcatgagcg | 4200 |
| gatacatatt tgaatgtatt tagaaaaata aacaaatagg ggttccgcgc acatttcccc | 4260 |
| gaaaagtgcc acctgacgtc taagaaacca ttattatcat gacattaacc tataaaaata | 4320 |
| ggcgtatcac gaggcccttt cgtcttcaa | 4349 |

<210> SEQ ID NO 13
<211> LENGTH: 4351
<212> TYPE: DNA
<213> ORGANISM: Unknown
<220> FEATURE:
<223> OTHER INFORMATION: Recombinant plasmid pXT977

<400> SEQUENCE: 13

| | |
|---|---|
| gaattctcat gtttgacagc ttatcatcga taagctttaa tgcggtagtt tatcacagtt | 60 |
| aaattgctaa cgcagtcagg caccgtgtat gaaatctaac aatgcgctca tcgtcatcct | 120 |
| cggcaccgtc accctggatg ctgtaggcat aggcttggtt atgccggtac tgccgggcct | 180 |
| cttgcgggat atcgtccatt ccgacagcat cgccagtcac tatggcgtgc tgctagcgct | 240 |

```
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcctctacgc cggacgcatc gtggccggca tcaccggcgc    420
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt cgcggcggcg tgctcaacgg    600
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt tcgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
agaattggag ccaatcaatt cttgcggaga actgtgaatg cgcaaaccaa cccttggcag   1380
aacatatcca tcgcgtccgc catctccagc agccgcacgc ggcgcatctc gggcagcgtt   1440
gggtcctggc cacgggtgcg catgatcgtg ctcctgtcgt tgaggacccg gctaggctgg   1500
cggggttgcc ttactggtta gcagaatgaa tcaccgatac gcgagcgaac gtgaagcgac   1560
tgctgctgca aaacgtctgc gacctgagca acaacatgaa tggtcttcgg tttccgtgtt   1620
tcgtaaagtc tggaaacgcg gaagtcagcg ccctgcacca ttatgttccg gatctgcatc   1680
gcaggatgct gctggctacc ctgtggaaca cctacatctg tattaacgaa gcgctggcat   1740
tgaccctgag tgattttct ctggtcccgc cgcatccata ccgccagttg tttaccctca   1800
cagcgttcaa gtaaccgggc atgttcatca tcagtaaccc gtattgtgag catcctctcg   1860
cgtttcatcg gtatcattac cccatgaaca gaaatcccccc ttacacggag gcatcagtga   1920
ctaaacagga aaaaaccgcc cttaacatgg cccgctttat cagaagccag acattaacgc   1980
tgctggagaa gctcaacgaa ctggacgcag atgaacaggc cgatatttgt gaatcgcttc   2040
acgaccacgc cgatgagctt taccgcagct gcctcgcacg tttcggggat gacggtgaaa   2100
acctctgaca catgcagctc ccggagacgg tcacagcttg tctgtgagcg gatgccggga   2160
gctgacaagc ccgtcagggc gcgtcagcag gttttagcgg gtgtcgggcc gcagccctga   2220
cccagtcacg tagcgatagc ggagtgtata ctggcttaac catgcggcat cagtgcggat   2280
tgtatgaaaa gtacgccatg ccgggtgtga aatgccgcac agatgcgtaa ggagaaaatg   2340
cacgtccagg cgcttttccg cttcctcgct cactgactcg ctacgctcgg tcgttcgact   2400
gcggcgagcg gtactgactc acacaaaaac ggtaacacag ttatccacag aatcagggga   2460
taaggccgga aagaacatgt gagcaaaaga ccaggaacag gaagaaggcc acgtagcagg   2520 cgttttttcca taggctccgc cccctgacg agcatcacaa aaatagacgc tcaagtcaga   2580
```

-continued

| | |
|---|---|
| ggtggcgaaa cccgacagga ctataaagat accaggcgtt tcccctgga agctccctcg | 2640 |
| tgcgctctcc tgttccgacc ctgccgctta ccggatacct gtccgccttt ctcccttcgg | 2700 |
| gaagcgtggc gctttctcat agctcacgct gttggtatct cagttcggtg taggtcgttc | 2760 |
| gctccaagct gggctgtgtg cacgaacccc ccgttcagcc cgaccgctgc gccttatccg | 2820 |
| gtaactatcg tcttgagtcc aacccggtaa ggcacgcctt aacgccactg gcagcagcca | 2880 |
| ctggtaaccg gattagcaga gcgatgatgg cacaaacggt gctacagagt tcttgaagta | 2940 |
| gtggcccgac tacggctaca ctagaaggac agtatttggt atctgcgctc tgctgaagcc | 3000 |
| agttaccttc ggaaaaagag ttggtagctc ttgatccggc aaacaaacca ccgttggtag | 3060 |
| cggtggtttt tttgtttgca agcagcagat tacgcgcaga aaaaaggat ctcaagaaga | 3120 |
| tcctttaatc ttttctacgg ggtctgacgc tcagtggaac gaaaactcac gttaagggat | 3180 |
| tttggtcatg agattatcaa aaaggatctt cacctagatc cttttaaatt aaaaatgaag | 3240 |
| ttttaaatca atctaaagta tatatgagta aacttggtct gacagttacc aatgcttaat | 3300 |
| cagtgaggca cctatctcag cgatctgtct atttcgttca tccatagttg cctgactccc | 3360 |
| cgtcgtgtag ataactacga tacgggaggg cttaccatct ggccccagtg ctgcaatgat | 3420 |
| accgcgagac ccacgctcac cggctccaga tttatcagca ataaaccagc cagccggaag | 3480 |
| ggccgagcgc agaagtggtc ctgcaacttt atccgcctcc atccagtcta ttaattgttg | 3540 |
| ccgggaagct agagtaagta gttcgccagt taatagtttg cgcaacgttg ttgccattgc | 3600 |
| tgcaggcatc gtggtgtcac gctcgtcgtt tggtatggct tcattcagct ccggttccca | 3660 |
| acgatcaagg cgagttacat gatccccat gttgtgcaaa aaagcggtta gctccttcgg | 3720 |
| tcctccgatc gttgtcagaa gtaagttggc cgcagtgtta tcactcatgg ttatggcagc | 3780 |
| actgcataat tctcttactg tcatgccatc cgtaagatgc ttttctgtga ctggtgagta | 3840 |
| ctcaaccaag tcattctgag aatagtgtat gcggcgaccg agttgctctt gcccggcgtc | 3900 |
| aacacgggat aataccgcgc cacatagcag aactttaaaa gtgctcatca ttggaaaacg | 3960 |
| ttcttcgggg cgaaaactct caaggatctt accgctgttg agatccagtt cgatgtaacc | 4020 |
| cactcgtgca cccaactgat cttcagcatc ttttactttc accagcgttt ctgggtgagc | 4080 |
| aaaaacagga aggcaaaatg ccgcaaaaaa gggaataagg gcgacacgga aatgttgaat | 4140 |
| actcatactc ttcctttttc aatattattg aagcatttat cagggttatt gtctcatgag | 4200 |
| cggatacata tttgaatgta tttagaaaaa taaacaaata ggggttccgc gcacatttcc | 4260 |
| ccgaaaagtg ccacctgacg tctaagaaac cattattatc atgacattaa cctataaaaa | 4320 |
| taggcgtatc acgaggccct ttcgtcttca a | 4351 |

<210> SEQ ID NO 14
<211> LENGTH: 50
<212> TYPE: DNA
<213> ORGANISM: Artificial sequence
<220> FEATURE:
<223> OTHER INFORMATION: Primer

<400> SEQUENCE: 14
gctgtgaggg taaacaactg gcggtatgga tgcggcgggg cggccgcatg     50

<210> SEQ ID NO 15
<211> LENGTH: 50
<212> TYPE: DNA
<213> ORGANISM: Artificial sequence
<220> FEATURE:
<223> OTHER INFORMATION: Primer

<400> SEQUENCE: 15
agaaaaaaag gatctcaaga agatccttta atcttttcta cgagctcact          50

<210> SEQ ID NO 16
<211> LENGTH: 409
<212> TYPE: DNA
<213> ORGANISM: Artificial sequence
<220> FEATURE:
<223> OTHER INFORMATION: Primer

<400> SEQUENCE: 16
gctcggccct tccggctggc tggtttattg ctgataaatc tggagccggt gagcgtgggt          60
ctcgcggtat cattgcagca ctggggccag atggtaagcc ctcccgtatc gtagttatct         120
acacgacggg gagtcaggca actatggatg aacgaaatag acagatcgct gagataggtg         180
cctcactgat taagcattgg taactgtcag accaagttta ctcatatata ctttagattg         240
atttaaaact tcattttaa tttaaaagga tctaggtgaa gatcctttt gataatctca           300 tgaccaaaat cccttaacgt gagttttcgt tccactgagc gtcagacccc agatctacta         360
gtgagctcgt agaaaagatt aaaggatctt cttgagatcc ttttttttct                    409

<210> SEQ ID NO 17
<211> LENGTH: 246
<212> TYPE: DNA
<213> ORGANISM: Artificial sequence
<220> FEATURE:
<223> OTHER INFORMATION: Primer

<400> SEQUENCE: 17
gcgacctgag caacaacatg aatggtcttc ggtttccgtg tttcgtaaag tctggaaacg          60
cggaagtcag cgccctgcac cattatgttc cggatctgca tcgcaggatg ctgctggcta        120
ccctgtggaa cacctacatc tgtattaacg aagcgctggc attgaccctg agtgattttt        180
ctctggtaga tctatgcatg cggccgcccc gccgcatcca taccgccagt tgtttaccct        240
cacagc                                                                    246

<210> SEQ ID NO 18
<211> LENGTH: 4389
<212> TYPE: DNA
<213> ORGANISM: Unknown
<220> FEATURE:
<223> OTHER INFORMATION: Recombinant plasmid pXT988

<400> SEQUENCE: 18
gaattctcat gtttgacagc ttatcatcga taagctttaa tgcggtagtt tatcacagtt         60
aaattgctaa cgcagtcagg caccgtgtat gaaatctaac aatgcgctca tcgtcatcct        120
cggcaccgtc accctggatg ctgtaggcat aggcttggtt atgccggtac tgccgggcct        180
cttgcgggat atcgtccatt ccgacagcat cgccagtcac tatggcgtgc tgctagcgct        240
atatgcgttg atgcaatttc tatgcgcacc cgttctcgga gcactgtccg accgctttgg        300
ccgccgccca gtcctgctcg cttcgctact tggagccact atcgactacg cgatcatggc        360
gaccacaccc gtcctgtgga tcctctacgc cggacgcatc gtggccggca tcaccggcgc        420
cacaggtgcg gttgctggcg cctatatcgc cgacatcacc gatggggaag atcgggctcg        480
ccacttcggg ctcatgagcg cttgtttcgg cgtgggtatg gtggcaggcc ccgtggccgg        540
gggactgttg ggcgccatct ccttgcatgc accattcctt gcggcggcgg tgctcaacgg        600

```
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt tcgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
agaattggag ccaatcaatt cttgcggaga actgtgaatg cgcaaccaa cccttggcag   1380 aacatatcca tcgcgtccgc catctccagc agccgcacgc ggcgcatctc gggcagcgtt   1440
gggtcctggc cacgggtgcg catgatcgtg ctcctgtcgt tgaggacccg gctaggctgg   1500
cggggttgcc ttactggtta gcagaatgaa tcaccgatac gcgagcgaac gtgaagcgac   1560
tgctgctgca aaacgtctgc gacctgagca acaacatgaa tggtcttcgg tttccgtgtt   1620
tcgtaaagtc tggaaacgcg gaagtcagcg ccctgcacca ttatgttccg gatctgcatc   1680
gcaggatgct gctggctacc ctgtggaaca cctacatctg tattaacgaa gcgctggcat   1740
tgaccctgag tgattttttct ctggtagatc tatgcatgcg gccgccccgc cgcatccata   1800
ccgccagttg tttaccctca cagcgttcaa gtaaccgggc atgttcatca tcagtaaccc   1860
gtattgtgag catcctctcg cgtttcatcg gtatcattac cccatgaaca gaaatccccc   1920
ttacacggag gcatcagtga ctaaacagga aaaaaccgcc cttaacatgg cccgctttat   1980
cagaagccag acattaacgc tgctggagaa gctcaacgaa ctggacgcag atgaacaggc   2040
cgatatttgt gaatcgcttc acgaccacgc cgatgagctt taccgcagct gcctcgcacg   2100
tttcggggat gacggtgaaa acctctgaca catgcagctc ccggagacgg tcacagcttg   2160
tctgtgagcg gatgccggga gctgacaagc ccgtcagggc gcgtcagcag gttttagcgg   2220 gtgtcgggc gcagccctga cccagtcacg tagcgatagc ggagtgtata ctggcttaac   2280
catgcggcat cagtgcggat tgtatgaaaa gtacgccatg ccgggtgtga atgccgcac   2340 agatgcgtaa ggagaaaatg cacgtccagg cgcttttccg cttcctcgct cactgactcg   2400
ctacgctcgg tcgttcgact gcggcgagcg gtactgactc acacaaaaac ggtaacacag   2460
ttatccacag aatcagggga taaggccgga agaacatgt gagcaaaaga ccaggaacag   2520
gaagaaggcc acgtagcagg cgttttttcca taggctccgc cccctgacg agcatcacaa   2580 aaatagacgc tcaagtcaga ggtggcgaaa cccgacagga ctataaagat accaggcgtt   2640 tcccctgga agctccctcg tgcgctctcc tgttccgacc ctgccgctta ccggatacct   2700
gtccgccttt ctcccttcgg gaagcgtggc gctttctcat agctcacgct gttggtatct   2760
cagttcggtg taggtcgttc gctccaagct gggctgtgtg cacgaacccc ccgttcagcc   2820
cgaccgctgc gccttatccg gtaactatcg tcttgagtcc aacccggtaa ggcacgcctt   2880
aacgccactg gcagcagcca ctggtaaccg gattagcaga gcgatgatgg cacaaacggt   2940
gctacagagt tcttgaagta gtggcccgac tacggctaca ctagaaggac agtatttggt   3000
```

```
atctgcgctc tgctgaagcc agttaccttc ggaaaaagag ttggtagctc ttgatccggc    3060
aaacaaacca ccgttggtag cggtggtttt tttgtttgca agcagcagat tacgcgcaga    3120
aaaaaaggat ctcaagaaga tcctttaatc ttttctacga gctcactagt agatctgggg    3180
tctgacgctc agtggaacga aaactcacgt taagggattt tggtcatgag attatcaaaa    3240
aggatcttca cctagatcct tttaaattaa aaatgaagtt ttaaatcaat ctaaagtata    3300
tatgagtaaa cttggtctga cagttaccaa tgcttaatca gtgaggcacc tatctcagcg    3360
atctgtctat ttcgttcatc catagttgcc tgactccccg tcgtgtagat aactacgata    3420
cgggagggct taccatctgg ccccagtgct gcaatgatac cgcgagaccc acgctcaccg    3480
gctccagatt tatcagcaat aaaccagcca gccggaaggg ccgagcgcag aagtggtcct    3540
gcaactttat ccgcctccat ccagtctatt aattgttgcc gggaagctag agtaagtagt    3600
tcgccagtta atagtttgcg caacgttgtt gccattgctg caggcatcgt ggtgtcacgc    3660
tcgtcgtttg gtatggcttc attcagctcc ggttcccaac gatcaaggcg agttacatga    3720
tcccccatgt tgtgcaaaaa agcggttagc tccttcggtc ctccgatcgt tgtcagaagt    3780
aagttggccg cagtgttatc actcatggtt atggcagcac tgcataattc tcttactgtc    3840
atgccatccg taagatgctt ttctgtgact ggtgagtact caaccaagtc attctgagaa    3900
tagtgtatgc ggcgaccgag ttgctcttgc ccggcgtcaa cacgggataa taccgcgcca    3960
catagcagaa ctttaaaagt gctcatcatt ggaaaacgtt cttcggggcg aaaactctca    4020
aggatcttac cgctgttgag atccagttcg atgtaaccca ctcgtgcacc caactgatct    4080
tcagcatctt ttactttcac cagcgtttct gggtgagcaa aaacaggaag gcaaaatgcc    4140
gcaaaaaagg gaataagggc gacacggaaa tgttgaatac tcatactctt cctttttcaa    4200
tattattgaa gcatttatca gggttattgt ctcatgagcg gatacatatt tgaatgtatt    4260
tagaaaaata aacaaatagg ggttccgcgc acatttcccc gaaaagtgcc acctgacgtc    4320
taagaaacca ttattatcat gacattaacc tataaaaata ggcgtatcac gaggcccttt    4380
cgtcttcaa                                                          4389

<210> SEQ ID NO 19
<211> LENGTH: 49
<212> TYPE: DNA
<213> ORGANISM: Artificial sequence
<220> FEATURE:
<223> OTHER INFORMATION: Primer

<400> SEQUENCE: 19
aggaagatct atgcatgcgg ccgccccgcc gcatccatac cgccagttg                49

<210> SEQ ID NO 20
<211> LENGTH: 48
<212> TYPE: DNA
<213> ORGANISM: Artificial sequence
<220> FEATURE:
<223> OTHER INFORMATION: Primer

<400> SEQUENCE: 20
aggaagatct actagtgagc tcgtagaaaa gatcaaagga tcttcttg                 48

<210> SEQ ID NO 21
<211> LENGTH: 4399
<212> TYPE: DNA
<213> ORGANISM: Unknown
<220> FEATURE:
```

<223> OTHER INFORMATION: Recombinant plasmid pXT995

<400> SEQUENCE: 21

```
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtgcaggcc ccgtggccgg      540
gggactgttg ggcgccatct ccttgcatgc accattcctt gcggcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
gctctgggtc attttcggcg aggaccgctt tcgctggagc gcgacgatga tcggcctgtc     840
gcttgcggta ttcggaatct gcacgcccct cgctcaagcc ttcgtcactg gtcccgccac     900
caaacgtttc ggcgagaagc aggccattat cgccggcatg cggccgacg cgctgggcta      960
cgtcttgctg gcgttcgcga cgcgaggctg gatggccttc cccattatga ttcttctcgc    1020
ttccggcggc atcgggatgc cgcgttgca ggccatgctg tccaggcagg tagatgacga     1080
ccatcaggga cagcttcaag gatcgctcgc ggctcttacc agcctaactt cgatcattgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
agaattggag ccaatcaatt cttgcggaga actgtgaatg cgcaaaccaa cccttggcag    1380
aacatatcca tcgcgtccgc catctccagc agccgcacgc ggcgcatctc gggcagcgtt    1440
gggtcctggc cacgggtgcg catgatcgtg ctcctgtcgt tgaggacccg gctaggctgg    1500
cggggttgcc ttactggtta gcagaatgaa tcaccgatac gcgagcgaac gtgaagcgac    1560
tgctgctgca aaacgtctgc gacctgagca acaacatgaa tggtcttcgg tttccgtgtt    1620
tcgtaaagtc tggaaacgcg gaagtcagcg ccctgcacca ttatgttccg gatctgcatc    1680
gcaggatgct gctggctacc ctgtggaaca cctacatctg tattaacgaa gcgctggcat    1740
tgaccctgag tgattttcct ctggtagatc tatgcatgcg gccgccccgc cgcatccata    1800
ccgccagttg tttaccctca caacgttcca gtaaccgggc atgttcatca tcagtaaccc    1860
gtatcgtgag catcctctct cgtttcatcg gtatcattac cccatgaac agaaatcccc     1920
cttacacgga ggcatcagtg accaaacagg aaaaaaccgc ccttaacatg gcccgcttta    1980
tcagaagcca gacattaacg cttctggaga aactcaacga gctggacgcg gatgaacagg    2040
cagacatctg tgaatcgctt cacgaccacg ctgatgagct ttaccgcagc tgcctcgcgc    2100
gtttcggtga tgacggtgaa aacctctgac acatgcagct cccggagacg gtcacagctt    2160
gtctgtaagc ggatgccggg agcagacaag cccgtcaggg cgcgtcagcg ggtgttggcg    2220
ggtgtcgggg cgcagccatg acccagtcac gtagcgatag cggagtgtat actggcttaa    2280
```

```
ctatgcggca tcagagcaga ttgtactgag agtgcaccat atgcggtgtg aaataccgca    2340
cagatgcgta aggagaaaat accgcatcag gcgctcttcc gcttcctcgc tcactgactc    2400
gctgcgctcg gtcgttcggc tgcggcgagc ggtatcagct cactcaaagg cggtaatacg    2460
gttatccaca gaatcagggg ataacgcagg aaagaacatg tgagcaaaag gccagcaaaa    2520
ggccaggaac cgtaaaaagg ccgcgttgct ggcgtttttc cataggctcc gcccccctga    2580
cgagcatcac aaaaatcgac gctcaagtca gaggtggcga aacccgacag gactataaag    2640
ataccaggcg tttccccctg gaagctccct cgtgcgctct cctgttccga ccctgccgct    2700
taccggatac ctgtccgcct ttctcccttc gggaagcgtg gcgctttctc atagctcacg    2760
ctgtaggtat ctcagttcgg tgtaggtcgt tcgctccaag ctgggctgtg tgcacgaacc    2820
ccccgttcag cccgaccgct gcgccttatc cggtaactat cgtcttgagt ccaacccggt    2880
aagacacgac ttatcgccac tggcagcagc cactggtaac aggattagca gagcgaggta    2940
tgtaggcggt gctacagagt tcttgaagtg gtggcctaac tacggctaca ctagaaggac    3000
agtatttggt atctgcgctc tgctgaagcc agttaccttc ggaaaaagag ttggtagctc    3060
ttgatccggc aaacaaacca ccgctggtag cggtggtttt tttgtttgca agcagcagat    3120
tacgcgcaga aaaaaggat ctcaagaaga tcctttgatc ttttctacga gctcactagt    3180
agatctgggg tctgacgctc agtggaacga aaactcacgt taagggattt tggtcatgag    3240
attatcaaaa aggatcttca cctagatcct tttaaattaa aaatgaagtt ttaaatcaat    3300
ctaaagtata tatgagtaaa cttggtctga cagttaccaa tgcttaatca gtgaggcacc    3360
tatctcagcg atctgtctat ttcgttcatc catagttgcc tgactccccg tcgtgtagat    3420
aactacgata cgggagggct taccatctgg ccccagtgct gcaatgatac cgcgagaccc    3480
acgctcaccg gctccagatt tatcagcaat aaaccagcca gccggaaggg ccgagcgcag    3540
aagtggtcct gcaactttat ccgcctccat ccagtctatt aattgttgcc gggaagctag    3600
agtaagtagt tcgccagtta atagtttgcg caacgttgtt gccattgctg caggcatcgt    3660
ggtgtcacgc tcgtcgtttg gtatggcttc attcagctcc ggttcccaac gatcaaggcg    3720
agttacatga tcccccatgt tgtgcaaaaa agcggttagc tccttcggtc ctccgatcgt    3780
tgtcagaagt aagttggccg cagtgttatc actcatggtt atggcagcac tgcataattc    3840
tcttactgtc atgccatccg taagatgctt ttctgtgact ggtgagtact caaccaagtc    3900
attctgagaa tagtgtatgc ggcgaccgag ttgctcttgc ccggcgtcaa cacgggataa    3960
taccgcgcca catagcagaa ctttaaaagt gctcatcatt ggaaaacgtt cttcggggcg    4020
aaaactctca aggatcttac cgctgttgag atccagttcg atgtaaccca ctcgtgcacc    4080
caactgatct tcagcatctt ttactttcac cagcgtttct gggtgagcaa aaacaggaag    4140
gcaaaatgcc gcaaaaaagg gaataagggc gacacggaaa tgttgaatac tcatactctt    4200
cctttttcaa tattattgaa gcatttatca gggttattgt ctcatgagcg gatacatatt    4260
tgaatgtatt tagaaaaata aacaatagg ggttccgcgc acatttcccc gaaaagtgcc    4320
acctgacgtc taagaaacca ttattatcat gacattaacc tataaaaata ggcgtatcac    4380
gaggcccttt cgtcttcaa                                                4399
```

<210> SEQ ID NO 22
<211> LENGTH: 4387
<212> TYPE: DNA
<213> ORGANISM: Unknown
<220> FEATURE:

<223> OTHER INFORMATION: Recombinant plasmid pXT1000

<400> SEQUENCE: 22

```
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtggcaggcc ccgtggccgg     540
gggactgttg ggcgccatct ccttgcatgc accattcctt gcggcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
gctctgggtc attttcggcg aggaccgctt tcgctggagc gcgacgatga tcggcctgtc     840
gcttgcggta ttcggaatct gcacgcccct cgctcaagcc ttcgtcactg gtcccgccac     900
caaacgtttc ggcgagaagc aggccattat cgccggcatg gcggccgacg cgctgggcta     960
cgtcttgctg gcgttcgcga cgcgaggctg gatggccttc cccattatga ttcttctcgc    1020
ttccggcggc atcgggatgc cgcgttgca ggccatgctg tccaggcagg tagatgacga    1080
ccatcaggga cagcttcaag gatcgctcgc ggctcttacc agcctaactt cgatcactgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
agaattggag ccaatcaatt cttgcggaga actgtgaatg cgcaaaccaa cccttggcag    1380
aacatatcca tcgcgtccgc catctccagc agccgcacgc ggcgcatctc gggcagcgtt    1440
gggtcctggc cacgggtgcg catgatcgtg ctcctgtcgt tgaggacccg gctaggctgg    1500
cggggttgcc ttactggtta gcagaatgaa tcaccgatac gcgagcgaac gtgaagcgac    1560
tgctgctgca aaacgtctgc gacctgagca acaacatgaa tggtcttcgg tttccgtgtt    1620
tcgtaaagtc tggaaacgcg gaagtcagcg ccctgcacca ttatgttccg gatctgcatc    1680
gcaggatgct gctggctacc ctgtggaaca cctacatctg tattaacgaa gcgctggcat    1740
tgaccctgag tgattttct ctggtagatc tatgcatgcg gccgccccgc cgcatccata    1800
ccgccagttg tttaccctca cagcgttcaa gtaaccgggc atgttcatca tcagtaaccc    1860
gtattgtgag catcctctcg cgtttcatcg gtatcattac cccatgaaca gaaatccccc    1920
ttacacggag gcatcagtga ctaaacagga aaaaccgcc cttaacatgg cccgctttat    1980
cagaagccag acattaacgc tgctggagaa gctcaacgaa ctggacgcag atgaacaggc    2040
cgatatttgt gaatcgcttc acgaccacgc cgatgagctt taccgcagct gcctcgcacg    2100
tttcggggat gacggtgaaa acctctgaca catgcagctc ccggagacgg tcacagcttg    2160
tctgtgagcg gatgccggga gctgacaagc ccgtcagggc gcgtcagcag gttttagcgg    2220
gtgtcggggc gcagccctga cccagtcacg tagcgatagc ggagtgtata ctggcttaac    2280
```

```
catgcggcat cagtgcggat tgtatgaaaa gtacgccatg ccgggtgtga aatgccgcac    2340
agatgcgtaa ggagaaaatg cacgtccagg cgcttttccg cttcctcgct cactgactcg    2400
ctacgctcgg tcgttcgact gcggcgagcg gtactgactc acacaaaaac ggtaacacag    2460
ttatccacag aatcagggga taaggccgga agaacatgt gagcaaaaga ccaggaacag     2520
gaagaaggcc acgtagcagg cgttttccca taggctccgc cccctgacg agcatcacaa     2580 aaatagacgc tcaagtcaga ggtggcgaaa cccgacagga ctataaagat accaggcgtt    2640
tccccctgga agctccctcg tgcgctctcc tgttccgacc ctgccgctta ccggatacct    2700
gtccgccttt ctcccttcgg gaagcgtggc gctttctcat agctcacgct gttggtatct    2760
cagttcggtg taggtcgttc gctccaagct gggctgtgtg cacgaacccc ccgttcagcc    2820
cgaccgctgc gccttatccg gtaactatcg tcttgagtcc aacccggtaa ggcacgcctt    2880
aacgccactg gcagcagcca ctggtaacag gattagcaga gcgaggtatg taggcggtgc    2940
tacagagttc ttgaagtggt ggcctaacta cggctacact agaaggacag tatttggtat    3000
ctgcgctctg ctgaagccag ttaccttcgg aaaaagagtt ggtagctctt gatccggcaa    3060
acaaaccacc gctggtagcg gtggtttttt tgtttgcaag cagcagatta cgcgcagaaa    3120
aaaaggatct caagaagatc ctttgatctt ttctacgagc tcactagtag atctggggtc    3180
tgacgctcag tggaacgaaa actcacgtta agggattttg gtcatgagat tatcaaaaag    3240
gatcttcacc tagatccttt taaattaaaa atgaagtttt aaatcaatct aaagtatata    3300
tgagtaaact tggtctgaca gttaccaatg cttaatcagt gaggcaccta tctcagcgat    3360
ctgtctattt cgttcatcca tagttgcctg actccccgtc gtgtagataa ctacgatacg    3420
ggagggctta ccatctggcc ccagtgctgc aatgataccg cgagacccac gctcaccggc    3480
tccagattta tcagcaataa accagccagc cggaagggcc gagcgcagaa gtggtcctgc    3540
aactttatcc gcctccatcc agtctattaa ttgttgccgg gaagctagag taagtagttc    3600
gccagttaat agtttgcgca acgttgttgc cattgctgca ggcatcgtgg tgtcacgctc    3660
gtcgtttggt atggcttcat tcagctccgg ttcccaacga tcaaggcgag ttacatgatc    3720
ccccatgttg tgcaaaaaag cggttagctc cttcggtcct ccgatcgttg tcagaagtaa    3780
gttggccgca gtgttatcac tcatggttat ggcagcactg cataattctc ttactgtcat    3840
gccatccgta agatgctttt ctgtgactgg tgagtactca accaagtcat tctgagaata    3900
gtgtatgcgg cgaccgagtt gctcttgccc ggcgtcaaca cgggataata ccgcgccaca    3960
tagcagaact ttaaaagtgc tcatcattgg aaaacgttct tcggggcgaa aactctcaag    4020
gatcttaccg ctgttgagat ccagttcgat gtaacccact cgtgcaccca actgatcttc    4080
agcatctttt actttcacca gcgtttctgg gtgagcaaaa acaggaaggc aaaatgccgc    4140
aaaaaaggga ataagggcga cacggaaatg ttgaatactc atactcttcc ttttcaata     4200 ttattgaagc atttatcagg gttattgtct catgagcgga tacatatttg aatgtattta    4260
gaaaaataaa caaatagggg ttccgcgcac atttccccga aaagtgccac ctgacgtcta    4320
agaaaccatt attatcatga cattaaccta taaaaatagg cgtatcacga ggccctttcg    4380
tcttcaa                                                              4387

<210> SEQ ID NO 23
<211> LENGTH: 4401
<212> TYPE: DNA
<213> ORGANISM: Unknown
<220> FEATURE:
```

<223> OTHER INFORMATION: Recombinant plasmid pXT1001

<400> SEQUENCE: 23

```
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact ggagccact atcgactacg cgatcatggc      360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtggcaggcc ccgtggccgg     540
gggactgttg ggcgccatct ccttgcatgc accattcctt gcggcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
gctctgggtc atttcggcg aggaccgctt tcgctggagc gcgacgatga tcggcctgtc      840
gcttgcggta ttcggaatct gcacgccct cgctcaagcc ttcgtcactg gtcccgccac      900
caaacgtttc ggcgagaagc aggccattat cgccggcatg gcggccgacg cgctgggcta     960
cgtcttgctg gcgttcgcga cgcgaggctg atggccttc cccattatga ttcttctcgc     1020
ttccggcggc atcgggatgc ccgcgttgca ggccatgctg tccaggcagg tagatgacga    1080
ccatcaggga cagcttcaag gatcgctcgc ggctcttacc agcctaactt cgatcactgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
agaattggag ccaatcaatt cttgcggaga actgtgaatg cgcaaaccaa cccttggcag    1380
aacatatcca tcgcgtccgc catctccagc agccgcacgc ggcgcatctc gggcagcgtt    1440
gggtcctggc cacgggtgcg catgatcgtg ctcctgtcgt tgaggacccg gctaggctgg    1500
cggggttgcc ttactggtta gcagaatgaa tcaccgatac gcgagcgaac gtgaagcgac    1560
tgctgctgca aaacgtctgc gacctgagca acaacatgaa tggtcttcgg tttccgtgtt    1620
tcgtaaagtc tggaaacgcg gaagtcagcg ccctgcacca ttatgttccg gatctgcatc    1680
gcaggatgct gctggctacc ctgtggaaca cctacatctg tattaacgaa gcgctggcat    1740
tgaccctgag tgatttttct ctggtagatc tatgcatgcg gccgccccgc cgcatccata    1800
ccgccagttg tttaccctca caacgttcca gtaaccgggc atgttcatca tcagtaaccc    1860
gtatcgtgag catcctctct cgtttcatcg gtatcattac cccatgaac agaaatcccc     1920
cttacacgga ggcatcagtg accaaacagg aaaaaaccgc ccttaacatg gcccgcttta    1980
tcagaagcca gacattaacg cttctggaga aactcaacga gctggacgcg gatgaacagg    2040
cagacatctg tgaatcgctt cacgaccacg ctgatgagct ttaccgcagc tgcctcgcgc    2100
gtttcggtga tgacggtgaa aacctctgac acatgcagct cccggagacg gtcacagctt    2160
gtctgtaagc ggatgccggg agcagacaag cccgtcaggg cgcgtcagcg ggtgttggcg    2220
ggtgtcgggg cgcagccatg acccagtcac gtagcgatag cggagtgtat actggcttaa    2280
```

```
ctatgcggca tcagagcaga ttgtactgag agtgcaccat atgcggtgtg aaataccgca   2340
cagatgcgta aggagaaaat accgcatcag gcgctcttcc gcttcctcgc tcactgactc   2400
gctgcgctcg tcgttcggc tgcggcgagc ggtatcagct cactcaaagg cggtaatacg   2460
gttatccaca gaatcagggg ataacgcagg aaagaacatg tgagcaaaag gccagcaaaa   2520
ggccaggaac cgtaaaaagg ccgcgttgct ggcgtttttc cataggctcc gcccccctga   2580
cgagcatcac aaaaatcgac gctcaagtca gaggtggcga acccgacag gactataaag   2640
ataccaggcg tttccccctg gaagctccct cgtgcgctct cctgttccga ccctgccgct   2700
taccggatac ctgtccgcct ttctcccttc gggaagcgtg gcgctttctc atagctcacg   2760
ctgtaggtat ctcagttcgg tgtaggtcgt tcgctccaag ctgggctgtg tgcacgaacc   2820
ccccgttcag cccgaccgct gcgccttatc cggtaactat cgtcttgagt ccaacccggt   2880
aagacacgac ttatcgccac tggcagcagc cactggtaac cggattagca gagcgatgat   2940
ggcacaaacg gtgctacaga gttcttgaag tagtggcccg actacggcta cactagaagg   3000
acagtatttg gtatctgcgc tctgctgaag ccagttacct tcggaaaaag agttggtagc   3060
tcttgatccg gcaaacaaac caccgttggt agcggtggtt ttttgtttg caagcagcag   3120
attacgcgca gaaaaaagg atctcaagaa gatcctttaa tcttttctac gagctcacta   3180
gtagatctgg ggtctgacgc tcagtggaac gaaaactcac gttaagggat tttggtcatg   3240
agattatcaa aaaggatctt cacctagatc ctttaaatt aaaaatgaag ttttaaatca   3300
atctaaagta tatatgagta aacttggtct gacagttacc aatgcttaat cagtgaggca   3360
cctatctcag cgatctgtct atttcgttca tccatagttg cctgactccc cgtcgtgtag   3420
ataactacga tacgggaggg cttaccatct ggccccagtg ctgcaatgat accgcgagac   3480
ccacgctcac cggctccaga tttatcagca ataaccagc cagccggaag ggccgagcgc   3540
agaagtggtc ctgcaacttt atccgcctcc atccagtcta ttaattgttg ccgggaagct   3600
agagtaagta gttcgccagt taatagtttg cgcaacgttg ttgccattgc tgcaggcatc   3660
gtggtgtcac gctcgtcgtt tggtatggct tcattcagct ccggttccca acgatcaagg   3720
cgagttacat gatccccat gttgtgcaaa aaagcggtta gctccttcgg tcctccgatc   3780
gttgtcagaa gtaagttggc cgcagtgtta tcactcatgg ttatggcagc actgcataat   3840
tctcttactg tcatgccatc cgtaagatgc ttttctgtga ctggtgagta ctcaaccaag   3900
tcattctgag aatagtgtat gcggcgaccg agttgctctt gcccggcgtc aacacgggat   3960
aataccgcgc cacatagcag aactttaaa gtgctcatca ttggaaaacg ttcttcgggg   4020
cgaaaactct caaggatctt accgctgttg agatccagtt cgatgtaacc cactcgtgca   4080
cccaactgat cttcagcatc ttttactttc accagcgttt ctgggtgagc aaaaacagga   4140
aggcaaaatg ccgcaaaaaa gggaataagg gcgacacgga aatgttgaat actcatactc   4200
ttccttttc aatattattg aagcatttat cagggttatt gtctcatgag cggatacata   4260
tttgaatgta tttagaaaaa taaacaaata ggggttccgc gcacatttcc ccgaaaagtg   4320
ccacctgacg tctaagaaac cattattatc atgacattaa cctataaaaa taggcgtatc   4380
acgaggccct ttcgtcttca a                                             4401
```

<210> SEQ ID NO 24
<211> LENGTH: 4245
<212> TYPE: DNA
<213> ORGANISM: Unknown
<220> FEATURE:

<223> OTHER INFORMATION: Recombinant plasmid pACYC184

<400> SEQUENCE: 24

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgccccctg acaagcatca cgaaatctga cgctcaaatc      900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttctaga tttcagtgca    1440
atttatctct tcaaatgtag cacctgaagt cagccccata cgatataagt tgtaattctc    1500
atgtttgaca gcttatcatc gataagcttt aatgcggtag tttatcacag ttaaattgct    1560
aacgcagtca ggcaccgtgt atgaaatcta acaatgcgct catcgtcatc ctcggcaccg    1620
tcaccctgga tgctgtaggc ataggcttgg ttatgccggt actgccgggc ctcttgcggg    1680
atatcgtcca ttccgacagc atcgccagtc actatggcgt gctgctagcg ctatatgcgt    1740
tgatgcaatt tctatgcgca cccgttctcg gagcactgtc cgaccgcttt ggccgccgcc    1800
cagtcctgct cgcttcgcta cttggagcca ctatcgacta cgcgatcatg cgaccacac     1860
ccgtcctgtg gatcctctac gccggacgca tcgtggccgg catcaccggc gccacaggtg    1920
cggttgctgg cgcctatatc gccgacatca ccgatgggga agatcgggct cgccacttcg    1980
ggctcatgag cgcttgtttc ggcgtgggta tggtggcagg ccccgtggcc ggggactgt     2040
tgggcgccat ctccttgcat gcaccattcc ttgcggcggc ggtgctcaac ggcctcaacc    2100
tactactggg ctgcttccta atgcaggagt cgcataaggg agagcgtcga ccgatgccct    2160
tgagagcctt caacccagtc agctccttcc ggtgggcgcg gggcatgact atcgtcgccg    2220
cacttatgac tgtcttcttt atcatgcaac tcgtaggaca ggtgccggca gcgctctggg    2280
```

```
tcattttcgg cgaggaccgc tttcgctgga gcgcgacgat gatcggcctg tcgcttgcgg   2340
tattcggaat cttgcacgcc ctcgctcaag ccttcgtcac tggtcccgcc accaaacgtt   2400
tcggcgagaa gcaggccatt atcgccggca tggcggccga cgcgctgggc tacgtcttgc   2460
tggcgttcgc gacgcgaggc tggatggcct tccccattat gattcttctc gcttccggcg   2520
gcatcgggat gcccgcgttg caggccatgc tgtccaggca ggtagatgac gaccatcagg   2580
gacagcttca aggatcgctc gcggctctta ccagcctaac ttcgatcact ggaccgctga   2640
tcgtcacggc gatttatgcc gcctcggcga gcacatggaa cgggttggca tggattgtag   2700
gcgccgccct ataccttgtc tgcctcccg cgttgcgtcg cggtgcatgg agccgggcca   2760
cctcgacctg aatggaagcc ggcggcacct cgctaacgga ttcaccactc caagaattgg   2820
agccaatcaa ttcttgcgga gaactgtgaa tgcgcaaacc aacccttggc agaacatatc   2880
catcgcgtcc gccatctcca gcagccgcac gcggcgcatc tcgggcagcg ttgggtcctg   2940
gccacgggtg cgcatgatcg tgctcctgtc gttgaggacc cggctaggct ggcggggttg   3000
ccttactggt tagcagaatg aatcaccgat acgcgagcga acgtgaagcg actgctgctg   3060
caaaacgtct gcgacctgag caacaacatg aatggtcttc ggtttccgtg tttcgtaaag   3120
tctggaaacg cggaagtccc ctacgtgctg ctgaagttgc ccgcaacaga gagtggaacc   3180
aaccggtgat accacgatac tatgactgag agtcaacgcc atgagcggcc tcatttctta   3240
ttctgagtta caacagtccg caccgctgtc cggtagctcc ttccggtggg cgcggggcat   3300
gactatcgtc gccgcactta tgactgtctt ctttatcatg caactcgtag gacaggtgcc   3360
ggcagcgccc aacagtcccc cggccacggg gcctgccacc atacccacgc cgaaacaagc   3420
gccctgcacc attatgttcc ggatctgcat cgcaggatgc tgctggctac cctgtggaac   3480
acctacatct gtattaacga agcgctaacc gttttttatca ggctctggga ggcagaataa   3540
atgatcatat cgtcaattat tacctccacg gggagagcct gagcaaactg gcctcaggca   3600
tttgagaagc acacggtcac actgcttccg gtagtcaata aaccggtaaa ccagcaatag   3660
acataagcgg ctatttaacg accctgccct gaaccgacga ccgggtcgaa tttgctttcg   3720
aatttctgcc attcatccgc ttattatcac ttattcaggc gtagcaccag gcgtttaagg   3780
gcaccaataa ctgccttaaa aaaattacgc cccgccctgc cactcatcgc agtactgttg   3840
taattcatta agcattctgc cgacatggaa gccatcacag acggcatgat gaacctgaat   3900
cgccagcggc atcagcacct tgtcgccttg cgtataatat ttgcccatgg tgaaaacggg   3960
ggcgaagaag ttgtccatat tggccacgtt taaatcaaaa ctggtgaaac tcacccaggg   4020
attggctgag acgaaaaaca tattctcaat aaacccttta gggaaatagg ccaggttttc   4080
accgtaacac gccacatctt gcgaatatat gtgtagaaac tgccggaaat cgtcgtggta   4140
ttcactccag agcgatgaaa acgtttcagt ttgctcatgg aaaacggtgt aacaagggtg   4200
aacactatcc catatcacca gctcaccgtc tttcattgcc atacg              4245
```

<210> SEQ ID NO 25
<211> LENGTH: 47
<212> TYPE: DNA
<213> ORGANISM: Artificial sequence
<220> FEATURE:
<223> OTHER INFORMATION: Primer

<400> SEQUENCE: 25
ggctcagcag cggccgcgct gtccctcctg ttcagctatt gacgggg                    47

<210> SEQ ID NO 26
<211> LENGTH: 55
<212> TYPE: DNA
<213> ORGANISM: Artificial sequence
<220> FEATURE:
<223> OTHER INFORMATION: Primer

<400> SEQUENCE: 26

| | |
|---|---|
| ggctctgacg agctcggtgc tacatttgaa gagataaatt gcactgaaat ctagg | 55 |

<210> SEQ ID NO 27
<211> LENGTH: 3964
<212> TYPE: DNA
<213> ORGANISM: Unknown
<220> FEATURE:
<223> OTHER INFORMATION: Recombinant plasmid pXT1094

<400> SEQUENCE: 27

| | |
|---|---|
| gaattctcat gtttgacagc ttatcatcga taagctttaa tgcggtagtt tatcacagtt | 60 |
| aaattgctaa cgcagtcagg caccgtgtat gaaatctaac aatgcgctca tcgtcatcct | 120 |
| cggcaccgtc accctggatg ctgtaggcat aggcttggtt atgccggtac tgccgggcct | 180 |
| cttgcgggat atcgtccatt ccgacagcat cgccagtcac tatggcgtgc tgctagcgct | 240 |
| atatgcgttg atgcaatttc tatgcgcacc cgttctcgga gcactgtccg accgctttgg | 300 |
| ccgccgccca gtcctgctcg cttcgctact tggagccact atcgactacg cgatcatggc | 360 |
| gaccacaccc gtcctgtgga tcctctacgc cggacgcatc gtggccggca tcaccggcgc | 420 |
| cacaggtgcg gttgctggcg cctatatcgc cgacatcacc gatggggaag atcgggctcg | 480 |
| ccacttcggg ctcatgagcg cttgtttcgg cgtgggtatg gtggcaggcc ccgtggccgg | 540 |
| gggactgttg ggcgccatct ccttgcatgc accattcctt gcggcggcgg tgctcaacgg | 600 |
| cctcaaccta ctactgggct gcttcctaat gcaggagtcg cataagggag agcgtcgacc | 660 |
| gatgcccttg agagccttca acccagtcag ctccttccgg tgggcgcggg gcatgactat | 720 |
| cgtcgccgca cttatgactg tcttctttat catgcaactc gtaggacagg tgccggcagc | 780 |
| gctctgggtc attttcggcg aggaccgctt tcgctggagc gcgacgatga tcggcctgtc | 840 |
| gcttgcggta ttcggaatct tgcacgccct cgctcaagcc ttcgtcactg gtcccgccac | 900 |
| caaacgtttc ggcgagaagc aggccattat cgccggcatg gcggccgacg cgctgggcta | 960 |
| cgtcttgctg gcgttcgcga cgcgaggctg gatggccttc cccattatga ttcttctcgc | 1020 |
| ttccggcggc atcgggatgc ccgcgttgca ggccatgctg tccaggcagg tagatgacga | 1080 |
| ccatcaggga cagcttcaag atcgctcgc ggctcttacc agcctaactt cgatcattgg | 1140 |
| accgctgatc gtcacggcga tttatgccgc ctcggcgagc acatggaacg ggttggcatg | 1200 |
| gattgtaggc gccgccctat accttgtctg cctccccgcg ttgcgtcgcg gtgcatggag | 1260 |
| ccgggccacc tcgacctgaa tggaagccgg cggcacctcg ctaacggatt caccactcca | 1320 |
| agaattggag ccaatcaatt cttgcggaga actgtgaatg cgcaaaccaa cccttggcag | 1380 |
| aacatatcca tcgcgtccgc catctccagc agccgcacgc ggcgcatctc gggcagcgtt | 1440 |
| gggtcctggc cacgggtgcg catgatcgtg ctcctgtcgt tgaggacccg gctaggctgg | 1500 |
| cggggttgcc ttactggtta gcagaatgaa tcaccgatac gcgagcgaac gtgaagcgac | 1560 |
| tgctgctgca aaacgtctgc gacctgagca acaacatgaa tggtcttcgg tttccgtgtt | 1620 |
| tcgtaaagtc tggaaacgcg gaagtcagcg ccctgcacca ttatgttccg gatctgcatc | 1680 |
| gcaggatgct gctggctacc ctgtggaaca cctacatctg tattaacgaa gcgctggcat | 1740 |

```
tgaccctgag tgattttcct ctggtagatc tatgcatgcg ccgcgctgt ccctcctgtt    1800 cagctattga cggggtggtg cgtaacggca aaagcaccgc cggacatcag cgctagcgga    1860
gtgtatactg gcttactatg ttggcactga tgagggtgtc agtgaagtgc ttcatgtggc    1920
aggagaaaaa aggctgcacc ggtgcgtcag cagaatatgt gatacaggat atattccgct    1980
tcctcgctca ctgactcgct acgctcggtc gttcgactgc ggcgagcgga atggcttac     2040 gaacggggcg gagatttcct ggaagatgcc aggaagatac ttaacaggga agtgagaggg    2100
ccgcggcaaa gccgttttc cataggctcc gcccctga caagcatcac gaaatctgac       2160
gctcaaatca gtggtggcga aacccgacag gactataaag ataccaggcg tttccccctg    2220
gcggctccct cgtgcgctct cctgttcctg cctttcggtt taccggtgtc attccgctgt    2280
tatggccgcg tttgtctcat tccacgcctg acactcagtt ccgggtaggc agttcgctcc    2340
aagctggact gtatgcacga acccccgtt cagtccgacc gctgcgcctt atccggtaac     2400
tatcgtcttg agtccaaccc ggaaagacat gcaaaagcac cactggcagc agccactggt    2460
aattgattta gaggagttag tcttgaagtc atgcgccggt taaggctaaa ctgaaggac     2520 aagttttggt gactgcgctc ctccaagcca gttacctcgg ttcaaagagt tggtagctca    2580
gagaaccttc gaaaaaccgc cctgcaaggc ggttttttcg ttttcagagc aagagattac    2640
gcgcagacca aaacgatctc aagaagatca tcttattaat cagataaaat attcctagat    2700
ttcagtgcaa tttatctctt caaatgtagc accgagctca ctagtagatc tggggtctga    2760
cgctcagtgg aacgaaaact cacgttaagg gattttggtc atgagattat caaaaaggat    2820
cttcacctag atccttttaa attaaaaatg aagttttaaa tcaatctaaa gtatatatga    2880
gtaaacttgg tctgacagtt accaatgctt aatcagtgag gcacctatct cagcgatctg    2940
tctatttcgt tcatccatag ttgcctgact ccccgtcgtg tagataacta cgatacggga    3000
gggcttacca tctggcccca gtgctgcaat gataccgcga acccacgct caccggctcc      3060 agatttatca gcaataaacc agccagccgg aagggccgag cgcagaagtg gtcctgcaac    3120
tttatccgcc tccatccagt ctattaattg ttgccgggaa gctagagtaa gtagttcgcc    3180
agttaatagt ttgcgcaacg ttgttgccat tgctgcaggc atcgtggtgt cacgctcgtc    3240
gtttggtatg gcttcattca gctccggttc ccaacgatca aggcgagtta catgatcccc    3300
catgttgtgc aaaaaagcgg ttagctcctt cggtcctccg atcgttgtca gaagtaagtt    3360
ggccgcagtg ttatcactca tggttatggc agcactgcat aattctctta ctgtcatgcc    3420
atccgtaaga tgcttttctg tgactggtga gtactcaacc aagtcattct gagaatagtg    3480
tatgcggcga ccgagttgct cttgcccggc gtcaacacgg ataataccg cccacatag       3540 cagaacttta aaagtgctca tcattggaaa acgttcttcg gggcgaaaac tctcaaggat    3600
cttaccgctg ttgagatcca gttcgatgta acccactcgt gcacccaact gatcttcagc    3660
atcttttact ttcaccagcg tttctgggtg agcaaaaaca ggaaggcaaa atgccgcaaa    3720
aaagggaata agggcgacac ggaaatgttg aatactcata ctcttccttt ttcaatatta    3780
ttgaagcatt tatcagggtt attgtctcat gagcggatac atatttgaat gtatttagaa    3840
aaataaacaa atagggttc cgcgcacatt tccccgaaaa gtgccacctg acgtctaaga    3900
aaccattatt atcatgacat taacctataa aaataggcgt atcacgaggc cctttcgtct    3960
tcaa                                                                 3964
```

<210> SEQ ID NO 28

<211> LENGTH: 4368
<212> TYPE: DNA
<213> ORGANISM: Unknown
<220> FEATURE:
<223> OTHER INFORMATION: Recombinant plasmid pXT1091

<400> SEQUENCE: 28

| | | | | | |
|---|---|---|---|---|---|
| gaattctcat | gtttgacagc | ttatcatcga | taagctttaa | tgcggtagtt | tatcacagtt | 60 |
| aaattgctaa | cgcagtcagg | caccgtgtat | gaaatctaac | aatgcgctca | tcgtcatcct | 120 |
| cggcaccgtc | accctggatg | ctgtaggcat | aggcttggtt | atgccggtac | tgccgggcct | 180 |
| cttgcgggat | atcgtccatt | ccgacagcat | cgccagtcac | tatggcgtgc | tgctagcgct | 240 |
| atatgcgttg | atgcaatttc | tatgcgcacc | cgttctcgga | gcactgtccg | accgctttgg | 300 |
| ccgccgccca | gtcctgctcg | cttcgctact | tggagccact | atcgactacg | cgatcatggc | 360 |
| gaccacaccc | gtcctgtgga | tcctctacgc | cggacgcatc | gtggccggca | tcaccggcgc | 420 |
| cacaggtgcg | gttgctggcg | cctatatcgc | cgacatcacc | gatggggaag | atcgggctcg | 480 |
| ccacttcggg | ctcatgagcg | cttgtttcgg | cgtgggtatg | gtggcaggcc | ccgtggccgg | 540 |
| gggactgttg | ggcgccatct | ccttgcatgc | accattcctt | gcggcggcgg | tgctcaacgg | 600 |
| cctcaaccta | ctactgggct | gcttcctaat | gcaggagtcg | cataagggag | agcgtcgacc | 660 |
| gatgcccttg | agagccttca | acccagtcag | ctccttccgg | tgggcgcggg | gcatgactat | 720 |
| cgtcgccgca | cttatgactg | tcttctttat | catgcaactc | gtaggacagg | tgccggcagc | 780 |
| gctctgggtc | attttcggcg | aggaccgctt | cgctggagc | gcgacgatga | tcggcctgtc | 840 |
| gcttgcggta | ttcggaatct | tgcacgccct | cgctcaagcc | ttcgtcactg | gtcccgccac | 900 |
| caaacgtttc | ggcgagaagc | aggccattat | cgccggcatg | gcggccgacg | cgctgggcta | 960 |
| cgtcttgctg | gcgttcgcga | cgcgaggctg | atggccttc | cccattatga | ttcttctcgc | 1020 |
| ttccggcggc | atcgggatgc | ccgcgttgca | ggccatgctg | tccaggcagg | tagatgacga | 1080 |
| ccatcaggga | cagcttcaag | gatcgctcgc | ggctcttacc | agcctaactt | cgatcattgg | 1140 |
| accgctgatc | gtcacggcga | tttatgccgc | ctcggcgagc | acatggaacg | ggttggcatg | 1200 |
| gattgtaggc | gccgccctat | accttgtctg | cctccccgcg | ttgcgtcgcg | gtgcatggag | 1260 |
| ccgggccacc | tcgacctgaa | tggaagccgg | cggcacctcg | ctaacggatt | caccactcca | 1320 |
| agaattggag | ccaatcaatt | cttgcggaga | actgtgaatg | cgcaaaccaa | cccttggcag | 1380 |
| aacatatcca | tcgcgtccgc | catctccagc | agccgcacgc | ggcgcatctc | gggcagcgtt | 1440 |
| gggtcctggc | cacgggtgcg | catgatcgtg | ctcctgtcgt | tgaggacccg | gctaggctgg | 1500 |
| cggggttgcc | ttactggtta | gcagaatgaa | tcaccgatac | gcgagcgaac | gtgaagcgac | 1560 |
| tgctgctgca | aaacgtctgc | gacctgagca | acaacatgaa | tggtcttcgg | tttccgtgtt | 1620 |
| tcgtaaagtc | tggaaacgcg | gaagtcagcg | ccctgcacca | ttatgttccg | gatctgcatc | 1680 |
| gcaggatgct | gctggctacc | ctgtggaaca | cctacatctg | tattaacgaa | gcgctggcat | 1740 |
| tgaccctgag | tgatttttct | ctggtagatc | tatgcatgcg | gccgccccgc | cgcatccata | 1800 |
| ccgccagttg | tttaccctca | caacgttcca | gtaaccgggc | atgttcatca | tcagtaaccc | 1860 |
| gtatcgtgag | catcctctct | cgtttcatcg | gtatcattac | ccccatgaac | agaaatcccc | 1920 |
| cttacacgga | ggcatcagtg | accaaacagg | aaaaaaccgc | ccttaacatg | gcccgcttta | 1980 |
| tcagaagcca | gacattaacg | cttctggaga | aactcaacga | gctggacgcg | gatgaacagg | 2040 |
| cagacatctg | tgaatcgctt | cacgaccacg | ctgatgagct | ttaccgcagc | tgcctcgcgc | 2100 |
| gtttcggtga | tgacggtgaa | aacctctgac | acatgcagct | cccggagacg | gtcacagctt | 2160 |

```
gtctgtaagc ggatgccggg agcagacaag cccgtcaggg cgcgtcagcg ggtgttggcg    2220
ggtgtcgggg cgcagccatg acccagtcac gtagcgatag cggagtgtat actggcttac    2280
tatgttggca ctgatgaggg tgtcagtgaa gtgcttcatg tggcaggaga aaaaaggctg    2340
caccggtgcg tcagcagaat atgtgataca ggatatattc cgcttcctcg ctcactgact    2400
cgctacgctc ggtcgttcga ctgcggcgag cggaaatggc ttacgaacgg ggcggagatt    2460
tcctggaaga tgccaggaag atacttaaca gggaagtgag agggccgcgg caaagccgtt    2520
tttccatagg ctccgccccc ctgacaagca tcacgaaatc tgacgctcaa atcagtggtg    2580
gcgaaacccg acaggactat aaagatacca ggcgtttccc cctggcggct ccctcgtgcg    2640
ctctcctgtt cctgcctttc ggtttaccgg tgtcattccg ctgttatggc cgcgtttgtc    2700
tcattccacg cctgacactc agttccgggt aggcagttcg ctccaagctg actgtatgc    2760 acgaaccccc cgttcagtcc gaccgctgcg ccttatccgg taactatcgt cttgagtcca    2820
acccggaaag acatgcaaaa gcaccactgg cagcagccac tggtaattga tttagaggag    2880
ttagtcttga agtcatgcgc cggttaaggc taaactgaaa ggacaagttt tggtgactgc    2940
gctcctccaa gccagttacc tcggttcaaa gagttggtag ctcagagaac cttcgaaaaa    3000
ccgccctgca aggcggtttt tcgtttttca gagcaagaga ttacgcgcag accaaaacga    3060
tctcaagaag atcatcttat taatcagata aatattcct agatttcagt gcaatttatc    3120
tcttcaaatg tagcaccgag ctcactagta gatctggggt ctgacgctca gtggaacgaa    3180
aactcacgtt aagggatttt ggtcatgaga ttatcaaaaa ggatcttcac ctagatcctt    3240
ttaaattaaa aatgaagttt taaatcaatc taaagtatat atgagtaaac ttggtctgac    3300
agttaccaat gcttaatcag tgaggcacct atctcagcga tctgtctatt cgttcatcc    3360 atagttgcct gactccccgt cgtgtagata actacgatac gggagggctt accatctggc    3420
cccagtgctg caatgatacc gcgagaccca cgctcaccgg ctccagattt atcagcaata    3480
aaccagccag ccggaagggc cgagcgcaga agtggtcctg caactttatc cgcctccatc    3540
cagtctatta attgttgccg ggaagctaga gtaagtagtt cgccagttaa tagtttgcgc    3600
aacgttgttg ccattgctgc aggcatcgtg gtgtcacgct cgtcgtttgg tatggcttca    3660
ttcagctccg gttcccaacg atcaaggcga gttacatgat ccccatgtt gtgcaaaaaa    3720 gcggttagct ccttcggtcc tccgatcgtt gtcagaagta agttggccgc agtgttatca    3780
ctcatggtta tggcagcact gcataattct cttactgtca tgccatccgt aagatgcttt    3840
tctgtgactg gtgagtactc aaccaagtca ttctgagaat agtgtatgcg gcgaccgagt    3900
tgctcttgcc cggcgtcaac acgggataat accgcgccac atagcagaac tttaaaagtg    3960
ctcatcattg gaaaacgttc ttcggggcga aaactctcaa ggatcttacc gctgttgaga    4020
tccagttcga tgtaacccac tcgtgcaccc aactgatctt cagcatcttt tactttcacc    4080
agcgtttctg ggtgagcaaa aacaggaagg caaaatgccg caaaaaaggg aataagggcg    4140
acacggaaat gttgaatact catactcttc ctttttcaat attattgaag catttatcag    4200
ggttattgtc tcatgagcgg atacatattt gaatgtattt agaaaaataa acaaataggg    4260
gttccgcgca catttccccg aaaagtgcca cctgacgtct aagaaaccat tattatcatg    4320
acattaacct ataaaaatag gcgtatcacg aggccctttc gtcttcaa    4368
```

<210> SEQ ID NO 29
<211> LENGTH: 4742
<212> TYPE: DNA

<213> ORGANISM: Unknown
<220> FEATURE:
<223> OTHER INFORMATION: Recombinant plasmid pXT1221

<400> SEQUENCE: 29

```
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact ggagccact atcgactacg cgatcatggc     360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtggcaggcc ccgtggccgg     540
gggactgttg ggcgccatct ccttgcatgc accattcctt gcgcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
gctctgggtc attttcggcg aggaccgctt tcgctggagc gcgacgatga tcggcctgtc     840
gcttgcggta ttcggaatct tgcacgccct cgctcaagcc ttcgtcactg gtcccgccac     900
caaacgtttc ggcgagaagc aggccattat cgccggcatg gcggccgacg cgctgggcta     960
cgtcttgctg gcgttcgcga cgcgaggctg gatggccttc cccattatga ttcttctcgc    1020
ttccggcgga atcgggatgc ccgcgttgca ggccatgctg tccaggcagg tagatgacga    1080
ccatcaggga cagcttcaag gatcgctcgc ggctcttacc agcctaactt cgatcattgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
agaattggag ccaatcaatt cttgcggaga actgtgaatg cgcaaaccaa cccttggcag    1380
aacatatcca tcgcgtccgc catctccagc agccgcacgc ggcgcatctc gggcagcgtt    1440
gggtcctggc cacgggtgcg catgatcgtg ctcctgtcgt tgaggacccg gctaggctgg    1500
cggggttgcc ttactggtta gcagaatgaa tcaccgatac gcgagcgaac gtgaagcgac    1560
tgctgctgca aaacgtctgc gacctgagca acaacatgaa tggtcttcgg tttccgtgtt    1620
tcgtaaagtc tggaaacgcg gaagtcagcg ccctgcacca ttatgttccg gatctgcatc    1680
gcaggatgct gctggctacc ctgtggaaca cctacatctg tattaacgaa gcgctggcat    1740
tgaccctgag tgattttcct ctggtagatc tatgcatgtt atccctagaa cgggagcgtc    1800
agccggaaat acaggaacgc acgctggatg gcccttcgct gggatggtga aaccatgaaa    1860
aatggcagct tcagtggatt aagtgggggt aatgtggcct gtaccctctg gttgcatagg    1920
tattcatacg gttaaaattt atcaggcgcg atcgcggcag ttttcgggt ggtttgttgc     1980
cattttacc tgtctgctgc cgtgatcgcg ctgaacgcgt tttagcggtg cgtacaatta    2040
agggattatg gtaaatccac ttactgtctg ccctcgtagc catcgagata aaccgcacga    2100
aatcgtgtca gccagcagcc gcggccgccc cgccgcatcc ataccgccag ttgtttaccc    2160
tcacaacgtt ccagtaaccg ggcatgttca tcatcagtaa cccgtatcgt gagcatcctc    2220
```

```
tctcgtttca tcggtatcat taccccatg aacagaaatc ccccttacac ggaggcatca    2280
gtgaccaaac aggaaaaaac cgcccttaac atggcccgct ttatcagaag ccagacatta    2340
acgcttctgg agaaactcaa cgagctggac gcggatgaac aggcagacat ctgtgaatcg    2400
cttcacgacc acgctgatga gctttaccgc agctgcctcg cgcgtttcgg tgatgacggt    2460
gaaaacctct gacacatgca gctcccggag acggtcacag cttgtctgta agcggatgcc    2520
gggagcagac aagcccgtca gggcgcgtca gcgggtgttg gcgggtgtcg gggcgcagcc    2580
atgacccagt cacgtagcga tagcggagtg tatactggct taactatgcg gcatcagagc    2640
agattgtact gagagtgcac catatgcggt gtgaaatacc gcacagatgc gtaaggagaa    2700
aataccgcat caggcgctct tccgcttcct cgctcactga ctcgctgcgc tcggtcgttc    2760
ggctgcggcg agcggtatca gctcactcaa aggcggtaat acggttatcc acagaatcag    2820
gggataacgc aggaaagaac atgtgagcaa aaggccagca aaaggccagg aaccgtaaaa    2880
aggccgcgtt gctggcgttt ttccataggc tccgcccccc tgacgagcat cacaaaaatc    2940
gacgctcaag tcagaggtgg cgaaacccga caggactata agataccag gcgtttcccc    3000 ctggaagctc cctcgtgcgc tctcctgttc cgaccctgcc gcttaccgga tacctgtccg    3060
cctttctccc ttcgggaagc gtggcgcttt ctcatagctc acgctgtagg tatctcagtt    3120
cggtgtaggt cgttcgctcc aagctgggct gtgtgcacga accccccgtt cagcccgacc    3180
gctgcgcctt atccggtaac tatcgtcttg agtccaaccc ggtaagacac gacttatcgc    3240
cactggcagc agccactggt aacaggatta gcagagcgag gtatgtaggc ggtgctacag    3300
agttcttgaa gtggtggcct aactacggct acactagaag gacagtattt ggtatctgcg    3360
ctctgctgaa gccagttacc ttcggaaaaa gagttggtag ctcttgatcc ggcaaacaaa    3420
ccaccgctgg tagcggtggt ttttttgttt gcaagcagca gattacgcgc agaaaaaaag    3480
gatctcaaga agatccttg atcttttcta cgagctcact cagtagatctg gggtctgacg    3540 ctcagtggaa cgaaaactca cgttaaggga ttttggtcat gagattatca aaaaggatct    3600
tcacctagat ccttttaaat taaaaatgaa gttttaaatc aatctaaagt atatatgagt    3660
aaacttggtc tgacagttac caatgcttaa tcagtgaggc acctatctca gcgatctgtc    3720
tatttcgttc atccatagtt gcctgactcc ccgtcgtgta gataactacg atacgggagg    3780
gcttaccatc tggccccagt gctgcaatga taccgcgaga cccacgctca ccggctccag    3840
atttatcagc aataaaccag ccagccggaa gggccgagcg cagaagtggt cctgcaactt    3900
tatccgcctc catccagtct attaattgtt gccgggaagc tagagtaagt agttcgccag    3960
ttaatagttt gcgcaacgtt gttgccattg ctgcaggcat cgtggtgtca cgctcgtcgt    4020
ttggtatggc ttcattcagc tccggttccc aacgatcaag gcgagttaca tgatccccca    4080
tgttgtgcaa aaaagcggtt agctccttcg gtcctccgat cgttgtcaga agtaagttgg    4140
ccgcagtgtt atcactcatg gttatggcag cactgcataa ttctcttact gtcatgccat    4200
ccgtaagatg cttttctgtg actggtgagt actcaaccaa gtcattctga aatagtgta    4260 tgcggcgacc gagttgctct tgcccggcgt caacacggga taataccgcg ccacatagca    4320
gaactttaaa agtgctcatc attggaaaac gttcttcggg gcgaaaactc tcaaggatct    4380
taccgctgtt gagatccagt tcgatgtaac ccactcgtgc acccaactga tcttcagcat    4440
cttttacttt caccagcgtt tctgggtgag caaaaacagg aaggcaaaat gccgcaaaaa    4500
agggaataag ggcgacacgg aaatgttgaa tactcatact cttcctttt caatattatt    4560
```

```
gaagcattta tcagggttat tgtctcatga gcggatacat atttgaatgt atttagaaaa      4620
ataaacaaat aggggttccg cgcacatttc cccgaaaagt gccacctgac gtctaagaaa      4680
ccattattat catgacatta acctataaaa ataggcgtat cacgaggccc tttcgtcttc      4740
aa                                                                    4742

<210> SEQ ID NO 30
<211> LENGTH: 20
<212> TYPE: DNA
<213> ORGANISM: Artificial sequence
<220> FEATURE:
<223> OTHER INFORMATION: BglII NsiI NotI multiple cloning site

<400> SEQUENCE: 30
agatctatgc atgcggccgc                                                 20

<210> SEQ ID NO 31
<211> LENGTH: 18
<212> TYPE: DNA
<213> ORGANISM: Artificial sequence
<220> FEATURE:
<223> OTHER INFORMATION: SacI SpeI BglII multiple cloning site

<400> SEQUENCE: 31
gagctcacta gtagatct                                                   18

<210> SEQ ID NO 32
<211> LENGTH: 398
<212> TYPE: DNA
<213> ORGANISM: Unknown
<220> FEATURE:
<223> OTHER INFORMATION: cer site on the plasmid pXT1007

<400> SEQUENCE: 32
atgcatgtta tccctagaac gggagcgtca gccggaaata caggaacgca cgctggatgg      60
cccttcgctg ggatggtgaa accatgaaaa atggcagctt cagtggatta agtggggta     120 atgtggcctg taccctctgg ttgcataggt attcatacgg ttaaaattta tcaggcgcga    180
tcgcggcagt ttttcgggtg gtttgttgcc attttacct gtctgctgcc gtgatcgcgc     240
tgaacgcgtt ttagcggtgc gtacaattaa gggattatgg taaatccact tactgtctgc    300
cctcgtagcc atcgagataa accgcacgaa atcgtgtcag ccagcagccg cggccgccct    360
ataaaaatag gcgtatcacg aggccctttc gtcttcaa                            398

<210> SEQ ID NO 33
<211> LENGTH: 4399
<212> TYPE: DNA
<213> ORGANISM: Unknown
<220> FEATURE:
<223> OTHER INFORMATION: Recombinant plasmid pXT1092

<400> SEQUENCE: 33
gaattctcat gtttgacagc ttatcatcga taagctttaa tgcggtagtt tatcacagtt      60
aaattgctaa cgcagtcagg caccgtgtat gaaatctaac aatgcgctca tcgtcatcct    120
cggcaccgtc accctggatg ctgtaggcat aggcttggtt atgccggtac tgccgggcct    180
cttgcgggat atcgtccatt ccgacagcat cgccagtcac tatggcgtgc tgctagcgct    240
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcctctacgc cggacgcatc gtggccggca tcaccggcgc    420
```

```
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt gcggcggcgg tgctcaacgg    600
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt tcgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg atggccttc cccattatga ttcttctcgc    1020
ttccggcggc atcgggatgc ccgcgttgca ggccatgctg tccaggcagg tagatgacga    1080
ccatcaggga cagcttcaag gatcgctcgc ggctcttacc agcctaactt cgatcattgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
agaattggag ccaatcaatt cttgcggaga actgtgaatg cgcaaaccaa cccttgcag    1380
aacatatcca tcgcgtccgc catctccagc agccgcacgc ggcgcatctc gggcagcgtt    1440
gggtcctggc cacgggtgcg catgatcgtg ctcctgtcgt tgaggacccg gctaggctgg    1500
cggggttgcc ttactggtta gcagaatgaa tcaccgatac gcgagcgaac gtgaagcgac    1560
tgctgctgca aaacgtctgc gacctgagca acaacatgaa tggtcttcgg tttccgtgtt    1620
tcgtaaagtc tggaaacgcg gaagtcagcg ccctgcacca ttatgttccg gatctgcatc    1680
gcaggatgct gctggctacc ctgtggaaca cctacatctg tattaacgaa gcgctggcat    1740
tgaccctgag tgatttttct ctggtagatc tactagtgag ctcgtagaaa agatcaaagg    1800
atcttcttga gatccttttt ttctgcgcgt aatctgctgc ttgcaaacaa aaaaaccacc    1860
gctaccagcg gtggtttgtt tgccggatca agagctacca actctttttc cgaaggtaac    1920
tggcttcagc agagcgcaga taccaaatac tgtccttcta gtgtagccgt agttaggcca    1980
ccacttcaag aactctgtag caccgcctac atacctcgct ctgctaatcc tgttaccagt    2040
ggctgctgcc agtggcgata agtcgtgtct taccgggttg gactcaagac gatagttacc    2100
ggataaggcg cagcggtcgg gctgaacggg ggttcgtgc acacagccca gcttggagcg    2160
aacgacctac accgaactga gatacctaca gcgtgagcta tgagaaagcg ccacgcttcc    2220
cgaagggaga aaggcggaca ggtatccggt aagcggcagg gtcggaacag gagagcgcac    2280
gagggagctt ccaggggggaa acgcctggta tctttatagt cctgtcgggt ttcgccacct    2340
ctgacttgag cgtcgatttt tgtgatgctc gtcaggggg cggagcctat ggaaaaacgc    2400
cagcaacgcg gcctttttac ggttcctggc cttttgctgg ccttttgctc acatgttctt    2460
tcctgcgtta tcccctgatt ctgtggataa ccgtattacc gcctttgagt gagctgatac    2520
cgctcgccgc agccgaacga ccgagcgcag cgagtcagtg agcgaggaag cggaagagcg    2580
cctgatgcgg tattttctcc ttacgcatct gtgcggtatt tcacaccgca tatggtgcac    2640
tctcagtaca atctgctctg atgccgcata gttaagccag tatacactcc gctatcgcta    2700
cgtgactggg tcatggctgc gccccgacac ccgccaacac ccgctgacgc gccctgacgg    2760
```

```
gcttgtctgc tcccggcatc cgcttacaga caagctgtga ccgtctccgg gagctgcatg    2820
tgtcagaggt tttcaccgtc atcaccgaaa cgcgcgaggc agctgcggta aagctcatca    2880
gcgtggtcgt gaagcgattc acagatgtct gcctgttcat ccgcgtccag ctcgttgagt    2940
ttctccagaa gcgttaatgt ctggcttctg ataaagcggg ccatgttaag ggcggttttt    3000
tcctgtttgg tcactgatgc ctccgtgtaa gggggatttc tgttcatggg ggtaatgata    3060
ccgatgaaac gagagaggat gctcacgata cgggttactg atgatgaaca tgcccggtta    3120
ctggaacgtt gtgagggtaa acaactggcg gtatggatgc ggcggggcgg ccgcatgcat    3180
agatctgggg tctgacgctc agtggaacga aaactcacgt taagggattt tggtcatgag    3240
attatcaaaa aggatcttca cctagatcct tttaaattaa aaatgaagtt ttaaatcaat    3300
ctaaagtata tatgagtaaa cttggtctga cagttaccaa tgcttaatca gtgaggcacc    3360
tatctcagcg atctgtctat ttcgttcatc catagttgcc tgactccccg tcgtgtagat    3420
aactacgata cgggagggct taccatctgg ccccagtgct gcaatgatac cgcgagaccc    3480
acgctcaccg gctccagatt tatcagcaat aaaccagcca gccggaaggg ccgagcgcag    3540
aagtggtcct gcaactttat ccgcctccat ccagtctatt aattgttgcc gggaagctag    3600
agtaagtagt tcgccagtta atagtttgcg caacgttgtt gccattgctg caggcatcgt    3660
ggtgtcacgc tcgtcgtttg gtatggcttc attcagctcc ggttcccaac gatcaaggcg    3720
agttacatga tcccccatgt tgtgcaaaaa agcggttagc tccttcggtc ctccgatcgt    3780
tgtcagaagt aagttggccg cagtgttatc actcatggtt atggcagcac tgcataattc    3840
tcttactgtc atgccatccg taagatgctt ttctgtgact ggtgagtact caaccaagtc    3900
attctgagaa tagtgtatgc ggcgaccgag ttgctcttgc ccggcgtcaa cacgggataa    3960
taccgcgcca catagcagaa ctttaaaagt gctcatcatt ggaaaacgtt cttcggggcg    4020
aaaactctca aggatcttac cgctgttgag atccagttcg atgtaaccca ctcgtgcacc    4080
caactgatct tcagcatctt ttactttcac cagcgtttct gggtgagcaa aaacaggaag    4140
gcaaaatgcc gcaaaaaagg gaataagggc gacacggaaa tgttgaatac tcatactctt    4200
cctttttcaa tattattgaa gcatttatca gggttattgt ctcatgagcg gatacatatt    4260
tgaatgtatt tagaaaaata acaaataggg gttccgcgc acatttcccc gaaaagtgcc    4320
acctgacgtc taagaaacca ttattatcat gacattaacc tataaaaata ggcgtatcac    4380
gaggcccttt cgtcttcaa                                                4399
```

<210> SEQ ID NO 34
<211> LENGTH: 5308
<212> TYPE: DNA
<213> ORGANISM: Unknown
<220> FEATURE:
<223> OTHER INFORMATION: Recombinant plasmid pXT1109

<400> SEQUENCE: 34

```
gaattctact gtatgagcat acagttaagg gttgacaacc gatatttatt cacttaatat     60
ataaatatca actgaggcgc gcccataaca tcaagaggat atgaaattat gtttccagcc    120
atgagcttgt ccggactctt tgccaatgct gtactccggg ctcagcacct gcatcagctg    180
gctgctgaca ccttcaaaga gtttgagcgc acctacatcc cggagggaca gcgttactcc    240
atccagaaca cccaggttgc cttctgcttc tctgaaacca tcccggcccc gacgggcaag    300
aatgaggccc agcagaaatc agactggag ctgcttcgca tctcactgct cctcatccag    360
agctggcttg ggccgctgca gttcctcagc cgtgtcttca ccaacagctt ggtgtttggc    420
```

```
accagcgacc gtgtctatga gaagctgaag gacctggagg aaggcatcct ggccctgatg    480
cgtgagctgg aagatggcac cccgcgtgct gggcagatcc tcaagcagac ctatgacaaa    540
tttgacacaa acatgcgcag tgacgacgcg ctgctcaaga actacggtct gctctcctgc    600
ttccgtaagg acctgcataa gacggagacg tacctgcgtg tcatgaagtg ccgccgcttc    660
ggggaggcga gctgcgcctt ctaatagctc gagtctagac tcactcatta ggcaccccag    720
gctttacact ttatgcttcc ggctcgtata atgtgtggaa ttgtgagcgg ataacaattt    780
cacacaggaa aaagctgatt gcccttcacc gcctggcctc cgttgagcca tctggatcgg    840
cagcgttgtc ttcatcaacc ggaacgagca tgccggagag cagctcactc attaggcacc    900
ccaggcttta cactttatgc ttccggctcg tataatgtgt ggaattgtga gcggataaca    960
atttcacaca gaagctttaa tgcggtagtt tatcacagtt aaattgctaa cgcagtcagg   1020
caccgtgtat gaaatctaac aatgcgctca tcgtcatcct cggcaccgtc accctggatg   1080
ctgtaggcat aggcttggtt atgccggtac tgccgggcct cttgcgggat atcgtccatt   1140
ccgacagcat cgccagtcac tatggcgtgc tgctagcgct atatgcgttg atgcaatttc   1200
tatgcgcacc cgttctcgga gcactgtccg accgctttgg ccgccgccca gtcctgctcg   1260
cttcgctact tggagccact atcgactacg cgatcatggc gaccacaccc gtcctgtgga   1320
tcctctacgc cggacgcatc gtggccggca tcaccggcgc cacaggtgcg gttgctggcg   1380
cctatatcgc cgacatcacc gatggggaag atcgggctcg ccacttcggg ctcatgagcg   1440
cttgtttcgg cgtgggtatg gtggcaggcc ccgtggccgg gggactgttg ggcgccatct   1500
ccttgcatgc accattcctt gcggcggcgg tgctcaacgg cctcaaccta ctactgggct   1560
gcttcctaat gcaggagtcg cataaggag agcgtcgacc gatgcccttg agagccttca   1620
acccagtcag ctccttccgg tgggcgcggg gcatgactat cgtcgccgca cttatgactg   1680
tcttctttat catgcaactc gtaggacagg tgccggcagc gctctgggtc attttcggcg   1740
aggaccgctt tcgctggagc gcgacgatga tcggcctgtc gcttgcggta ttcggaatct   1800
tgcacgccct cgctcaagcc ttcgtcactg gtcccgccac caaacgtttc ggcgagaagc   1860
aggccattat cgccggcatg gcggccgacg cgctgggcta cgtcttgctg gcgttcgcga   1920
cgcgaggctg gatggccttc cccattatga ttcttctcgc ttccggcggc atcgggatgc   1980
ccgcgttgca ggccatgctg tccaggcagg tagatgacga ccatcaggga cagcttcaag   2040
gatcgctcgc ggctcttacc agcctaactt cgatcattgg accgctgatc gtcacggcga   2100
tttatgccgc ctcggcgagc acatggaacg ggttggcatg gattgtaggc gccgccctat   2160
accttgtctg cctccccgcg ttgcgtcgcg gtgcatggag ccgggccacc tcgacctgaa   2220
tggaagccgg cggcacctcg ctaacggatt caccactcca agaattggag ccaatcaatt   2280
cttgcggaga actgtgaatg cgcaaaccaa cccttggcag aacatatcca tcgcgtccgc   2340
catctccagc agccgcacgc ggcgcatctc gggcagcgtt gggtcctggc cacgggtgcg   2400
catgatcgtg ctcctgtcgt tgaggacccg gctaggctgg cggggttgcc ttactggtta   2460
gcagaatgaa tcaccgatac gcgagcgaac gtgaagcgac tgctgctgca aaacgtctgc   2520
gacctgagca acaacatgaa tggtcttcgg tttccgtgtt tcgtaaagtc tggaaacgcg   2580
gaagtcagcg ccctgcacca ttatgttccg gatctgcatc gcaggatgct gctggctacc   2640
ctgtggaaca cctacatctg tattaacgaa gcgctggcat tgaccctgag tgatttttct   2700
ctggtagatc tatgcatgcg gccgccccgc cgcatccata ccgccagttg tttaccctca   2760
```

```
caacgttcca gtaaccgggc atgttcatca tcagtaaccc gtatcgtgag catcctctct   2820
cgtttcatcg gtatcattac ccccatgaac agaaatcccc cttacacgga ggcatcagtg   2880
accaaacagg aaaaaaccgc ccttaacatg gcccgcttta tcagaagcca gacattaacg   2940
cttctggaga aactcaacga gctggacgcg gatgaacagg cagacatctg tgaatcgctt   3000
cacgaccacg ctgatgagct ttaccgcagc tgcctcgcgc gtttcggtga tgacggtgaa   3060
aacctctgac acatgcagct cccggagacg gtcacagctt gtctgtaagc ggatgccggg   3120
agcagacaag cccgtcaggg cgcgtcagcg ggtgttggcg ggtgtcgggg cgcagccatg   3180
acccagtcac gtagcgatag cggagtgtat actggcttac tatgttggca ctgatgaggg   3240
tgtcagtgaa gtgcttcatg tggcaggaga aaaaaggctg caccggtgcg tcagcagaat   3300
atgtgataca ggatatattc cgcttcctcg ctcactgact cgctacgctc ggtcgttcga   3360
ctgcggcgag cggaaatggc ttacgaacgg ggcggagatt tcctggaaga tgccaggaag   3420
atacttaaca gggaagtgag agggccgcgg caaagccgtt tttccatagg ctccgccccc   3480
ctgacaagca tcacgaaatc tgacgctcaa atcagtggtg gcgaaacccg acaggactat   3540
aaagatacca ggcgtttccc cctggcggct ccctcgtgcg ctctcctgtt cctgcctttc   3600
ggtttaccgg tgtcattccg ctgttatggc cgcgtttgtc tcattccacg cctgacactc   3660
agttccgggt aggcagttcg ctccaagctg gactgtatgc acgaaccccc cgttcagtcc   3720
gaccgctgcg ccttatccgg taactatcgt cttgagtcca acccggaaag acatgcaaaa   3780
gcaccactgg cagcagccac tggtaattga tttagaggag ttagtcttga agtcatgcgc   3840
cggttaaggc taaactgaaa ggacaagttt tggtgactgc gctcctccaa gccagttacc   3900
tcggttcaaa gagttggtag ctcagagaac cttcgaaaaa ccgccctgca aggcggtttt   3960
ttcgttttca gagcaagaga ttacgcgcag accaaaacga tctcaagaag atcatcttat   4020
taatcagata aaatattcct agatttcagt gcaatttatc tcttcaaatg tagcaccgag   4080
ctcactagta gatctggggt ctgacgctca gtggaacgaa aactcacgtt aagggatttt   4140
ggtcatgaga ttatcaaaaa ggatcttcac ctagatcctt ttaaattaaa aatgaagttt   4200
taaatcaatc taaagtatat atgagtaaac ttggtctgac agttaccaat gcttaatcag   4260
tgaggcacct atctcagcga tctgtctatt tcgttcatcc atagttgcct gactccccgt   4320
cgtgtagata actacgatac gggagggctt accatctggc cccagtgctg caatgatacc   4380
gcgagaccca cgctcaccgg ctccagattt atcagcaata aaccagccag ccggaagggc   4440
cgagcgcaga agtggtcctg caactttatc cgcctccatc cagtctatta attgttgccg   4500
ggaagctaga gtaagtagtt cgccagttaa tagtttgcgc aacgttgttg ccattgctgc   4560
aggcatcgtg gtgtcacgct cgtcgtttgg tatggcttca ttcagctccg gttcccaacg   4620
atcaaggcga gttacatgat cccccatgtt gtgcaaaaaa gcggttagct ccttcggtcc   4680
tccgatcgtt gtcagaagta agttggccgc agtgttatca ctcatggtta tggcagcact   4740
gcataattct cttactgtca tgccatccgt aagatgcttt tctgtgactg gtgagtactc   4800
aaccaagtca ttctgagaat agtgtatgcg gcgaccgagt tgctcttgcc cggcgtcaac   4860
acgggataat accgcgccac atagcagaac tttaaaagtg ctcatcattg gaaaacgttc   4920
ttcgggcga aaactctcaa ggatcttacc gctgttgaga tccagttcga tgtaacccac   4980
tcgtgcaccc aactgatctt cagcatcttt tactttcacc agcgtttctg ggtgagcaaa   5040
aacaggaagg caaaatgccg caaaaaaggg aataagggcg acacggaaat gttgaatact   5100
catactcttc ctttttcaat attattgaag catttatcag ggttattgtc tcatgagcgg   5160
```

-continued

```
atacatattt gaatgtattt agaaaaataa acaaataggg gttccgcgca catttccccg    5220
aaaagtgcca cctgacgtct aagaaaccat tattatcatg acattaacct ataaaaatag    5280
gcgtatcacg aggccctttc gtcttcaa                                       5308
```

The invention claimed is:

1. A hybrid origin of replication comprising, at least 200 nucleotides from nucleotide sequences from an origin of replication from a first plasmid contiguously linked to nucleotide sequences from an origin of replication from a second plasmid–wherein the first plasmid is selected from the group consisting of pBR322, pACYC184, pACYC177, ColE1, pBR3286, pI, pBR26, pBR313, pPIGDM1, pPVUI, pF, pSC101 and pC101p-157, and wherein the origin of replication from the first plasmid and the origin of replication from the second plasmid differ from one another.

2. The hybrid origin of replication of claim 1 comprising at least 200 nucleotides from nucleotide sequences from a pBR322 origin of replication.

3. The hybrid origin of replication of claim 1 comprising at least 200 nucleotides from nucleotide sequences from a ColE1 origin of replication.

4. The hybrid origin of replication of claim 1 comprising at least 200 nucleotides from nucleotide sequences from a pACYC184 origin of replication.

5. The hybrid origin of replication of claim 1 comprising at least 200 nucleotides from nucleotide sequences from a pACYC184 origin of replication, the remaining nucleotides being from a pBR322 origin of replication.

6. The hybrid origin of replication of claim 1 comprising at least 200 nucleotides from nucleotide sequences from a pBR322 origin of replication, the remaining nucleotides being from a pACYC184 origin of replication.

7. The hybrid origin of replication of claim 1 comprising at least 200 nucleotides from nucleotide sequences from a pBR322 origin of replication, the remaining nucleotides being from a ColE1 origin of replication.

8. The hybrid origin of replication of claim 1 comprising at least 200 nucleotides from nucleotide sequences from a ColE1 origin of replication, the remaining nucleotides being from a pACYC184 origin of replication.

9. The hybrid origin of replication of claim 1 comprising at least 200 nucleotides from nucleotide sequences from a pACYC184 origin of replication, the remaining nucleotides being from a ColE1 origin of replication.

10. The hybrid origin of replication of claim 1 comprising at least 250 nucleotides from nucleotide sequences from a pBR322 origin of replication.

11. The hybrid origin of replication of claim 1 comprising at least 250 nucleotides from nucleotide sequences from a ColE1 origin of replication.

12. The hybrid origin of replication of claim 1 comprising at least 250 nucleotides from nucleotide sequences from a pACYC184 origin of replication.

13. The hybrid origin of replication of claim 1 comprising at least 250 nucleotides from nucleotide sequences from an origin of replication from a plasmid selected from the group consisting of pBR322, pACYC184, pACYC177, ColE1, pBR3286, pI, pBR26, pBR313, pPIGDM1, pPVUI, pF, pSC101 and pC101p-157.

14. The hybrid origin of replication of claim 1 comprising at least 250 nucleotides from nucleotide sequences from a pACYC184 origin of replication, the remaining nucleotides being from a pBR322 origin of replication.

15. The hybrid origin of replication of claim 1 comprising at least 250 nucleotides from nucleotide sequences from a pBR322 origin of replication, the remaining nucleotides being from a pACYC184 origin of replication.

16. The hybrid origin of replication of claim 1 comprising at least 250 nucleotides from nucleotide sequences from a pBR322 origin of replication, the remaining nucleotides being from a ColE1 origin of replication.

17. The hybrid origin of replication of claim 1 comprising at least 250 nucleotides from nucleotide sequences from a ColE1 origin of replication, the remaining nucleotides being from a pACYC184 origin of replication.

18. The hybrid origin of replication of claim 1 comprising at least 250 nucleotides from nucleotide sequences from a pACYC184 origin of replication, the remaining nucleotides being from a ColE1 origin of replication.

19. A hybrid origin of replication comprising, at least 200 nucleotides from nucleotide sequences from an origin of replication from a first plasmid contiguously linked to nucleotide sequences from an origin of replication from a second plasmid, wherein the origin of replication from the first plasmid exhibits at least 70% nucleotide sequence identity with the origin of replication from the second plasmid and wherein the first plasmid is selected from the group consisting of pBR322, pACYC184, pACYC177, ColE1, pBR3286, pI, pBR26, pBR313, pPIGDM1, pPVUI, pF, pSC101 and pC101p-157, and wherein the origin of replication from the first plasmid and the origin of replication from the second plasmid differ from one another.

20. The hybrid origin of replication of claim 1, wherein said hybrid origin of replication is comprised within SEQ ID NO:7 or 12.

21. The hybrid origin of replication of claim 1 comprising nucleotide sequences from pBR322 and nucleotide sequences from ColE1.

22. The hybrid origin of replication of claim 21 wherein a portion of sequence between nucleotide positions 1766 to 3148 of pBR322 (SEQ ID NO:1) is replaced with at least 200 contiguous nucleotides from ColE1 (SEQ ID NO:6).

23. The hybrid origin of replication of claim 21 comprising nucleotide sequences from position 1766 to the AlwNI restriction site in pBR322 (SEQ ID NO:1) contiguously linked to nucleotide sequences from an AlwNI restriction site to position 3148 in ColE1 (SEQ ID NO:6).

24. The hybrid origin of replication of claim 21 comprising nucleotide sequences from position 1766 to an AlwNI restriction site in ColE1 (SEQ ID NO:6) contiguously linked to nucleotide sequences from the AlwNI restriction site to position 3148 in pBR322 (SEQ ID NO: 1).

25. The hybrid origin of replication of claim 1 comprising sequences from the origin of replication from pBR322 contiguously linked to sequences from an origin of replication from ColE1 or pACYC184.

26. The hybrid origin of replication of claim 1 comprising nucleotide sequences from pACYC184 contiguously linked to nucleotide sequences from ColE1.

27. The hybrid origin of replication of claim 1, wherein the hybrid origin of replication is flanked on each side by nucleotide sequences coding for at least one cloning site.

28. The hybrid origin of replication of claim 1, wherein the hybrid origin of replication is flanked on each side by nucleotide sequences coding for multiple cloning sites.

29. An exchangeable origin of replication cassette comprising a nucleotide sequence of a hybrid origin of replication flanked on each side by nucleotide sequences coding for at least one cloning site, wherein said cloning site is not within a regulatory or structural coding region, and wherein the hybrid origin of replication comprises the hybrid origin of replication of claim 1.

30. An exchangeable origin of replication cassette comprising a nucleotide sequence of a hybrid origin of replication flanked on each side by nucleotide sequences coding for multiple cloning sites, wherein said cloning sites are not within a regulatory or structural coding region, and wherein the hybrid origin of replication comprises the hybrid origin of replication of claim 1.

31. The exchangeable origin of replication cassette of claim 30, wherein said flanking cloning sites comprise restriction endonuclease sites.

32. The exchangeable origin of replication cassette of claim 30, wherein said multiple cloning sites comprise at least one BspEI, BglII, NsiI, NotI, SacI, SpeI or AlwNI restriction endonuclease site.

33. The exchangeable origin of replication cassette of claim 29, wherein the hybrid origin of replication comprises nucleotide sequences from a ColE1, pBR322, or pACYC184 origin of replication.

34. A plasmid comprising a hybrid origin of replication flanked by cloning sites, wherein said cloning sites are not within a regulatory or coding sequence, and wherein the hybrid origin of replication comprises the hybrid origin of replication of claim 1.

35. The plasmid of claim 34, wherein the plasmid has a backbone from pBR322.

36. The plasmid of claim 34, wherein the plasmid is SEQ ID NO: 22 or 23.

37. The plasmid of claim 34, wherein the hybrid origin of replication comprises pBR322 sequences and ColE1 sequences.

38. The plasmid of claim 34, wherein the hybrid origin of replication comprises a sequence from a pACYC184 origin of replication.

39. A bacterial host cell transformed with a plasmid of claim 34.

40. A method of producing a recombinant protein of interest comprising:
(a) transforming a suitable host cell with a plasmid of claim 34 containing a gene encoding a recombinant protein of interest, operatively linked to expression control sequences;
(b) growing a culture of said suitable host cell transformed with said plasmid under suitable conditions for expression of said recombinant protein; and
(c) recovering and purifying the protein of interest.

41. A method of producing plasmid DNA in bacteria comprising:
(a) transforming a suitable bacteria strain with the plasmid of claim 34; and
(b) growing a culture of said bacteria transformed with said plasmid under conditions which allow replication of said plasmid.

42. The hybrid origin of replication of claim 1, wherein nucleotides from the origin of replication from the first plasmid are replaced with nucleotides from the origin of replication from the second plasmid.

43. A method of creating the hybrid origin of replication from claim 1 comprising replacing nucleotides from the first origin of replication with nucleotides from the second origin of replication.

44. The hybrid origin of replication of claim 1 comprising at least 200 nucleotides from nucleotide sequences from a ColE1 origin of replication, the remaining nucleotides being from a pBR322 origin of replication.

45. The hybrid origin of replication of claim 1 comprising at least 250 nucleotides from nucleotide sequences from a ColE1 origin of replication, the remaining nucleotides being from a pBR322 origin of replication.

46. The plasmid of claim 34, wherein the plasmid is SEQ ID NO: 7 or 12.

47. A plasmid comprising a hybrid origin of replication flanked by cloning sites, wherein said cloning sites are not within a regulatory or coding sequence, wherein the hybrid origin of replication comprises nucleotide sequences from an origin of replication from a first plasmid contiguously linked to nucleotide sequences from an origin of replication from a second plasmid, and wherein the plasmid has a backbone from pBR322, and wherein the origin of replication from the first plasmid and the origin of replication from the second plasmid differ from one another.

* * * * *